United States Patent
Kats-Kagan et al.

(10) Patent No.: US 8,809,579 B2
(45) Date of Patent: Aug. 19, 2014

(54) GLUCAGON RECEPTOR ANTAGONIST COMPOUNDS, COMPOSITIONS CONTAINING SUCH COMPOUNDS AND METHODS OF USE

(75) Inventors: Roman Kats-Kagan, Brooklyn, NY (US); Christian P. Stevenson, Hoboken, NJ (US); Xibin Liao, Edison, NJ (US); Qinghong Fu, Plainsboro, NJ (US); Emma R. Parmee, Scotch Plains, NJ (US); Songnian Lin, Monroe, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 440 days.

(21) Appl. No.: 13/148,577

(22) PCT Filed: Feb. 3, 2010

(86) PCT No.: PCT/US2010/022963
§ 371 (c)(1),
(2), (4) Date: Aug. 9, 2011

(87) PCT Pub. No.: WO2010/098948
PCT Pub. Date: Sep. 2, 2010

(65) Prior Publication Data
US 2011/0312911 A1 Dec. 22, 2011

Related U.S. Application Data

(60) Provisional application No. 61/207,633, filed on Feb. 13, 2009.

(51) Int. Cl.
*C07C 229/00* (2006.01)
*A01N 43/04* (2006.01)

(52) U.S. Cl.
USPC .......................................... 562/444; 514/54

(58) Field of Classification Search
None
See application file for complete search history.

(56) References Cited

U.S. PATENT DOCUMENTS

2007/0249688 A1  10/2007  Conner et al.
2008/0085926 A1  4/2008  Stelmach et al.

*Primary Examiner* — Rosalynd Keys
*Assistant Examiner* — Jennifer C Sawyer
(74) *Attorney, Agent, or Firm* — Anna L. Cocuzzo; Catherine D. Fitch

(57) ABSTRACT

Glucagon receptor antagonist compounds are disclosed. The compounds are useful for treating type 2 diabetes and related conditions. Pharmaceutical compositions and methods of treatment are also included.

20 Claims, No Drawings

GLUCAGON RECEPTOR ANTAGONIST COMPOUNDS, COMPOSITIONS CONTAINING SUCH COMPOUNDS AND METHODS OF USE

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level>126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure>130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that trigger glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

The present invention relates to a compound represented by formula I:

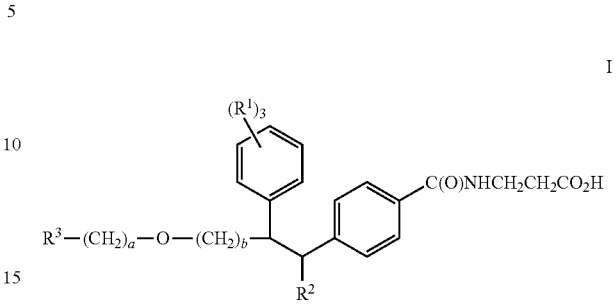

or a pharmaceutically acceptable salt or solvate thereof wherein:

each $R^1$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^2$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy;

a and b represents integers selected from 0 and 1, such that the sum of a and b is 0, 1 or 2;

$R^3$ represents Aryl$(R^d)_3$ or Heteroaryl$(R^d)_3$ wherein the Heteroaryl group is a 5-10 membered group containing one or two rings, said Heteroaryl group containing one to three heteroatoms, 0-3 of which are nitrogen, and 0-1 of which is oxygen or sulfur;

each $R^d$ represents H or is selected from the group consisting of: halo, CN, OH, $NO_2$, $CO_2R^a$, $C(O)NH_2$, $NR^aR^b$, $S(O)_pR^a$, $C_{1-10}$alkyl, halo$C_{1-10}$alkyl, $C_{2-10}$alkenyl, $C_{1-10}$alkoxy, halo$C_{1-10}$alkoxy, phenyl$(R^e)_3$ and HAR$(R^e)_3$;

each $R^e$ represents H or is selected from the group consisting of: halo, CN, $C_{1-6}$alkyl, halo$C_{1-6}$alkyl, $C_{1-6}$alkoxy and halo$C_{1-6}$alkoxy.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. Cycloalkenyl is a subset of alkenyl. If no number is specified, 4-8 carbon atoms are included. Examples include cyclopentenyl, cyclohexenyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Halogen" (Halo) includes fluorine, chlorine, bromine and iodine. The terms "haloalkyl", "haloalkoxy" and the like refer to halogenated alkyl and alkoxy groups of the size specified, substituted with 1-5 halo atoms, up to perhalo, and preferably from 1-3 halo atoms selected from fluoro and chloro. For example, halo$C_{1-6}$alkyl refers to a $C_{1-6}$alkyl group substituted with 1 to 5 halo atoms, up to perhalo.

One of the aspect of the invention relates to a compound represented by formula I:

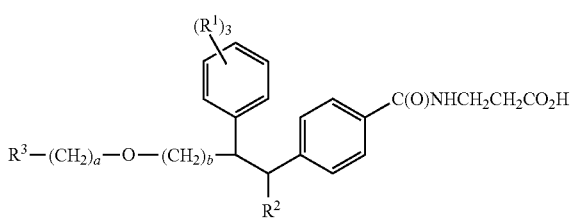

or a pharmaceutically acceptable salt or solvate thereof wherein:

each $R^1$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^2$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy;

a and b represents integers selected from 0 and 1, such that the stun of a and b is 0, 1 or 2;

$R^3$ represents Aryl$(R^d)_3$ or Heteroaryl$(R^d)_3$ wherein the Heteroaryl group is a 5-10 membered group containing one or two rings, said Heteroaryl group containing one to three heteroatoms, 0-3 of which are nitrogen, and 0-1 of which is oxygen or sulfur;

each $R^d$ represents H or is selected from the group consisting of: halo, CN, OH, $NO_2$, $CO_2R^a$, $C(O)NH_2$, $NR^aR^b$, $S(O)_pR^a$, $C_{1-10}$alkyl, halo$C_{1-10}$alkyl, $C_{2-10}$alkenyl, $C_{1-10}$alkoxy, halo$C_{1-10}$alkoxy, phenyl$(R^e)_3$ and HAR$(R^e)_3$;

each $R^e$ represents H or is selected from the group consisting of: halo, CN, $C_{1-6}$alkyl, halo$C_{1-6}$alkyl, $C_{1-6}$alkoxy and halo$C_{1-6}$alkoxy.

An aspect of the invention that is of interest relates to compounds of formula I-1:

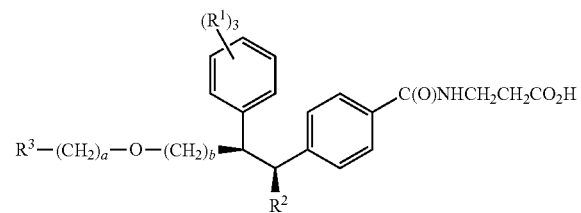

as well as pharmaceutically acceptable salts and solvates thereof.

Another aspect of the invention that is of interest relates to compounds of formula I-2:

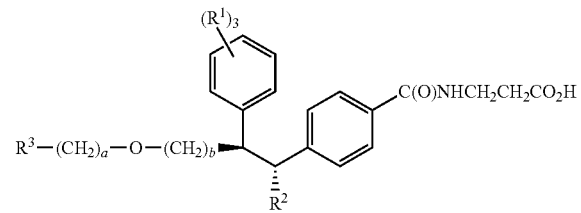

as well as pharmaceutically acceptable salts and solvates thereof.

Another aspect of the invention that is of interest relates to compounds of formula I-3:

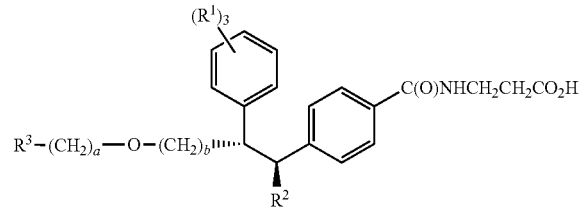

as well as pharmaceutically acceptable salts and solvates thereof.

Another aspect of the invention that is of interest relates to compounds of formula I-4:

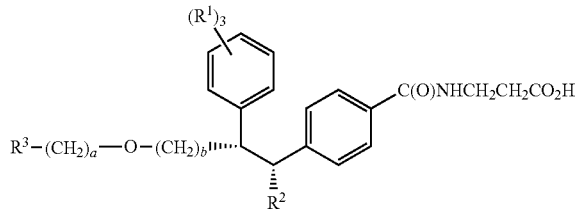

I-4 as well as pharmaceutically acceptable salts and solvates thereof.

Another aspect of the invention that is of interest relates to a compound of formula I or a pharmaceutically acceptable salt or solvate thereof wherein:

each $R^1$ represents H or is selected from the group consisting of halo, CN, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from oxo and $C_{1-6}$alkoxy;

p represents 0 or 2;

each $R^a$ and $R^b$ independently represents H or $CH_3$.

More particularly, another aspect of the invention that is of interest relates to a compound of formula I or a pharmaceutically acceptable salt or solvate thereof wherein:

each $R^1$ represents H or is selected from the group consisting of halo selected from chloro and fluoro, CN, $NH_2$, $SO_2CH_3$, $C_{1-3}$alkyl, $C_{2-3}$alkenyl or $C_{1-3}$alkoxy, the alkyl and alkenyl portions of, $C_{1-3}$alkyl, $C_{2-3}$alkenyl and $C_{1-3}$alkoxy being optionally substituted with 1-3 halo atoms selected from chloro and fluoro.

Even more particularly, an aspect of the invention that is of interest relates to a compound of formula I or a pharmaceutically acceptable salt or solvate thereof wherein:

each $R^1$ represents H or is selected from the group consisting of chloro, fluoro, CN, $CH_3$, $OCH_3$, $CF_3$, $OCF_3$.

Another aspect of the invention that is interest relates to a compound of formula I or a pharmaceutically acceptable salt or solvate thereof wherein:

$R^2$ represents $C_{1-4}$alkyl or $C_{2-4}$alkenyl, each optionally substituted with 1-3 halo atoms.

More particularly, another aspect of the invention that is interest relates to a compound of formula I or a pharmaceutically acceptable salt or solvate thereof wherein:

$R^2$ represents $C_{3-4}$alkyl optionally substituted with 1-3 halo atoms selected from fluoro and chloro.

Even more particularly, another aspect of the invention that is interest relates to a compound of formula I or a pharmaceutically acceptable salt or solvate thereof wherein:

$R^2$ represents —$CH_2CH_2CH_3$ or $CH_2CH_2CF_3$.

Another aspect of the invention that is of interest relates to a compound of formula I or a pharmaceutically acceptable salt or solvate thereof wherein a and b both equal zero; or a equals one and b equals zero; or a equals zero and b equals one, or a and b both equal one.

Another aspect of the invention that is of interest relates to a compound of formula I or a pharmaceutically acceptable salt or solvate thereof wherein:

$R^3$ represents Aryl$(R^d)_3$ or Heteroaryl$(R^d)_3$ wherein the Aryl portion of Aryl$(R^d)_3$ is phenyl or naphthyl, and the Heteroaryl portion of Heteroaryl$(R^d)_3$ is selected from the group consisting of pyridyl, pyrrolyl, pyrazolyl, pyrimidinyl, pyrazinyl, thiazolyl, thiophene, quinolinyl, isoquinolinyl and benzothiazolyl.

More particularly, another aspect of the invention that is of interest relates to a compound of formula I or a pharmaceutically acceptable salt or solvate thereof wherein:

$R^3$ represents Aryl$(R^d)_3$ or Heteroaryl$(R^d)_3$ wherein the Aryl portion of Aryl$(R^d)_3$ is phenyl or naphthyl, and the Heteroaryl portion of Heteroaryl$(R^d)_3$ is selected from the group consisting of pyridyl, pyrrolyl, thiophene, quinolinyl and benzothiazolyl.

Another aspect of the invention that is of interest relates to a compound of formula I or a pharmaceutically acceptable salt or solvate thereof wherein:

each $R^d$ represents H or is selected from the group consisting of halo, CN, $C_{1-10}$alkyl, halo$C_{1-10}$alkyl, $C_{1-10}$alkoxy, halo$C_{1-10}$alkoxy, phenyl$(R^e)_3$ and HAR$(R^e)_3$; wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl, and each $R^e$ represents H or is selected from the group consisting of: halo, CN, $C_{1-6}$alkyl, halo$C_{1-6}$alkyl, $C_{1-6}$alkoxy and halo$C_{1-6}$alkoxy.

In particular, another aspect of the invention that is of interest relates to a compound of formula I or a pharmaceutically acceptable salt or solvate thereof wherein:

each $R^d$ represents H or is selected from the group consisting of: halo, CN, $C_{1-4}$alkyl, halo$C_{1-4}$alkyl, $C_{1-4}$alkoxy, halo$C_{1-4}$alkoxy, phenyl$(R^e)_3$ and HAR$(R^e)_3$, wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl, and each $R^e$ represents H or is selected from the group consisting of halo selected from Cl, Br and F, CN, $C_{1-4}$alkyl, halo$C_{1-4}$alkyl, $C_{1-4}$alkoxy and halo$C_{1-4}$alkoxy, the halo portions of which are selected from Cl and F.

Even more particularly, another aspect of the invention that is of interest relates to a compound of formula I or a pharmaceutically acceptable salt or solvate thereof wherein:

each $R^d$ represents H or is selected from the group consisting of Cl, Br, F, CN, $CH_3$, t-butyl, $CF_3$, $OCH_3$, $OCHF_2$, $OCF_3$, phenyl$(R^e)_3$ and HAR$(R^e)_3$;

wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl, and each $R^e$ represents H or is selected from the group consisting of: Cl, F, CN, $CF_3$, $OCH_3$, $OCH(CH_3)_2$ and $OCF_3$.

A subset of compounds that is of interest relates to compounds of formula I or a pharmaceutically acceptable salt or solvate thereof wherein:

each $R^1$ represents H or is selected from the group consisting of halo, CN, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from oxo and $C_{1-6}$alkoxy;

p represents 0 or 2;

each $R^a$ and $R^b$ independently represents H or $CH_3$.

$R^2$ represents $C_{1-4}$alkyl or $C_{2-4}$alkenyl, each optionally substituted with 1-3 halo atoms.

a and b both equal zero; or a equals one and b equals zero; or a equals zero and b equals one, or a and b both equal one;

$R^3$ represents Aryl$(R^d)_3$ or Heteroaryl$(R^d)_3$ wherein the Aryl portion of Aryl$(R^d)_3$ is phenyl or naphthyl, and the Heteroaryl portion of Heteroaryl$(R^d)_3$ is selected from the group consisting of pyridyl, pyrrolyl, pyrazolyl, pyrimidinyl, pyrazinyl, thiazolyl, thiophene, quinolinyl, isoquinolinyl and benzothiazolyl;

each $R^d$ represents H or is selected from the group consisting of: halo, CN, $C_{1-10}$alkyl, halo$C_{1-10}$alkyl, $C_{1-10}$alkoxy, halo$C_{1-10}$alkoxy, phenyl$(R^e)_3$ and HAR$(R^e)_3$;

wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl, and each $R^e$ represents FI or is selected from the group consisting of: halo, CN, $C_{1-6}$alkyl, halo$C_{1-6}$alkyl, $C_{1-6}$alkoxy and halo$C_{1-6}$alkoxy.

Examples of compounds that fall within the invention described herein are in the tables and examples contained herein. Pharmaceutically acceptable salts and solvates of the compounds disclosed in the tables are included as well.

Another aspect of the invention that is of interest relates to a pharmaceutical composition comprising a compound as described above with respect to formula I or a pharmaceutically acceptable salt or solvate thereof in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I or a pharmaceutically acceptable salt or solvate thereof in an amount that is effective to treat type 2 diabetes mellitus.

Another aspect of the invention that is of interest relates to a method of delaying the onset of type 2 diabetes mellitus in a mammalian patient in need thereof comprising administering to the patient a compound as described above in accordance with formula I or a pharmaceutically acceptable salt or solvate thereof in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I or a pharmaceutically acceptable salt or solvate thereof in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I or a pharmaceutically acceptable salt or solvate thereof as described above.

Another aspect of the invention that is of interest relates to a method of treating obesity in a mammalian patient in need of such treatment comprising administering to said patient a compound in accordance with formula I as described above or a pharmaceutically acceptable salt or solvate thereof in an amount that is effective to treat obesity.

Another aspect of the invention that is of interest relates to a method of treating Syndrome X in a mammalian patient in need of such treatment, comprising administering to said patient a compound in accordance with formula I as described above or a pharmaceutically acceptable salt or solvate thereof in an amount that is effective to treat Syndrome X.

Another aspect of the invention that is of interest relates to a method of treating a lipid disorder selected from the group consisting of: dyslipidemia, hyperlipidemia, hypertriglyceridemia, hypercholesterolemia, low HDL and high LDL in a mammalian patient in need of such treatment, comprising administering to said patient a compound as described above with respect to formula I or a pharmaceutically acceptable salt or solvate thereof in an amount that is effective to treat said lipid disorder.

Another aspect of the invention that is of interest relates to a method of treating atherosclerosis in a mammalian patient in need of such treatment, comprising administering to said patient a compound in accordance with formula I as described above or a pharmaceutically acceptable salt or solvate thereof in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above or a pharmaceutically acceptable salt or solvate thereof in an amount that is effective to treat said condition.

Another aspect of the invention that is of interest relates to a method of delaying the onset of a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above or a pharmaceutically acceptable salt or solvate thereof in an amount that is effective to delay the onset of said condition.

Another aspect of the invention that is of interest relates to a method of reducing the risk of developing a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above or a pharmaceutically acceptable salt or solvate thereof in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, or a pharmaceutically acceptable salt or solvate thereof, and another compound that is selected from the list provided below.

(1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. No. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PIP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. Nos. 5,705,515, and 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), cetilistat, Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as B1BP3226, J-115814, BIBO 3304, LY-357897, CP-671906, GI-264879A, and those disclosed in U.S. Pat. No. 6,001,836, and PCP Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. patent application Ser. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472, 398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); (26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75;

(39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (45) dicarboxylate transporter inhibitors; (46) glucose transporter inhibitors; (47) phosphate transporter inhibitors; (48) Metformin (Glucophage®); (49) Topiramate (Topimax®); (50) peptide YY, PYY 3-36, peptide YY analogs, derivatives, and fragments such as BIM-43073D, BIM-4.3004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046,167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (53) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (54) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (55) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; (56) a minorex; (57) amphechloral; (58) amphetamine; (59) benzphetamine; (60) chlorphentermine; (61) clobenzorex; (62) cloforex; (63) clominorex; (64) clortermine; (65) cyclexedrine; (66) dextroamphetamine; (67) diphemethoxidine, (68) N-ethylamphetamine; (69) fenbutrazate; (70) fenisorex; (71) fenproporex; (72) fludorex; (73) fluminorex; (74) furfurylmethylamphetamine; (75) levamfetamine; (76) levophacetoperane; (77) mefenorex; (78) metamfepramone; (79) methamphetamine; (80) norpseudoephedrine; (81) pentorex; (82) phendimetrazine; (83) phenmetrazine; (84) picilorex; (85) phytopharm 57; (86) zonisamide, (87) neuromedin U and analogs or derivatives thereof, (88) oxyntomodulin and analogs or derivatives thereof,

(89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; (90) Qnexa; (91) smoking cessation agents, such as nicotine agonists, partial nicotine agonists, such as vareniciline, monoamine oxidase inhibitors (MAOIs), antidepressants such as bupropion, doxepine, and nortriptyline; and anxiolytic agents such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)

(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl) (3-{(1S)-2-fluoro-1-[3-fluoro-5-(1,3,4-oxadiazol-2-yl) phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl) azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S) (4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-(4-{(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl]-5-fluorobenzonitrile, 3-[(1S)-1-(1-{(5)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl] azetidin-1-yl}[3-(5-oxo-4,5-dihydro-1,3,4-oxadiazol-2-yl) phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b] pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro [cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1 (3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro [7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1 (3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl) spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy] phenyl}-4-[(4-fluorobenzyl)oxy]pyridin-2 (1H)-one, 4-[(4-fluorobenzyl)oxy]-1-{4-[(1-isopropylazetidin-3-yl)oxy] phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl) oxy]phenyl}pyridin-2(1H)-one, 4-[(5-chloropyridin-2-yl) methoxy]-1-{4-[(1-propylazetidin-3-yl)oxy] phenyl}pyridin-2(1H)-one, and 4-[(5-chloropyridin-2-yl] methoxy]-1-(4-{[(2S)-1-ethylazetidin-2-yl] methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-

(trifluoromethyl)-5,6,7,8-tetrahydro-1,2,4-triazolo[4,3-a] pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-{4-(3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4 (31-1)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed in combination with a compound of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof. Examples of other anti-obesity agents that can be employed in combination with a compound of formula I are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of: lovastatin, simvastatin, pravastatin, fluvastatin, atorvastatin, itavastatin, rosuvastatin and rivastatin.

Another aspect of the invention that is of interest relates to a method of reducing the risk of developing a condition selected from the group consisting of: hypercholesterolemia, atherosclerosis, low HDL levels, high LDL levels, hyperlipidemia, hypertriglyceridemia and dyslipidemia, and the sequelae of such conditions, delaying the onset or reducing the risk of developing said condition, comprising administering to a mammalian patient in need of such treatment therapeutically effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin, and even more particularly, a statin selected from the group consisting of: lovastatin, simvastatin, pravastatin, fluvastatin, atorvastatin, itavastatin, rosuvastatin and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin, atorvastatin or rosuvastatin.

Another aspect of the invention that is of interest relates to a method for delaying the onset or reducing the risk of developing atherosclerosis in a human patient in need of such treatment comprising administering to said patient effective amounts of a compound of formula as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a method of treating, delaying the onset, or preventing a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound.

More particularly, an aspect of the invention that is of interest relates to a method of treating, delaying the onset, or preventing a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound selected from torcetrapib and anacetrapib.

Another aspect of the invention that is of interest relates to a pharmaceutical composition comprising (1) a compound of formula I as described above; (2) a compound selected from the list provide above in combination with a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

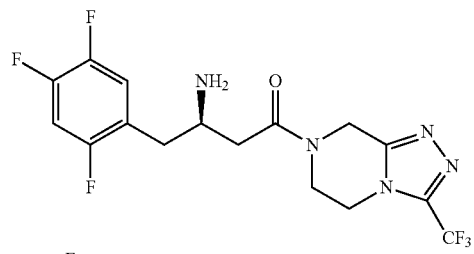

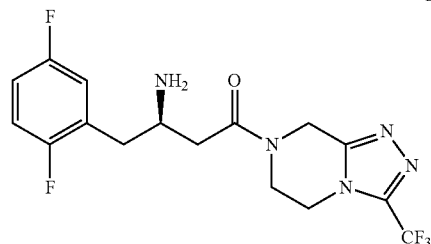

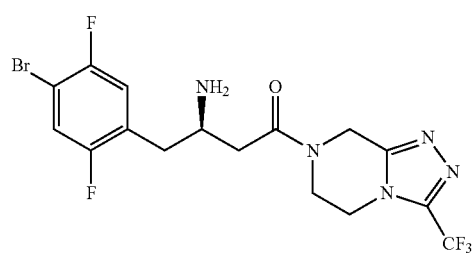

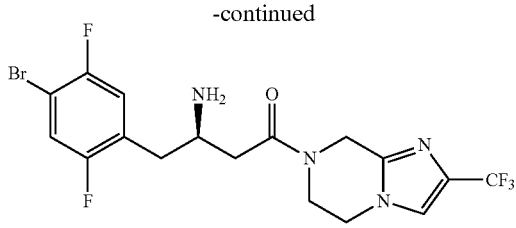

or a pharmaceutically acceptable salt or solvate thereof in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol fowl known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human, with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.0 |
| Benzalkonium chloride | 1.0 | Magnesium Stearate | 2.5 |
| Water for injection | t.d. 1.0 mL | Total (approx.) | 460 mg |
| Capsule | mg/cagsule | Aerosol | Per Canister |
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total (approx.) | 761.5 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as sitagliptin, vildagliptin, saxagliptin, and the like, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WO05/000809 A1 published on Jan. 6, 2005.

An aspect of the invention that is particular interest relates to a pharmaceutical composition that is comprised of a compound of formula I, or a pharmaceutically acceptable salt thereof, and a member selected from the group consisting of simvastatin, mevastatin, ezetimibe, atorvastatin, metformin, sibutramine, orlistat, Qnexa, topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide, rimonabant and taranabant, in combination with a pharmaceutically acceptable carrier.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg, 10 mg and 20 mg.

Methods of Synthesis:

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, 5$^{th}$ Ed., John Wiley and Sons, New York, N.Y., 2001; *Advanced Organic Chemistry*, Carey and Sundberg, Vol. A and B, 3$^{rd}$ Ed., Plenum Press, Inc., New York, N.Y., 1990; *Protective groups in Organic Synthesis*, Green and Wuts, 2$^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2$^{nd}$ Ed., Pergamon, New York, N.Y., 2000 and references cited therein. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Acros, (Pittsburgh, Pa.); BioBlocks, Inc. (San Diego, Calif.); and Trans World Chemicals (Rockville, Md.).

The procedures described herein for synthesizing the compounds may include one or more steps of protecting group manipulations and of purification, such as, re-crystallization, distillation, column chromatography, flash chromatography, thin-layer chromatography (TLC), and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amid; sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-butyl-lithium, phenyllithium, alkyl magnesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the Schemes below can be further manipulated, when appropriate, using the standard functional group transformation techniques available to those skilled in the art, to provide desired compounds described in this invention.

Throughout the synthesis schemes, abbreviations are used with the following meanings unless otherwise indicated:

| | |
|---|---|
| AIBN = azobisisobutyronitrile | aq = aqueous |
| BINAP = 2,2'-bis(diphenylphosphino)-1,1'-binaphthalene | Bn = benzyl |
| BOC, Boc = t-butyloxycarbonyl | BOP = benzotriazol-1-yloxy-tris(dimethylamino)-phosphonium hexafluorophosphate |
| Bu = butyl, t-Bu = t-butyl | BuLi, n-BuLi = n-butyllithium |
| CBZ, Cbz = Benzyloxycarbonyl | CDI = 1,1'-carbonyldiimidazole |
| (S)-DAIPEN = (S)-1,1-di(4-anisyl)-2-isopropyl-1,2-ethylenediamine = (S)-1,1-bis(4-methoxyphenyl)-3-methylbutane-1,2-diamine | dba = dibenzylideneacetone = trans,trans-1,5-diphenyl-1,4-pentadien-3-one |
| DCM = dichloromethane | 2,4-diClPh = 2,4-dichlorophenyl |
| DIAD = Diisopropyl azodicarboxylate | DIEA = diisopropylethylamine |
| DMA = N,N-dimethylacetamide | DMAP = 4-Dimethylaminopyridine |
| DMF = N,N-dimethylformamide | DMS = dimethyl sulfide |
| DMSO = dimethyl sulfoxide | dppf = 1,1'-bis(diphenylphosphino)ferrocene |
| EDC = 1-ethyl-3-(3-dimethylaminopropyl)-carbodiimide | eq. = equivalent(s) |
| Et = ethyl | EtOAc = ethyl acetate |

| | |
|---|---|
| EtOH = ethanol | g = gram(s) |
| HOBT, HOBt = 1-hydroxybenzotriazole | HPLC = High pressure liquid chromatography |
| IPA = isopropanol = 2-propanol | iPr = isopropyl = 2-propyl |
| KHMDS = potassium bis(trimethylsilyl)amide | KOtBu = potassium tert-butoxide |
| LC/MS = liquid chromatography - mass spectrometry | LDA = lithium diisopropylamide |
| LHMDS = lithium bis(trimethylsilyl)amide | M = molar |
| mCPBA = 3-chloroperoxybenzoic acid | Me = methyl |
| MeCN, CH$_3$CN = acetonitrile | MeOH = methanol |
| mg = milligram(s) | mL = milliliter(s) |
| mmol = millimole(s) | N = normal |
| NaOtBu = sodium tert-butoxide | NBS = N-bromosuccinimide |
| NCS = N-chlorosuccinimide | n-Pr = n-propyl |
| PCC = pyridinium chlorochromate | Pd/C = palladium on activated carbon |
| Ph = phenyl | PyBOP = Benzotriazol-1-yloxytripyrrolidinophosphonium hexafluorophosphate |
| RT, rt = room temperature | TBAF = tetrabutylammonium fluoride |
| Tf = triflate = trifluoromethanesulfonate | TFA = Trifluoroacetic acid |
| THF = tetrahydrofuran | TMS = trimethylsilyl |
| Tr = trityl = triphenylmethyl | (S)-xyl-SEGPHOS = (S)-5,5'-Bis[di(3,5-xylyl)phosphino]-4,4'-bi-1,3-benzodioxole |

Compounds of the present invention may be prepared according to the methodology outlined in the following general synthetic schemes.

Two embodiments of the present invention are summarized in Scheme 1. Saponification of ester 1 (methyl, ethyl) to give compound I is achieved with a base such as aqueous lithium hydroxide (LiOH) or aqueous sodium hydroxide in a polar solvent such as tetrahydrofuran, methanol, ethanol or a mixture of similar solvents. Alternatively, compound I, containing a t-butyl ester, can be converted to compound I using acid such as acetic acid or trifluoroacetic acid (TFA). In a second embodiment of the invention, alcohol 2 can be arylated with an appropriately substituted aryl halide in the presence of a base such as sodium or potassium t-butoxide in a polar solvent such as THF or DMF at temperatures between 70° C. and 200° C. Under these conditions, the ethyl ester of alcohol 2 is also saponified, thereby affording compound Ia. A wide variety of aryl fluorides are commercially available or are readily prepared using methods familiar to those skilled in the art. It should be noted that the stereochemistry at the position marked with an asterisk is retained in this transformation. For the remainder of these schemes, reactions are presumed to proceed with retention of stereochemistry unless stated otherwise.

Scheme 1

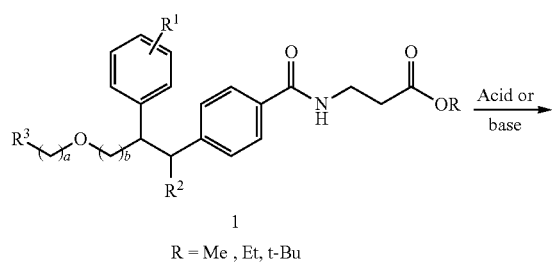

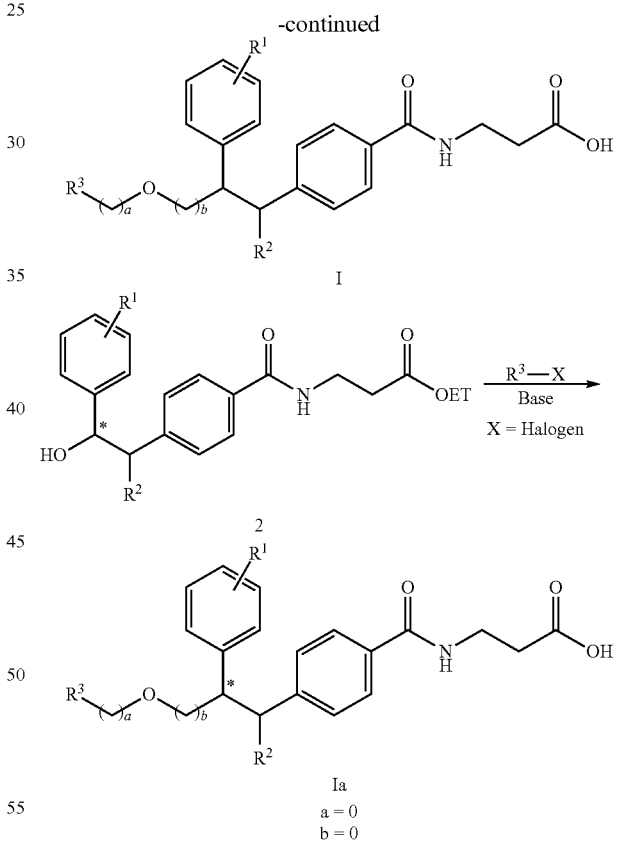

While the R$^d$ substituents are typically introduced as part of the larger R$^3$ sub-unit, it is also possible to convert certain R$^d$ substituents to others on advanced compounds as shown in Scheme 2. For instance, a bromide substituent can be further functionalized using a variety of metal-mediated cross-coupling reactions obvious to those skilled in the art. For instance, the bromide substituent of compound Ib can be converted to nitrile Ic in the presence of a palladium catalyst such as Pd(PPh$_3$)$_4$ and a cyanide source such as Zn(CN)$_2$ in a polar aprotic solvent such as DMF at a temperature of 80° C.

based on the chemistry described by Kubota and Rice, *Tetrahedron Letters*, 1998, 39, 2907-2910. Alternatively, compound Ib can be functionalized to afford compound Id under Suzuki coupling conditions with an aryl or heteroaryl boronic acid, palladium catalyst such as $Pd(PPh_3)_4$, base such as $Na_2CO_3$, in a mixed solvent system such as DMF or THF and water, at elevated temperatures such as 60° C. to 200° C. Numerous other metal-mediated functionalizations of compounds such as 1b will be obvious to those skilled in the art.

Additionally, a nitrile-containing aryl fluoride may be partially hydrolysed under the conditions for the conversion of alcohol 2 to compound Ia (Scheme 1), thereby affording primary amide Ie. Amide Ie can be transformed to nitrile Ic using various dehydration conditions, for instance by using $PdCl_2$ in aqueous acetonitrile at a temperature of 50° C. based on the chemistry described by Maffioli, et. al., *Organic Letters*, 2005, 23, 5237-5239.

Scheme 2

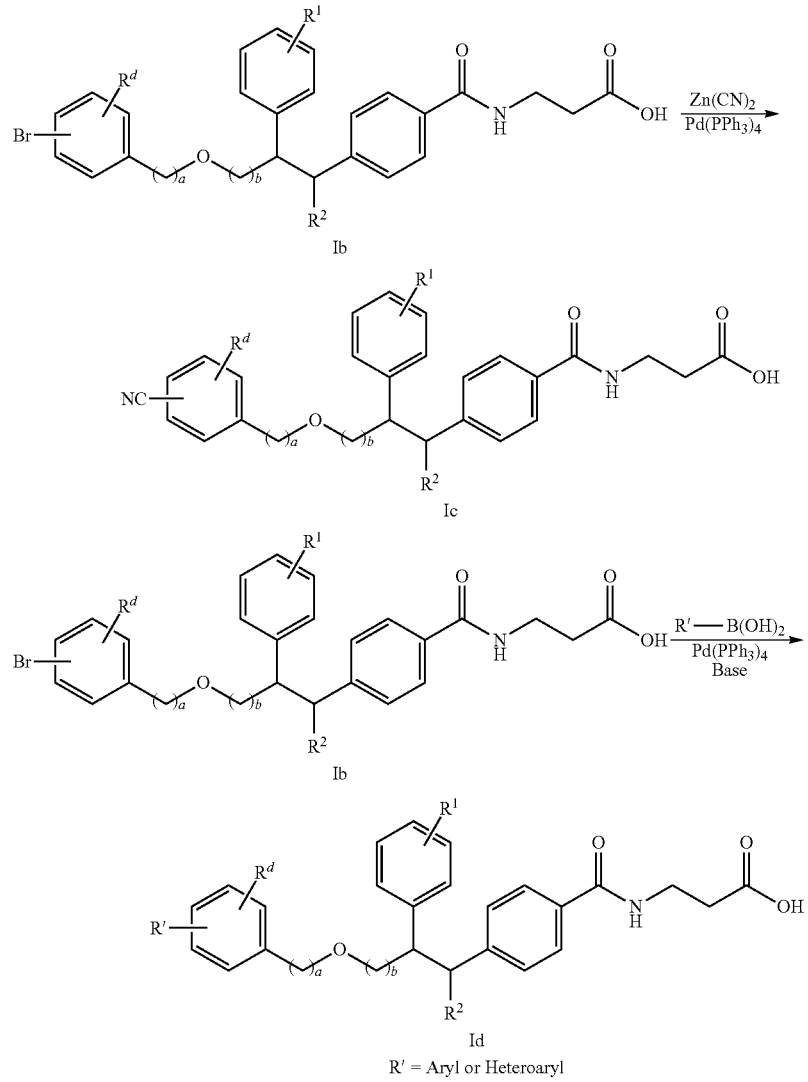

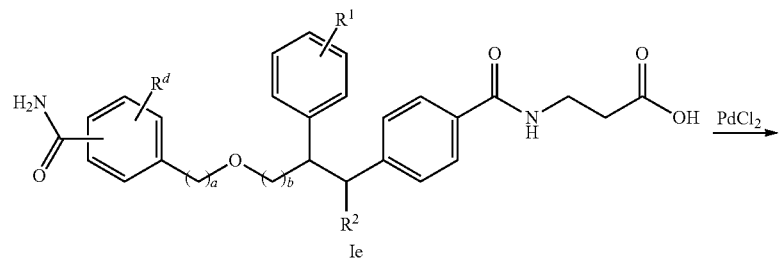

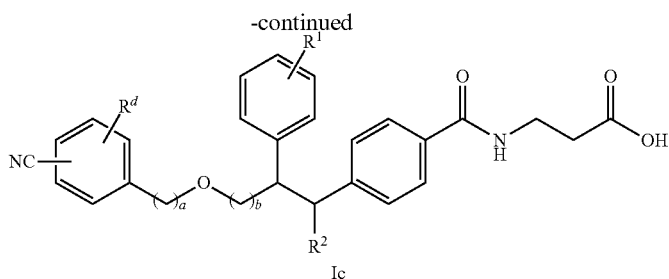

Ic

Multiple procedures for the production of intermediate 1 are summarized in Scheme 3. Intermediate 1 as can be prepared by alkylation of alcohol 3 with a bromomethyl arene or heteroarene under various conditions. For instance, a base such as sodium hydride can be used in a polar solvent such as DMF, or silver (I) oxide can be used in a solvent such as DCM at reflux. Alternatively, alcohol 3 can be converted to intermediate 1b by treatment with an appropriate hydroxyarene or hydroxyheteroarene under Mitsunobu reaction conditions with $Ph_3P$ and an azodicarboxylate such as DIAD in a solvent such as THF. Using the same procedure, alcohol 2 can be converted to intermediate 1c. It should be noted that the stereochemistry at the position marked with an asterisk is inverted in the transformation of 2 to 1c. Finally, intermediate 1c and 1d can be prepared from the carboxylic acid intermediate 4 by coupling with beta alanine ester (either methyl, ethyl or t-butyl ester) using benzotriazol-1-yloxytripyrrolidinophosphonium hexafluorophosphate and a base, generally N,N-diisopropylethylamine (DIEA), in a solvent such as dichloromethane, N,N-dimethylformamide (DMF) or acetonitrile at ambient temperature. Alternatively, the conversion of 4 to 1c and 1d may be carried out with EDC, HOBt, and a base such as DIEA in similar solvents as those used with PyBOP and DIEA. Many additional peptide coupling conditions are known and may also be used.

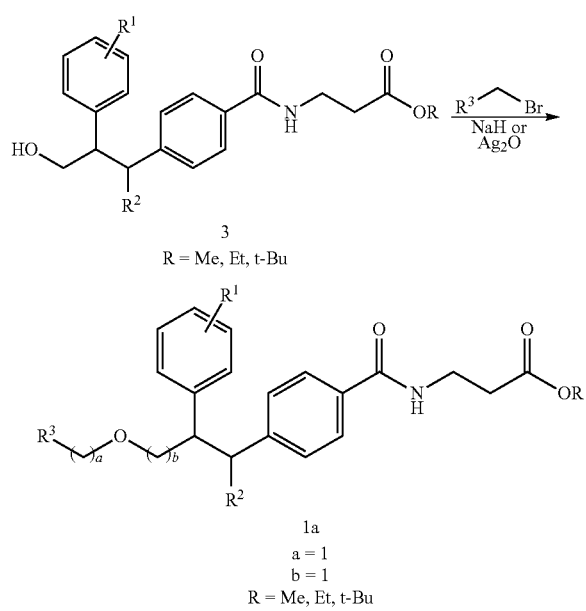

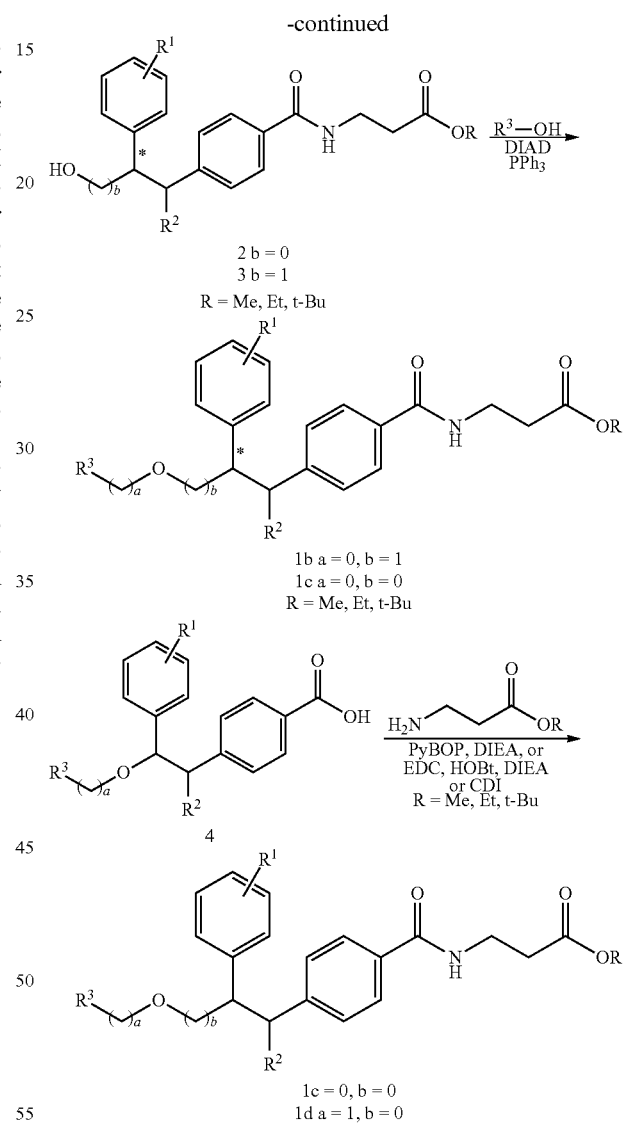

Scheme 4 summarizes the preparation of alcohol intermediate 2. Coupling of aryl alkyl ketones 5 and aryl bromide 6 may be achieved under transition-metal mediated conditions such as those described in *J. Am. Chem. Soc.*, Buchwald, S. L., et. al., 2000, 122, 1360-1370. Ketone 7 may be prepared, for instance, by heating 5 and 6 in the presence of a palladium source such as $Pd_2(dba)_3$, a ligand such as BINAP, a base such as NaOtBu, and a solvent such as THF. Reduction of ketone 7 to alcohol 8 can be accomplished with various achiral reductants, for instance $NaBH_4$. Alternatively, dynamic kinetic resolution of ketone 7 can afford highly enantio- and diastereoenriched alcohol 8 using catalysts such as those reviewed extensively in *Angew. Chem., Int. Ed.*, Noyori, R., et. al., 2001, 40, 40-73. For instance, this reaction can be performed using a ruthenium catalyst such as RuCl$_2$[(S)-xyl-SEG-PHOS][(S)-DAIPEN] and a base such as KOtBu in a solvent such as 2-propanol under an atmosphere of hydrogen. Deprotection of the t-butyl ester of alcohol 8 with an acid such as phosphoric acid in acetonitrile solvent can provide the acid 9. Intermediate 2 can then be accessed from acid 9 using the peptide coupling conditions described for the conversion of 4 to 1 (Scheme 3). A wide range of substituents may be introduced at R$^1$ and R$^2$ on alcohol 2 due to the functional group tolerance of the reactions employed in its preparation and the wide variety of starting ketones 5 which are either commercially available or readily prepared by methods known to those skilled in the art.

Scheme 4

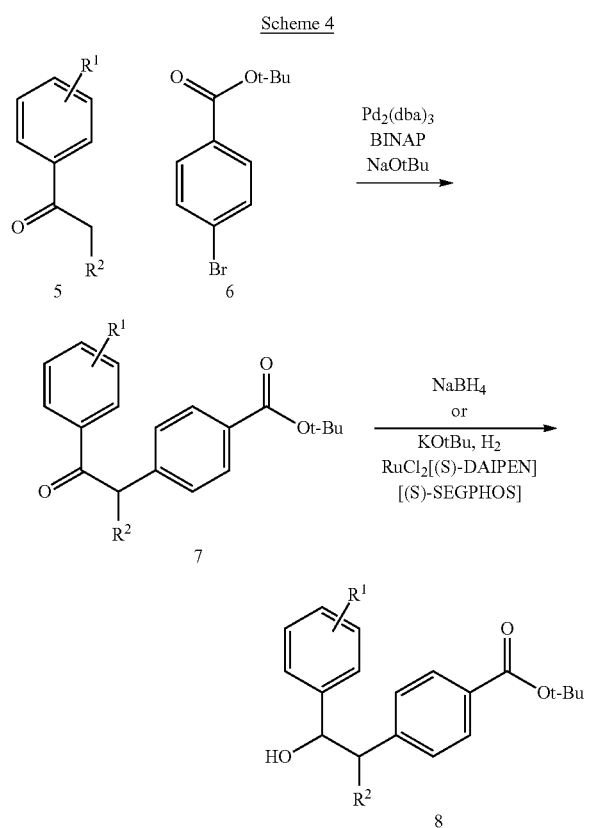

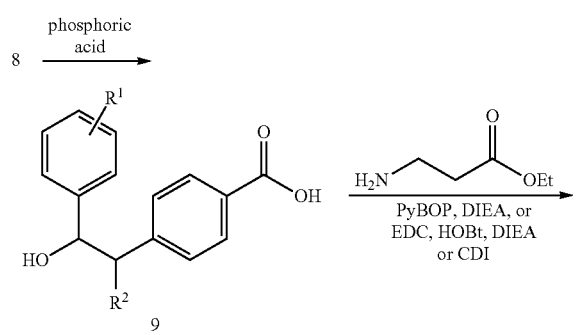

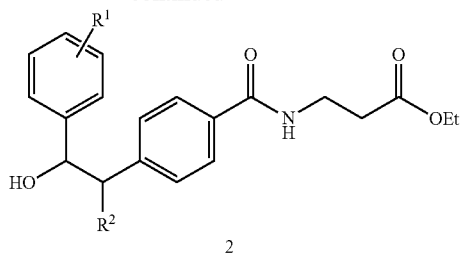

A procedure for inverting the hydroxyl stereocenter (marked with an asterisk) of alcohol 2 is summarized in Scheme 5. This is desirable in order to accomplish the stereoselective synthesis of single stereoisomers of compounds I in which a=0. Alcohol 2 can be converted to ester 10, with inversion of the hydroxyl stereocenter, by treatment with chloroacetic acid under the Mitsunobu conditions described for the conversion of 2 to 1b (Scheme 3). Selective cleavage of the chloroacetate ester in the presence of the ethyl ester can be accomplished under various conditions, for instance by treating ester 10 with ammonia in methanol. This affords alcohol 2 in which the hydroxyl stereocenter has been inverted from its original orientation.

Scheme 5

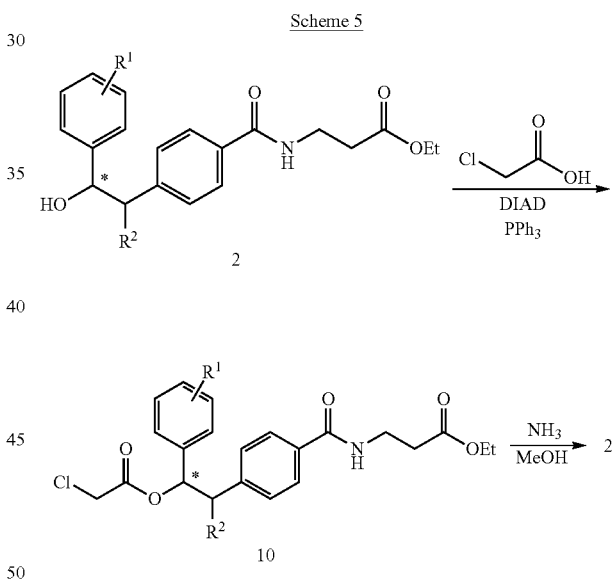

Preparation of alcohol 3a from diester 11 is depicted in Scheme 6. Diester 11 can be prepared as described in PCT Patent Publication WO 2008/042223 A1 published on 10 Apr. 2008. The methyl ester of 11 may be selectively deprotected to afford acid 12 using the basic conditions as described for the conversion of 1 (methyl and ethyl ester) to I (Scheme 1). Amide 13 can then be prepared from acid 12 using the peptide coupling conditions described for the conversion of 4 to 1 (Scheme 3). Selective deprotection of the t-butyl ester of amide 13 to afford acid 14 can be conducted under acidic conditions as described for the conversion of 1 (t-butyl ester) to I (Scheme 1). Finally, acid 14 can be reduced to afford alcohol 3 using a reducing agent selective for the carboxylic acid group, for instance borane dimethyl sulfide complex, in a solvent such as THF.

Scheme 6

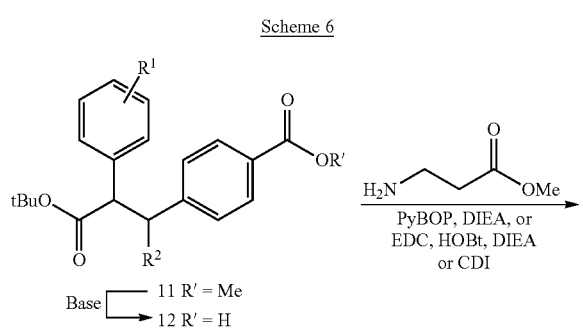

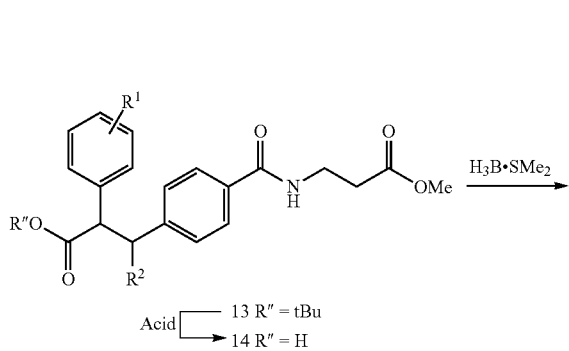

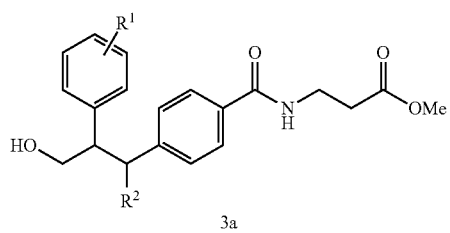

Preparation of alcohol 3b also proceeds from diester 11 as presented in Scheme 7. This route utilizes the same procedures presented in Scheme 6, except that they are conducted in a different order. The t-butyl ester of 11 can be deprotected with acid to afford carboxylic acid 15. The carboxylic acid can be reduced with borane dimethyl sulfide complex to provide alcohol 16. Saponification of 16 with base can afford carboxylic acid 17. The preparation of 3b can be completed by coupling acid 17 with beta alanine t-butyl ester.

Scheme 7

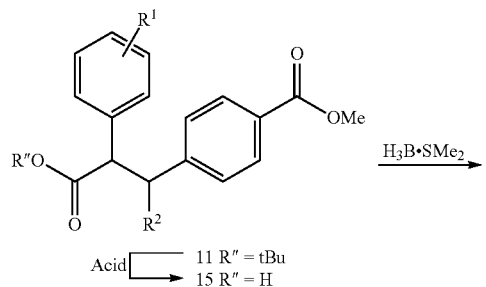

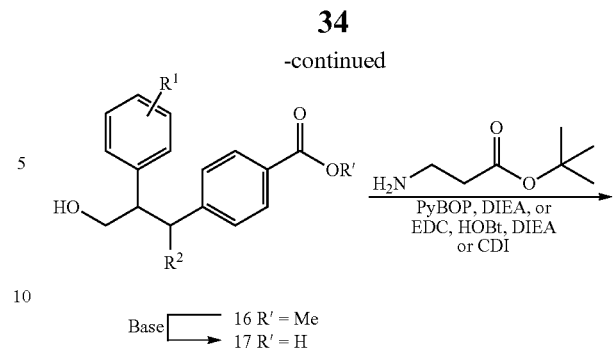

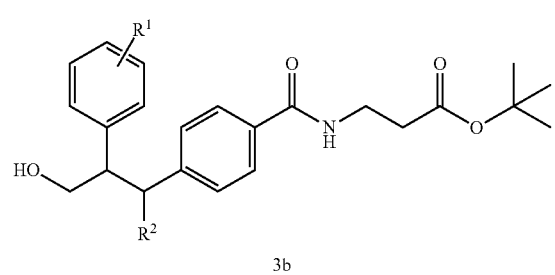

Two procedures for the preparation of carboxylic acid 4 are presented in Scheme 8. Acid 4a can be accessed from acid 9 by arylation with an appropriately substituted aryl halide under basic conditions such as those described for arylation of intermediate 2 (Scheme 1). This transformation was found to proceed particularly well using sodium hydride as a base and potassium benzoate as an additive in DMSO solvent according to the procedure described in *Org. Process Res. Dev.* Richard A. Berglund, 1997, 1, 328-330. Alternatively, the t-butyl ester of intermediate 18 can be removed to afford acid 4 under acidic conditions such as those described for the conversion of 1 to I (Scheme 1).

Scheme 8

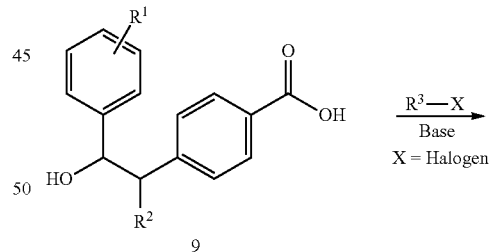

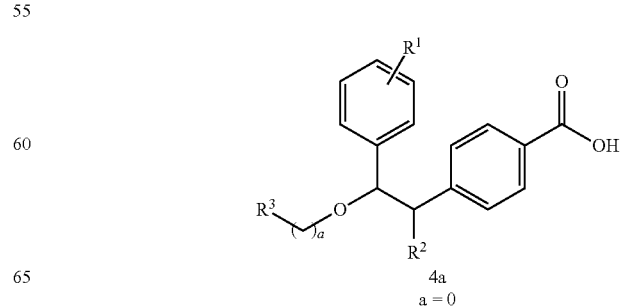

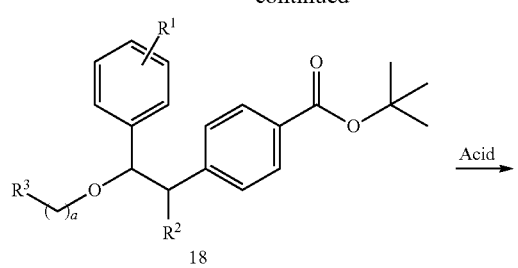

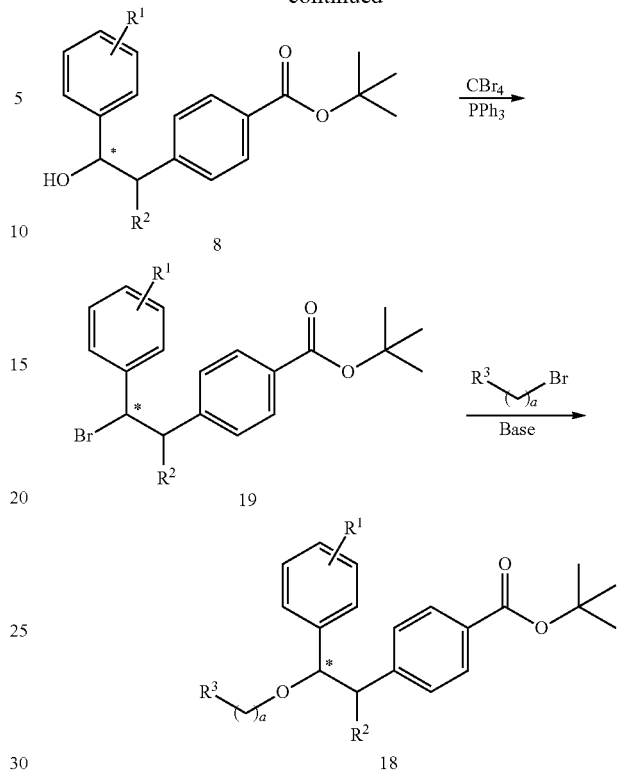

Intermediate 18 can be prepared in multiple ways from alcohol 8 as depicted in Scheme 9. Alcohol 8 can be alkylated to afford 18a with a bromomethyl arene or heteroarene in the presence of a base such as potassium t-butoxide in a solvent such as THF. Alternatively, alcohol 8 can be converted to intermediate 18b upon treatment with an appropriately electron-deficient heteroaryl bromide and a base such as sodium hydride in a polar aprotic solvent such as DMA with heating. An additional alternative is to convert alcohol 8 to bromide 19 under brominating conditions such as Ph₃P and carbon tetrabromide in a solvent such as DCM. This transformation occurs with inversion of stereochemistry at the position marked with an asterisk. Intermediate 18 can be accessed from bromide 19 by heating an appropriate hydroxyl-containing compound and a base such as sodium hydride in a polar, aprotic solvent such as DMF. This transformation also occurs with inversion of stereochemistry at the position marked with an asterisk.

Scheme 9

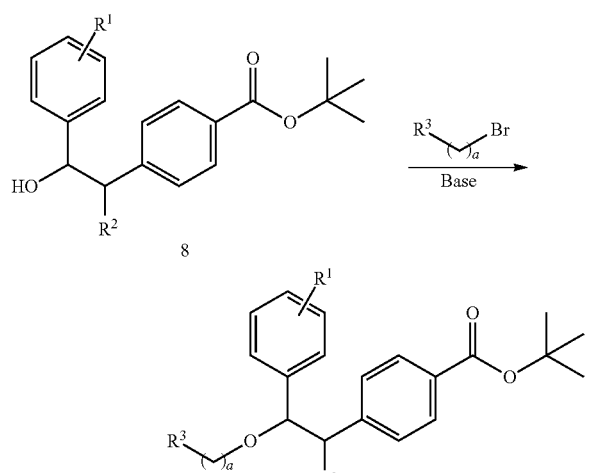

18a a = 1, R³ = Aryl, heteroaryl
18b a = 0, R³ = Heteroaryl

Separation of diastereomers can be carried out at various stages in the preparation of compounds I, as detailed in the examples which follow.

Analytical HPLC Mass Spectrometry Conditions:

LC1: Column: Waters Xterra MS C-18, 3.5 μm, 2.1×20 mm
  Temperature: 50° C.
  Eluent: 5:95 to 98:2 v/v acetonitrile/water+0.05% TFA over 1.25 min.
  Flow Rate: 1.5 mL/min, Injection 5 μL,
  Detection: PDA, 200-600 nm
  MS: mass range 150-750 amu; positive ion electrospray ionization LC2: Column: Waters Xterra IS C-18, 3.5 μm, 2.1×20 mm
  Temperature: 50° C.
  Eluent: 5:95 to 95:5 v/v acetonitrile/water+0.05% TFA over 3.00 min.
  Flow Rate: 1.5 mL/min, Injection 5 μL
  Detection: PDA, 200-600 nm
  MS: mass range 150-750 amu; positive ion electrospray ionization LC3: Column: Waters Xterra MS C-18, 3.5 μm, 3.0×50 mm
  Temperature: 50° C.
  Eluent: 10:90 to 98:2 v/v acetonitrile/water+0.05% TFA over 3.75 min.
  Flow Rate: 1.0 mL/min, Injection 10 μL
  Detection: PDA, 200-600 nm
  MS: mass range 150-750 amu; positive ion electrospray ionization LC4: Column: Waters Xterra IS C-18, 3.5 μm, 2.1×20 mm
  Temperature: 50° C.
  Eluent: 10:90 to 98:2 v/v acetonitrile/water+0.1% formic acid over 3.25 min.
  Flow Rate: 1.5 mL/min, Injection 5 μL
  Detection: PDA, 200-600 nm
  MS: mass range 150-750 amu; positive ion electrospray ionization Preparative Reverse Phase HPLC(RP-HPLC) Conditions:
  Column: Atlantis dC18, 5 μm, 19×150 mm
  Flow Rate: 20.0 mL/min
  Eluent: 10:90 to 100:0 v/v acetonitrile/water+0.1% TFA over 10.0 min.
  Temperature: ambient
  Detection: PDA, 254 nm Preparative thin layer chromatography (PTLC) was performed on 20×20 cm plates (500-1500 μm thick silica gel). Silica gel chromatography was performed on a Combiflash Companion flash chromatography system.

The following examples are provided so that the invention might be more fully understood. They should not be construed as limiting the invention in any way.

Intermediate 1

Ethyl N-(4-{(1R)-1-[(R)-(4-chlorophenyl)(hydroxy)methyl]butyl}benzoyl)-β-alaninate

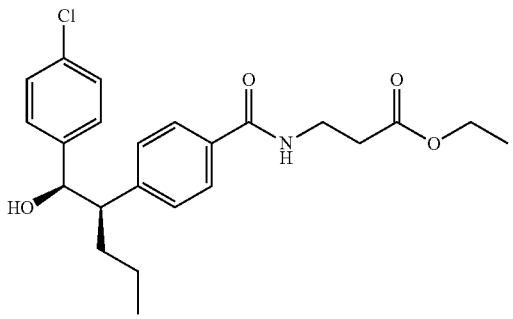 [SMILES: CCC[C@H](c1ccc(C(=O)NCCC(=O)OCC)cc1)[C@@H](O)c1ccc(Cl)cc1]

Step A. tert-Butyl 4-[2-(4-chlorophenyl)-1-propylethan-2-one-1-yl]benzoate

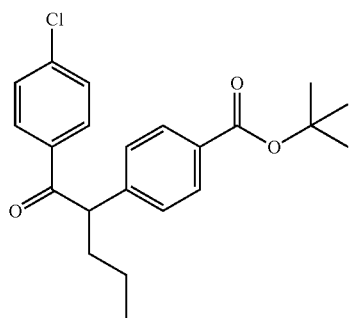 [SMILES: CCCC(C(=O)c1ccc(Cl)cc1)c1ccc(C(=O)OC(C)(C)C)cc1]

A 3-neck flask was charged with NaOtBu (2.85 g, 28.6 mmol) and dry THF (50 mL) under nitrogen. Tris(dibenzylideneacetone)dipalladium(0) (0.26 g, 0.28 mmol) and (S)-Tol-Binap (0.47 g, 0.69 mmol) were then added under nitrogen. After stirring for 15 min, 1-(4-chlorophenyl)pentan-1-one (4.21 g, 21.0 mmol) was added, followed by tert-butyl 4-bromobenzoate (5.0 g, 19.1 mmol) under nitrogen. The mixture was heated at 60° C. for 8 hours. The mixture was diluted with heptane (100 mL) and poured into a solution of saturated NaHCO₃ (aq) (60 mL) and ice (40 g). The resulting layers were separated, and the aqueous phase was back-extracted with methyl tert-butyl ether (50 mL). The combined organics were washed with saturated NaHCO₃ (aq) then 10% NaCl (aq). The organic solution was filtered through a bed of silica 60 (84 g, wetted with 1:1 methyl tert-butyl ether/heptane), and washed with 1:1 methyl tert-butyl ether/heptane (600 mL). The combined filtrate was concentrated to afford an orange oil that was used directly for the next step: $^1$H NMR (500 MHz, CDCl₃): δ 7.91 (d, J=8.1 Hz, 2H); 7.86 (d, J=8.4 Hz, 2H); 7.35 (d, J=8.4 Hz, 2H); 7.32 (d, J=8.2 Hz, 2H); 4.53 (1, J=7.2 Hz, 1H); 2.19-2.09 (m, 1H); 1.85-1.76 (m, 1H); 1.56 (s, 9H); 1.35-1.18 (m, 2H); 0.91 (t, J=7.3 Hz, 3H); LC3: 1.35 min. (M-tBu+H)⁺ 317.

Step B. tert-Butyl 4-{(1R)-1-[(R)-(4-chlorophenyl)(hydroxy)methyl]butyl}benzoate

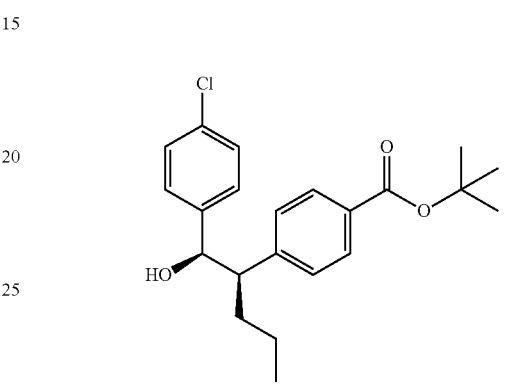

To degassed 2-propanol (5.0 mL) was added RuCl₂-[(8)-xyl-SEGPHOS][(S)-DAIPEN] (16.2 mg, 0.0134 mmol) and potassium t-butoxide (300 mg, 2.67 mmol). After this mixture was stirred at room temperature for 2 hours, the material obtained in Step A was added in 2-propanol (25 mL). This mixture was then treated with hydrogen (100 psi) at room temperature for 18 hours. The mixture was concentrated, then the residue was recrystallized from IPA/water to afford the title compound. $^1$H NMR (400 MHz, CDCl₃) δ 7.96 (m, 2H), 7.32 (m, 2H), 7.26 (m, 2H), 7.22 (m, 2H), 4.76 (dd, J=7.7, 2.9 Hz, 1H), 2.89 (ddd, J=11.5, 7.7, 4.2 Hz, 1H), 1.84 (d, J=2.9 Hz, 1H), 1.62 (s, 9H), 1.61 (m, 1H), 1.41 (m, 1H), 1.05 (m, 2H), 0.76 (t, J=7.3 Hz, 3H); LC2: 2.38 min. (M–H₂O-tBu+H)⁺ 301; Chiral SFC Method: Chiralpak AD-H (250×4.6 mm), isocratic 15% MeOH/CO₂, 1.5 mL/min, 200 bar, 35° C., 215 nm, 15 minutes: desired alcohol retention time=9.8 min; enantiomeric alcohol, retention time=10.6 min; diastereomeric alcohols retention times=5.2 and 6.3 min.

Step C. 4-{(1R)-1-[(R)-(4-Chlorophenyl)(hydroxy)methyl]butyl}benzoic acid

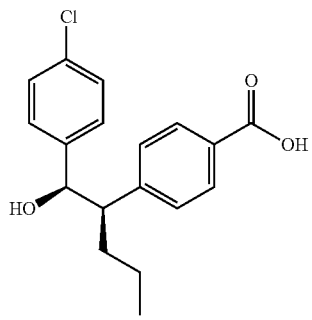 [SMILES: CCC[C@H](c1ccc(C(=O)O)cc1)[C@@H](O)c1ccc(Cl)cc1]

Orthophosphoric acid (85 wt %, 11.4 g, 99 mmol) was added to a slurry of tert-butyl 4-[(1R,2R)-2-(4-chlorophenyl)-1-propylethan-2-hydroxyl-1-yl]benzoate (7.42 g, 19.8 mmol) in acetonitrile (75 mL). The mixture was purged with nitrogen, then heated at 65° C. for 3.5 hours. The mixture was allowed to cool to 40° C., then water (25 mL) was added dropwise. Once crystallization began, additional water (50 mL) was added and the mixture was allowed to cool to room temperature. The precipitate was collected by vacuum filtration, washed with 3:1 water:acetonitrile (35 mL), then dried in vacuo at 65° C. overnight to afford the title compound as a light green solid. $^1$H NMR (400 MHz, DMSO-$d_6$) δ 12.71 (br s, 1H); 7.79 (d, J=8.3 Hz, 2H); 7.29 (d, J=8.4 Hz, 2H); 7.19-7.25 (m, 4H); 5.32 (br s, 1H); 4.76 (d, J=6.3 Hz, 1H); 2.85 (dt, J=10.7, 5.4 Hz, 1H); 1.61 (m, 1H); 1.44 (m, 1H); 1.00 (m, 2H); 0.73 (t, J=7.3 Hz, 3H)); LC4 3.00 min. (M+H)$^+$ 317.

Step D. Ethyl N-(4-{(1R)-1-[(R)-(4-chlorophenyl)(hydroxy)methyl]butyl}benzoyl)-β-alaninate

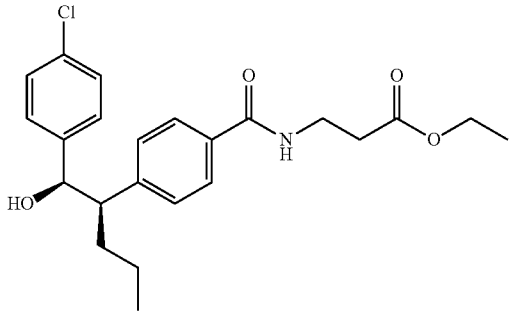 [SMILES: CCC[C@H](c1ccc(C(=O)NCCC(=O)OCC)cc1)[C@@H](O)c1ccc(Cl)cc1]

To a solution of the product of Step C (5.00 g, 15.7 mmol) in THF (100 mL) was added CDI (3.05 g, 18.82 mmol). After stirring at room temperature for one hour, β-alanine ethyl ester hydrochloride (3.61 mg, 23.53 mmol) was added, then the mixture was stirred at room temperature for two days. The mixture was diluted with EtOAc then washed with 1N NaOH, then water, then brine. The organic layer was dried over MgSO$_4$, filtered, then concentrated to provide the title compound which was used without further purification. $^1$H NMR (499 MHz, CDCl$_3$): δ 7.74 (d, J=7.9 Hz, 2H); 7.32 (d, =8.2 Hz, 2H); 7.28 (t, J=4.0 Hz, 2H); 7.25-7.15 (m, 2H); 6.88 (brs, 1H); 4.77 (d, 0.1=7.7 Hz, 1H); 4.20 (q, J=7.1 Hz, 2H); 3.75 (q, J=5.9 Hz, 2H); 2.89 (ddd, J=11.1, 7.7, 4.1 Hz, 1H); 2.66 (1, J=5.8 Hz, 2H); 1.47-1.37 (m, 2H); 1.30 (t, J=7.1 Hz, 3H); 1.11 (m, 2H); 0.76 (t, J=7.3 Hz, 3H). LC-MS: LC1 1.14 min. (M+H)$^+$ 418.

Intermediate 2

Ethyl N-(4-{(1R)-1-[(S)-(4-chlorophenyl)(hydroxy)methyubutyl]benzoyl}-β-alaninate

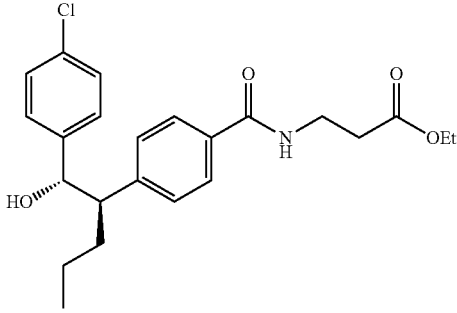 [SMILES: CCC[C@H](c1ccc(C(=O)NCCC(=O)OCC)cc1)[C@H](O)c1ccc(Cl)cc1]

Step A. Ethyl N-(4-{(1R)-1-[(3)-[(chloroacetyl)oxy](4-chlorophenyl)methyl]butyl}benzoyl)-β-alaninate

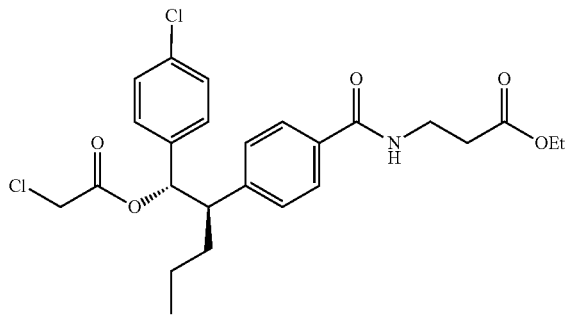 [SMILES: CCC[C@H](c1ccc(C(=O)NCCC(=O)OCC)cc1)[C@H](OC(=O)CCl)c1ccc(Cl)cc1]

Triphenylphosphine (2.51 g, 9.57 mmol), INTERMEDIATE 1 (2.00 g, 4.79 mmol) and chloroacetic acid (543 mg, 5.74 mmol) were dissolved in anhydrous THF. DIAD (1.40 mL, 7.18 mmol) was added dropwise maintaining the temperature of the solution below 30° C. After stirring for 30 minutes at RT, the mixture was concentrated. The resulting residue was purified by silica gel chromatography eluting with 0-30% EtOAc/hexanes to provide the title compound. $^1$H NMR (600 MHz, CDCl$_3$): δ 7.58 (d, J=8.0 Hz, 2H); 7.15 (d, J=8.3 Hz, 2H); 7.06 (d, J=8.0 Hz, 2H); 6.99 (d, J=8.3 Hz, 2H); 6.80 (t, J=6.2 Hz, 1H); 5.87 (d, =8.4 Hz, 1H); 4.18 (q, J=7.2 Hz, 2H); 4.09 (dd, J=12.5, 12.5 Hz, 2H); 3.73-3.67 (m, 2H); 3.18-3.13 (m, 1H); 2.65-2.60 (m, 2H); 1.83 (m, 1H), 1.70 (m, 1H), 1.30 (I, J=7.2 Hz, 3H); 1.15-1.06 (m, 2H); 0.84 (t, J=7.3 Hz, 3H). LC1 1.29 min. (M+H)$^+$ 563.

Step B. Ethyl N-4-{(1R)-1-[(S)-(4-chlorophenyl)(hydroxy)methyl]butyl}benzoyl)β-alaninate

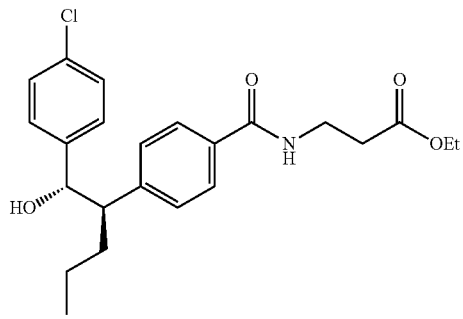 [SMILES: CCC[C@H](c1ccc(C(=O)NCCC(=O)OCC)cc1)[C@H](O)c1ccc(Cl)cc1]

To a solution of the product of Step A (600 mg, 1.21 mmol) in MeOH (50 mL) at RT was added ammonia (7.0 N in MeOH, 3.47 mL, 24.3 mmol). After being stirred for 1.5 hours, the mixture was concentrated to afford the title compound. $^1$H NMR (500 MHz, CDCl$_3$): δ 7.59 (d, 8.1 Hz, 2H); 7.23-7.17 (d, J=8.2 Hz, 2H); 7.07 (d, J=8.1 Hz, 2H); 7.04 (d, J=8.2 Hz, 2H); 6.85 (t, J=6.2 Hz, 1H); 4.76 (d, J=7.0 Hz, 1H); 4.18 (q, 0.1=7.1 Hz, 2H); 3.75-3.63 (m, 2H); 2.96 (ddd, J=11.3, 7.0, 3.7 Hz, 1H); 2.67-2.60 (m, 2H); 2.22 (br, 1H); 1.95 (dddd, J=13.6, 9.9, 6.7, 3.7 Hz, 1H); 1.78-1.67 (m, 1H);

1.29 (t, J=7.2 Hz, 3H); 1.18-1.02 (m, 2H); 0.91-0.81 (t, J=7.3 Hz, 3H). LC1 1.15 min. (M+H)⁺ 418.

Example 1

N-(4-{(1R)-1-[(R)-(4-chlorophenyl)(3,4-dichlorophenoxy)methyl]butyl}benzoyl)-β-alanine

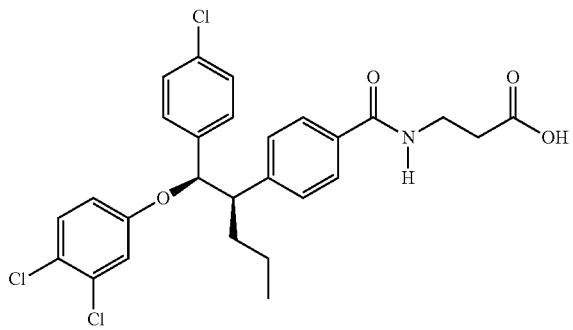 [SMILES: CCC[C@H](c1ccc(C(=O)NCCC(=O)O)cc1)[C@@H](Oc1ccc(Cl)c(Cl)c1)c1ccc(Cl)cc1]

To a solution of INTERMEDIATE 2 (50 mg, 0.12 mmol), 3,4-dichlorophenol (23.4 mg, 0.144 mmol), and triphenylphosphine (94 mg, 0.36 mmol) in THF at 0° C. was added DIAD (46.5 μL, 0.239 mmol), then the reaction mixture was allowed to warm to RT overnight. The mixture was concentrated, then the residue was purified by PTLC. The resulting material was used directly for the next step.

The product of the previous step was dissolved in EtOH (1 mL), then NaOH (1.0 N in H₂O, 0.2 mL, 0.2 mmol) was added. The mixture was stirred for 1-2 hours then diluted with DCM (20 mL) and 2 N HCl(aq). The organic layer was washed with brine, dried over MgSO₄, filtered, then concentrated. The resulting residue was purified by silica gel chromatography eluting with 10% MeOH/DCM to afford the title compound. ¹H NMR (500 MHz, CD₃OD): δ 7.70 (d, J=8.0 Hz, 2H); 7.32 (d, J=8.5 Hz, 2H); 7.27 (d, J=8.5 Hz, 2H); 7.21 (d, J=8.5 Hz, 2H); 7.20 (d, J=6.5 Hz, 1H); 6.90 (d, J=3.0 Hz, 1H); 6.69 (dd, J=9.0, 2.5 Hz, 1H); 5.43 (d, J=6.5 Hz, 1H); 3.61 (t, J=6.5 Hz, 2H); 3.17-3.14 (m, 1H); 2.62 (t, J=6.5 Hz, 2H); 1.85-1.77 (m, 1H); 1.58-1.52 (m, 1H); 1.16-1.10 (m, 2H); 0.81 (t, J=7.5 Hz, 3H); LC1 1.25 min. (M+H)⁺ 536.

Example 2

N-(4-{(1R)-1-[(R)-(3-chloro-5-cyanophenoxy)(4-chlorophenyl)methyl]butyl}benzoyl)-β-alanine

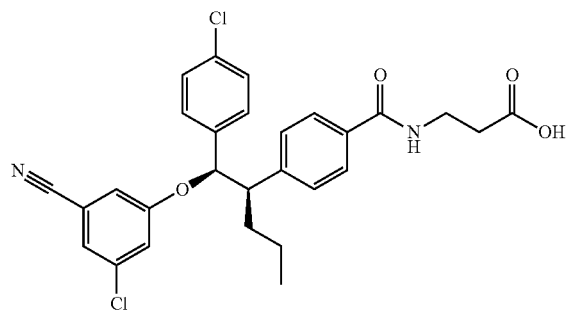 [SMILES: CCC[C@H](c1ccc(C(=O)NCCC(=O)O)cc1)[C@@H](Oc1cc(Cl)cc(C#N)c1)c1ccc(Cl)cc1]

To a solution of INTERMEDIATE 1 (100 mg, 0.239 mmol) and 3-chloro-5-fluorobenzonitrile (40.9 mg, 0.263 mmol) in DMF (2 mL) was added potassium tert-butoxide (107 mg, 0.957 mmol), then the resulting mixture was allowed to stir at 120° C. for 16 hours. After being allowed to cool to RT, the mixture was diluted with 2 N HCl (aq) then extracted with EtOAc. The organic layer was washed twice with water then concentrated. The resulting yellow residue was purified by preparative reverse phase HPLC eluting with 30-100% CH₃CN/water+0.1% TFA. Following lyophilization, this afforded the title compound as a white solid, ¹H NMR (500 MHz, CD₃OD): δ 7.70 (d, J=8.5 Hz, 2H); 7.34 (d, J=8.5 Hz, 2H); 7.30 (d, J=8.0 Hz, 2H); 7.25 (d, J=8.5 Hz, 2H); 7.20 (s, 1H); 7.09 (s, 1H); 7.06 (s, 1H); 5.55 (d, 0.1=6.5 Hz, 1H); 3.61 (t, J=7.0 Hz, 2H); 3.16 (m, 1H); 2.62 (t, J=7.0 Hz, 2H); 1.80 (m, 1H); 1.54 (m, 1H); 1.11-1.07 (m, 2H); 0.78 (t, J=7.2 Hz, 3H); LC3 3.93 min. (M+H)⁺ 523.

Example 3

N-[4-((1R)-1-{(R)-(4-chlorophenyl)[(2-cyano-4'-methylbiphenyl-4-yl)oxy]methyl}butyl)benzoyl]-β-alanine

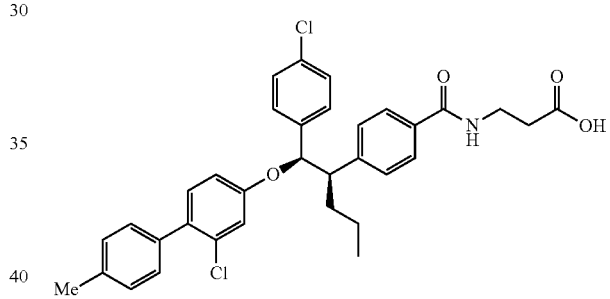

Step A. N-(4-{(1R)-1-[(4-Bromo-3-cyanophenoxy)(4-chlorophenyl)methyl]butyl}benzoyl)-β-alanine

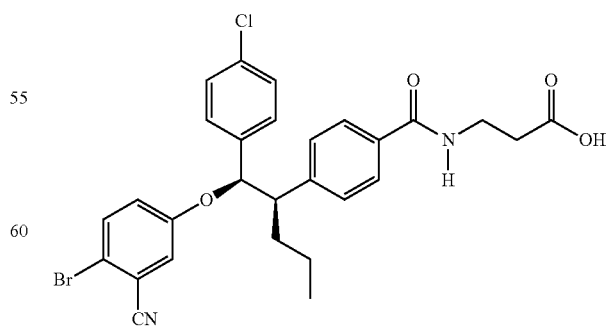

To a flask charged with potassium tert-butoxide (0.805 g, 7.18 mmol), 2-bromo-5-fluorobenzonitrile (0.622 g, 3.11 mmol), and INTERMEDIATE 1 (1.00 g, 2.39 mmol) was added THF (16 mL), then the mixture was stirred at 70° C. for 16 hours. After cooling to RT, the mixture was diluted with NH$_4$Cl (aq) then extracted with EtOAc. The organic layer was dried over MgSO$_4$, filtered, then concentrated. The resulting residue was purified by PTLC to afford the title compound. LC1 1.24 min. (M+H)$^+$ 569.

Step B. N-[4-((1R)-1-{(R)-(4-Chlorophenyl)[(2-cyano-4'-methylbiphenyl-4-yl)oxy]methyl}butyl)benzoyl]-β-alanine

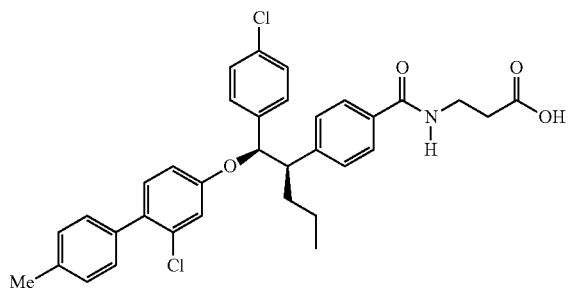 [SMILES: CCC[C@H](c1ccc(C(=O)NCCC(=O)O)cc1)[C@@H](Oc1ccc(-c2ccc(C)cc2)c(Cl)c1)c1ccc(Cl)cc1]

To a flask charged with Na$_2$CO$_3$ (2.0 M in water, 132 μL, 0.263 mmol), Pd(PPh$_3$)$_4$ (10.1 mg, 8.77 μmol) and (4-methylphenyl)boronic acid (36.5 mg, 0.175 mmol) was added a solution of the product from Step A (50 mg, 0.088 mmol) in DMF, then the mixture was stirred at 60° C. overnight. After cooling to RT, the mixture was purified by preparative reverse phase HPLC eluting with 50-100% acetonitrile/water+0.1% TFA to afford the title compound. $^1$H NMR (500 MHz, CD$_3$OD): δ 7.81 (d, J=8.5 Hz, 2H); 7.43 (d, J=7.5 Hz, 4H); 7.36 (t, J=8.5 Hz, 4H); 7.35 (d, J=8.5 Hz, 1H); 7.28 (d, J=3.0 Hz, 1H); 7.26 (d, J=8.0 Hz, 2H); 7.19 (dd, J=8.5, 2.5 Hz, 1H); 5.77 (d, J=7.0 Hz, 1H); 3.65-3.61 (m, 2H); 3.31 (m, 1H), 3.25 (s, 3H); 2.65 (t, J=6.5 Hz, 2H); 1.88-1.86 (m, 1H); 1.63-1.61 (m, 1H); 1.16-1.11 (m, 2H); 0.79 (t, J=7.0 Hz, 3H); LC1 1.27 min. (M+H)$^+$ 581.

Example 4

N-[4-((1R)-1-{(R)-(4-chlorophenyl)[(3-cyano-4'-methylbiphenyl-4-yl)oxy]methyl}butyl)benzoyl]-β-alanine

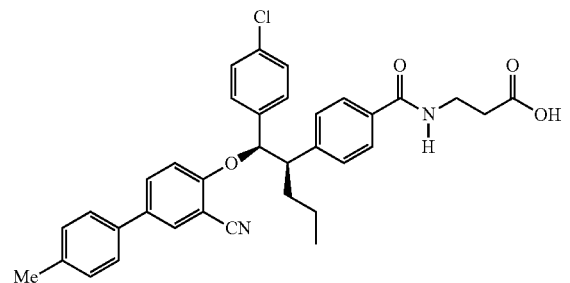 [SMILES: CCC[C@H](c1ccc(C(=O)NCCC(=O)O)cc1)[C@@H](Oc1ccc(-c2ccc(C)cc2)cc1C#N)c1ccc(Cl)cc1]

Step A. 4-{(1R)-1-[(R)-(4-Bromo-2-cyanophenoxy)(4-chlorophenyl)methyl]butyl}benzoic acid

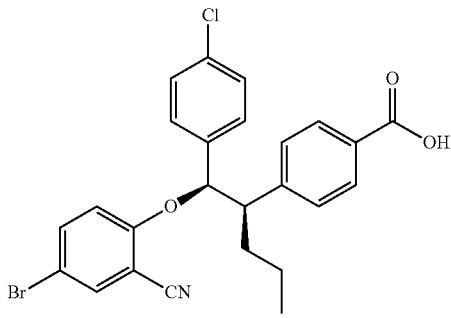 [SMILES: CCC[C@H](c1ccc(C(=O)O)cc1)[C@@H](Oc1ccc(Br)cc1C#N)c1ccc(Cl)cc1]

To a solution of 4-{(1R)-1-[(R)-(4-chlorophenyl)(hydroxy)methyl]butyl}benzoic acid (INTERMEDIATE 1, Step C, 1.00 g, 3.14 mmol) and potassium benzoate (1.01 mg, 6.27 mmol) in DMSO was added NaH (60 wt % in mineral oil, 251 mg, 6.27 mmol). After 30 minutes, 5-bromo-2-fluorobenzonitrile (816 mg, 4.08 mmol) was added, then the mixture was stirred at 80° C. for 3-6 hours. After cooling to RT, the mixture was diluted with EtOAc and 2 N HCl (aq). The organic layer was washed with brine, dried over anhydrous MgSO$_4$, filtered, then concentrated. This afforded the title compound which was used directly for the next step without further purification. LC2 2.34 min. (M+H)$^+$ 498.

Step B. Ethyl N-(4-{(1R)-1-[(R)-(4-bromo-2-cyanophenoxy)(4-chlorophenyl)methyl]butyl}benzoyl)-β-alaninate

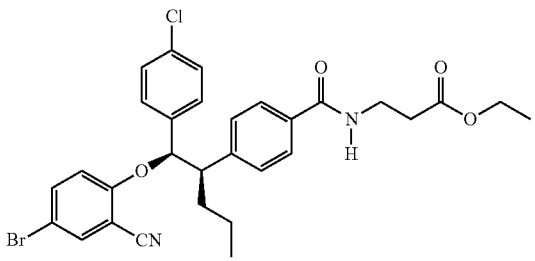 [SMILES: CCC[C@H](c1ccc(C(=O)NCCC(=O)OCC)cc1)[C@@H](Oc1ccc(Br)cc1C#N)c1ccc(Cl)cc1]

The product from step A was dissolved in THF (10 mL) then CDI (1.018 g, 6.28 mmol) was added. After being stirred for one hour, β-alanine ethyl ester hydrochloride (560 mg, 6.28 mmol) was added, then the mixture was stirred overnight at RT. The mixture was diluted with EtOAc then washed with water then brine. The organic layer was dried over MgSO$_4$, filtered, then concentrated. The resulting residue was purified by silica gel chromatography to afford the title compound. $^1$H NMR (500 MHz, CD$_3$OD): δ 7.72 (d, J=2.5 Hz, 1H); 7.67 (d, J=8.5 Hz, 2H); 7.50 (dd, J=9.0, 2.5 Hz, 1H); 7.37 (d, J=8.0 Hz, 2H); 7.24 (d, J=8.0 Hz, 2H); 7.13 (d, J=8.5 Hz, 2H); 6.81 (d, J=9.5 Hz, 1H); 5.63 (d, J=6.0 Hz, 1H); 4.12 (q, J=7.5 Hz, 2H); 3.61 (t, J=7.0 Hz, 2H); 3.19 (m, 1H); 2.62 (t, J=7.0 Hz, 2H); 2.00-1.94 (m, 1H); 1.73-1.67 (m, 1H); 1.22 (t, J=7.5 Hz, 3H); 1.19-1.16 (m, 2H); 0.83 (t, J=7.0 Hz, 3H). LC2 2.38 min. (M+H)$^+$ 597.

Step C. N-[4-((1R)-1-{(R)-(4-Chlorophenyl)[(3-cyano-4'-methylbiphenyl-4-yl)oxy]methyl}butyl)benzoyl]-β-alanine

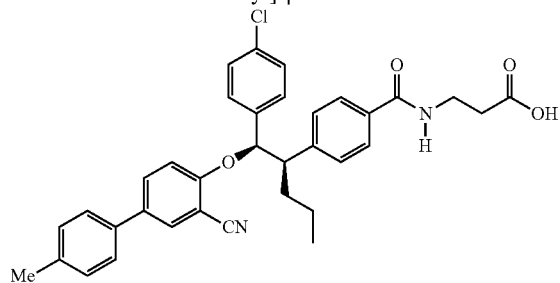

To a solution of the product from Step B (960 mg, 1.61 mmol) in THF (10 mL) and EtOH (10 mL) was added LiOH (2.0 M in H$_2$O, 8.0 mL, 16.0 mmol). After being stirred at RT for 45 minutes, all the ester starting material had been consumed by LC-MS analysis. The mixture was diluted with DCM and 2 N HCl(aq). The organic layer was concentrated to afford the acid intermediate which was used directly in the next step without further purification.

A solution of the acid from the previous step (50 mg, 0.088 mmol) in DMF was added to a mixture of Na$_2$CO$_3$ (2.0 M in H$_2$O, 0.132 mL, 0.263 mmol), Pd(PPh$_3$)$_4$ (10.1 mg, 8.77 µmol) and (4-methylphenyl)boronic acid (23.9 mg, 0.175 mmol), then the mixture was stirred at 60° C. overnight. After being allowed to cool to RT, the mixture was purified by preparative reverse phase HPLC eluting with 50-100% MeCN/water+0.1% TFA. Following lyophilization, this afforded the title compound. $^1$H NMR (500 MHz, CD$_3$OD): δ 7.76 (d, J=2.0 Hz, 1H); 7.68 (d, J=8.5 Hz, 2H); 7.60 (dd, J=9.0, 2.5 Hz, 1H); 7.39 (d, J=8.0 Hz, 2H); 7.37 (dd, J=10.5, 2.0 Hz, 2H); 7.24 (d, J=8.0 Hz, 2H); 7.19 (d, J=8.0 Hz, 2H); 7.15 (d, J=8.5 Hz, 2H); 6.91 (d, J=9.0 Hz, 1H); 5.66 (d, J=5.5 Hz, 1H); 3.60 (t, 3-7.0 Hz, 2H); 3.23-3.19 (m, 1H); 2.62 (t, J=7.0 Hz, 2H); 2.32 (s, 3H); 2.02-1.97 (m, 1H); 1.79-1.72 (m, 1H); 1.23-1.16 (m, 2H); 0.85 (t, J=7.5 Hz, 3H); LC1 1.28 min. (M+H)$^+$ 581.

Using the chemistry described for the preparation of INTERMEDIATES 1 and 2 and in EXAMPLES 1-4, the compounds in TABLES 1-3 were prepared as enantiopure compounds.

TABLE 1

| EXAMPLE | R$^3$ | LC-MS Data |
|---|---|---|
| 5 | 3,5-di-tert-butylphenyl | LC1: 1.28 min. (M + H) 578 |
| 6 | 3,4-dichlorophenyl | LC1: 1.25 min. (M + H) 536 |
| 7 | 2,4-dichlorophenyl | LC1: 1.24 min. (M + H) 536 |
| 8 | 3,5-dimethylphenyl | LC1: 1.25 min. (M + H) 494 |
| 9 | 4-cyanonaphth-1-yl | LC1: 1.24 min. (M + H) 541 |
| 10 | 4-(trifluoromethyl)naphth-1-yl | LC1: 1.29 min. (M + H) 585 |

TABLE 1-continued

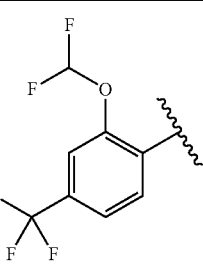

| EX-AMPLE | R³ | LC-MS Data |
|---|---|---|
| 11 | 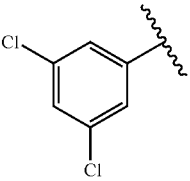 [SMILES: *c1cc(Cl)cc(Cl)c1] | LC3: 4.02 min. (M + H) 600 |

¹H NMR (500 MHz, CD₃OD): δ 7.70 (d, J = 8.0 Hz, 2 H); 7.35 (d, J = 7.5 Hz, 2 H); 7.34 (s, 1 H); 7.29 (d, J = 9.0 Hz, 1 H); 7.25 (d, J = 8.5 Hz, 2 H); 7.18 (d, J = 8.5 Hz, 2 H); 6.96 (d, J= 9.0 Hz, 1 H); 6.50 (t, J = 7.5 Hz, 1 H); 5.64 (d, J = 6.0 Hz, 1 H); 3.61-3.59 (m, 2 H); 3.19 (m, 1 H); 2.62 (m, 2 H); 1.90-1.85 (m, 1 H); 1.67-1.62 (m, 1 H); 1.16-1.11 (m, 2 H); 0.79 (t, J = 7.2 Hz, 3 H).

| 12 | 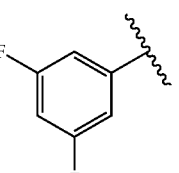 | LC3: 4.17 min. (M + H) 536 |

¹H NMR (500 MHz, CD₃OD): δ 7.71 (d, J = 8.5 Hz, 2 H); 7.32 (d, J= 8.5 Hz, 2 H); 7.28 (d, J = 8.5 Hz, 2 H); 7.21 (d, J = 8.5 Hz, 2 H); 6.88 (d, J = 1.5 Hz, 1 H); 6.74 (d, J = 1.5 Hz, 2 H); 5.48 (d, J = 7.0 Hz, 1 H); 3.60 (t, J= 7.0 Hz, 2 H); 3.16 (m, 1 H); 2.64 (t, J = 7.0 Hz, 2 H); 1.87-1.79 (m, 1 H); 1.61-1.54 (m, 1 H); 1.17-1.07 (m, 2 H); 0.81 (t, J = 7.3 Hz, 3 H).

| 13 | 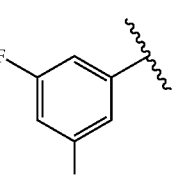 | LC3: 3.92 min. (M + H) 502 |

| 14 | 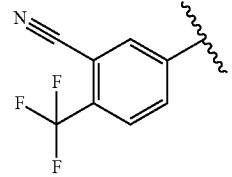 [SMILES: *c1ccc(C(F)(F)F)c(C#N)c1] | LC3: 4.05 min. (M + H) 518 |

TABLE 1-continued

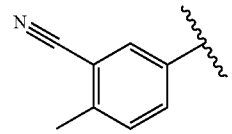 [SMILES: *c1ccc(C)c(C#N)c1]

| EX-AMPLE | R³ | LC-MS Data |
|---|---|---|
| 15 | 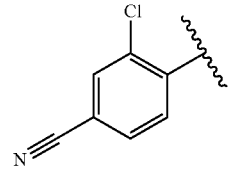 [SMILES: *c1ccc(C#N)cc1Cl] | LC3: 3.93 min. (M + H) 559 |

¹H NMR (500 MHz, CD₃OD): δ 7.70 (d, J = 8.5 Hz, 2 H); 7.62 (d, J = 8.5 Hz, 1 H); 7.36 (d, J = 2.5 Hz, 1 H); 7.34 (d, J = 8.5 Hz, 2 H); 7.30 (d, J = 8.5 Hz, 2 H); 7.25 (d, J = 8.5 Hz, 2 H); 7.17 (dd, J= 8.5, 2.0 Hz, 1 H); 5.64 (d, J = 7.0 Hz, 1 H); 3.60 (m, 2 H); 3.20 (m, 1 H); 2.61 (t, 2 H); 1.86-1.78 (m, 1 H); 1.59-1.53 (m, 1 H); 1.16-1.07 (m, 2 H); 0.80 (t, J = 7.2 Hz, 3 H).

| 16 | 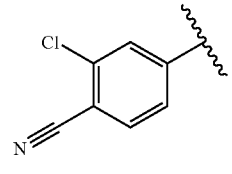 [SMILES: *c1ccc(C#N)c(Cl)c1] | LC3: 3.84 min. (M + H) 505 |

¹H NMR (500 MHz, CD₃OD): δ 7.69 (d, J = 8.5 Hz, 2 H); 7.32 (d, J = 8.0 Hz, 2 H); 7.26 (d, J= 8.5 Hz, 2 H); 7.20 (d, J = 8.5 Hz, 2 H); 7.12 (d, J = 8.5 Hz, 1 H); 6.98 (d, J = 2.5 Hz, 1 H); 6.93 (dd, J = 8.5, 2.5 Hz, 1 H); 5.44 (d, J = 7.0 Hz, 1 H); 3.60 (m, 2 H); 3.10 (m, 1 H); 2.62 (m, 2 H); 1.83-1.17 (m, 1 H); 1.60-1.53 (m, 1 H); 1.13-1.06 (m, 2 H); 0.80-0.77 (t, J = 7.2 Hz, 3 H).

| 17 | Cl, CN aryl | LC3: 3.84 min. (M + H) 525 |

¹H NMR (500 MHz, CD₃OD): δ 7.72 (d, J = 1.5 Hz, 1 H); 7.67 (d, J = 8.5 Hz, 2 H); 7.42 (dd, J = 9.0, 2.0 Hz, 1 H); 7.36 (d, J= 8.0 Hz, 2 H); 7.23 (d, J = 8.5 Hz, 2 H); 7.12 (d, J= 8.0 Hz, 2 H); 6.93 (d, J = 9.0 Hz, 1 H); 5.70 (d, J = 5.5 Hz, 1 H); 3.65 (m, 2 H); 3.21 (m, 1 H); 2.59 (m, 2 H); 1.97-1.91 (m, 1 H); 1.74-1.68 (m, 1 H); 1.21-1.13 (m, 2 H); 0.83 (t, J = 7.3 Hz, 3 H).

| 18 | Cl, CN aryl | LC3: 3.63 min. (M + H) 525 |

TABLE 1-continued

| EXAMPLE | R³ | LC-MS Data |
|---|---|---|
| 19 | 2-chloro-5-(cyano) phenyl | LC3: 3.92 min. (M + H) 525 |

¹H NMR (500 MHz, CD₃OD): δ 7.71 (d, J = 8.0 Hz, 2 H); 7.34 (d, J = 9.0 Hz, 2 H); 7.33 (s, 1 H); 7.29 (d, J = 8.5 Hz, 2 H); 7.23 (d, J = 8.5 Hz, 2H); 7.17 (d, J = 3.0 Hz, 1 H); 7.04 (dd, J = 9.0, 3.0 Hz, 1 H); 5.51 (d, J = 7.0 Hz, 1 H); 3.61 (m, 2 H); 3.17 (m, 1 H); 2.62 (m, 2 H); 1.85-1.77 (m, 1 H); 1.59-1.52 (m, 1 H); 1.15-1.06 (m, 2 H); 0.79 (t, J = 7.2 Hz, 3 H).

| EXAMPLE | R³ | LC-MS Data |
|---|---|---|
| 20 | 2-cyano-3-(trifluoromethyl) phenyl | LC3: 3.82 min. (M + H) 559 |
| 21 | 2,5-dichlorophenyl | LC3: 3.86 min. (M + H) 525 |
| 22 | 2-chloro-6-(cyano) phenyl | LC3: 3.84 min. (M + H) 525 |
| 23 | 3-cyano-5-methoxyphenyl | LC3: 3.57 min. (M + H) 521 |
| 24 | 2-fluoro-3-chloro-5-(trifluoromethyl) phenyl | LC3: 3.89 min. (M + H) 586 |
| 25 | 2-methoxy-4-(trifluoromethyl) phenyl | LC3: 3.74 min. (M + H) 564 |
| 26 | 2-chloro-4-(trifluoromethyl) phenyl | LC3: 4.10 min. (M + H) 567 |
| 27 | 2-cyano-4-chlorophenyl | LC3: 3.85 min. (M + H) 523 |
| 28 | 2-cyano-3-chlorophenyl | LC3: 3.90 min. (M + H) 523 |
| 29 | 3-methoxy-5-(trifluoromethyl) phenyl | LC3: 4.03 min. (M + H) 564 |

TABLE 1-continued
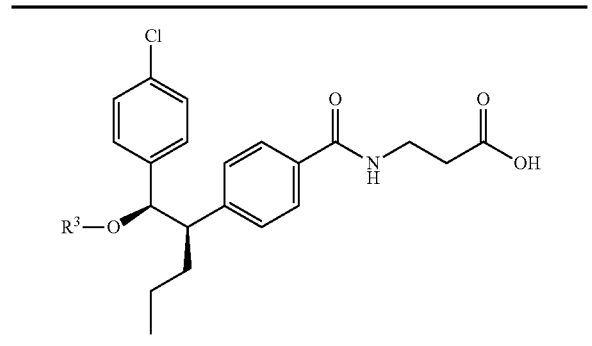
| EXAMPLE | R³ | LC-MS Data |
|---|---|---|
| 30 | 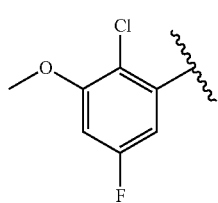 [SMILES: *c1cc(F)cc(OC)c1Cl] | LC3: 4.10 min. (M + H) 547 |
| 31 | 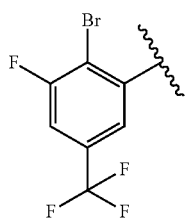 | LC3: 3.89 min. (M + H) 632 |
| 32 | 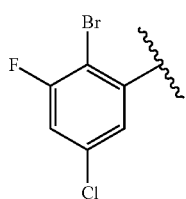 [SMILES: *c1cc(Cl)cc(F)c1Br] | LC3: 3.87 min. (M + H) 597 |
| 33 | 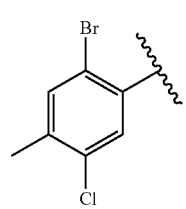 [SMILES: *c1cc(Cl)c(C)cc1Br] | LC3: 4.08 min. (M + H) 594 |
TABLE 1-continued
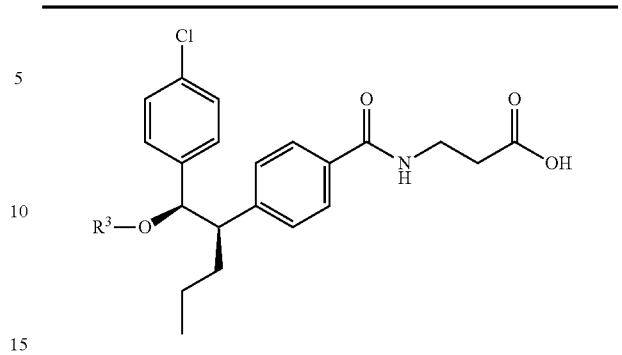
| EXAMPLE | R³ | LC-MS Data |
|---|---|---|
| 34 | 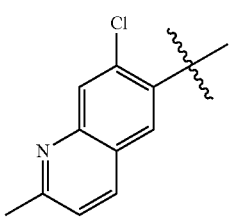 [SMILES: *c1cc2ccc(C)nc2cc1Cl] | LC2: 2.10 min. (M + H) 565 |
| 35 | 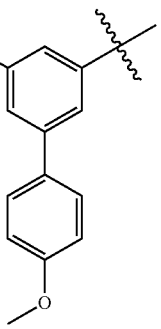 | LC3: 4.08 min. (M + H) 597 |
| 36 | 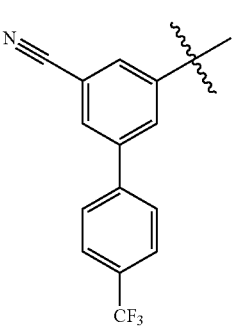 [SMILES: *c1cc(C#N)cc(-c2ccc(C(F)(F)F)cc2)c1] | LC3: 3.91 min. (M + H) 635 |

TABLE 2
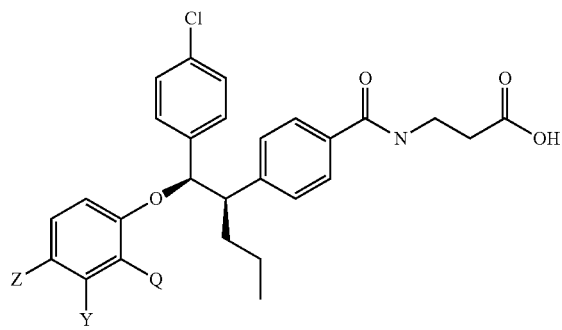
| EXAMPLE | Q | Y | Z | LC-MS Data |
|---|---|---|---|---|
| 37 | H | —CN | 4-OCF₃-phenyl | LC1: 1.30 min. (M + H) 652 |
| 38 | H | —CN | 4-OMe-phenyl | LC1: 1.27 min. (M + H) 597 |
| 39 | H | —CN | 4-CF₃-phenyl | LC1: 1.30 min. (M + H) 635 |
| 40 | H | —CN | 6-OMe-pyridin-3-yl | LC2: 1.25 min. (M + H) 598 |
| 41 | H | —CN | 3-F-5-OMe-phenyl | LC2: 1.26 min. (M + H) 615 |
TABLE 2-continued
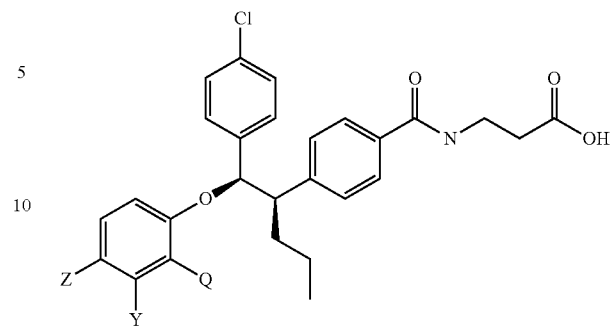
| EXAMPLE | Q | Y | Z | LC-MS Data |
|---|---|---|---|---|
| 42 | H | H | 4-OCF₃-phenyl | LC1: 1.29 min. (M + H) 626 |
| 43 | H | H | 4-OMe-phenyl | LC1: 1.33 min. (M + H) 573 |
| 44 | H | H | 4-CF₃-phenyl | LC1: 1.28 min. (M + H) 610 |
| 45 | H | H | 3-F-5-OMe-phenyl | LC1: 1.26 min. (M + H) 590 |
| 46 | H | H | 4-Me-phenyl | LC1: 1.38 min. (M + H) 556 |

TABLE 2-continued

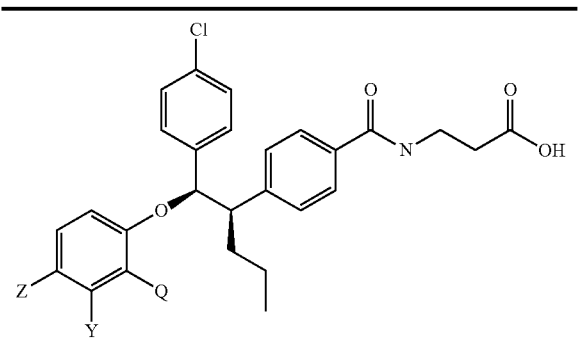

| EXAMPLE | Q | Y | Z | LC-MS Data |
|---|---|---|---|---|
| 47 | H | H | 1-methylpyrrol-2-yl | LC1: 1.31 min. (M + H) 545 |
| 48 | H | —CN | 2-fluoro-4-(trifluoromethyl)phenyl | LC1: 1.30 min. (M + H) 653 |
| 49 | H | —CN | 4-isopropoxyphenyl | LC1: 1.29 min. (M + H) 625 |
| 50 | H | —CN | 4-methylphenyl | LC1: 1.27 min. (M + H) 581 |
| 51 | H | —CN | 4-methoxy-3-methylphenyl | LC1: 1.27 min. (M + H) 611 |

TABLE 2-continued

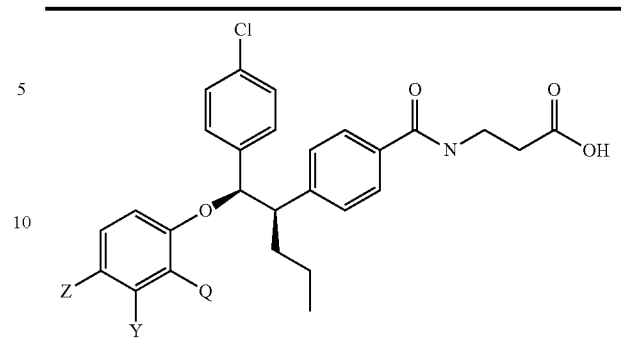

| EXAMPLE | Q | Y | Z | LC-MS Data |
|---|---|---|---|---|
| 52 | —CN | H | 4-methoxyphenyl | LC1: 1.28 min (M + H) 597 |
| 53 | —CN | H | 4-methylphenyl | LC1: 1.26 min (M + H) 581 |
| 54 | —CN | H | 4-(trifluoromethoxy)phenyl | LC1: 1.32 min (M + H) 651 |
| 55 | —CN | H | 2-fluoro-4-(trifluoromethyl)phenyl | LC1: 1.31 min (M + H) 653 |
| 56 | —CN | H | 6-methoxypyridin-3-yl | LC1: 1.28 min (M + H) 598 |

TABLE 2-continued
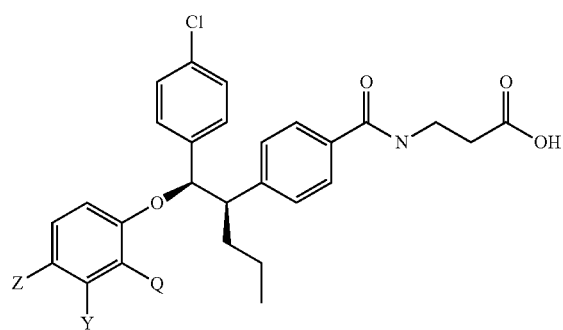
| EXAMPLE | Q | Y | Z | LC-MS Data |
|---|---|---|---|---|
| 57 | —CN | H | 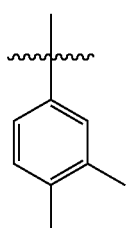 [SMILES: *c1ccc(C)c(C)c1] | LC1: 1.30 min (M + H) 595 |
| 58 | —CN | H | 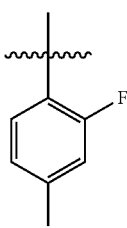 [SMILES: *c1ccc(C)cc1F] | LC1: 1.28 min (M + H) 599 |
| 59 | —CN | H | 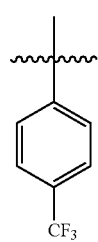 | LC1: 1.27 min (M + H) 635 |
| 60 | H | —CN | 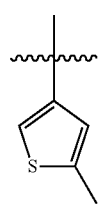 [SMILES: *c1csc(C)c1] | LC1: 1.26 min (M + H) 587 |
| 61 | H | —CN | 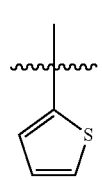 [SMILES: *c1cccs1] | LC1: 1.25 min (M + H) 573 |
TABLE 3
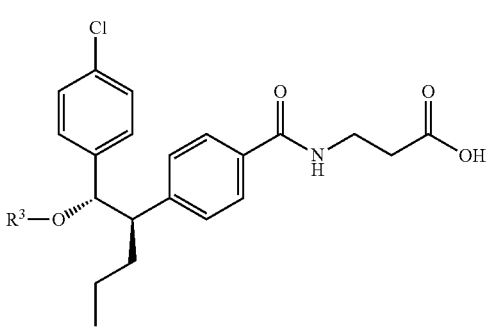
| EXAMPLE | R³ | LC-MS Data |
|---|---|---|
| 62 | 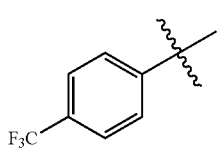 [SMILES: *c1ccc(C(F)(F)F)cc1] | LC2: 2.59 min. (M + H) 534 |
| 63 | 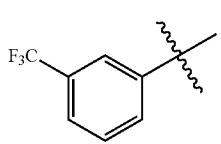 [SMILES: *c1cccc(C(F)(F)F)c1] | LC2: 2.70 min. (M + H) 534 |
| 64 | 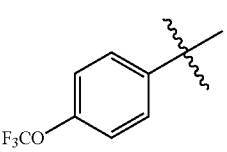 [SMILES: *c1ccc(OC(F)(F)F)cc1] | LC2: 2.62 min. (M + H) 550 |
| 65 | 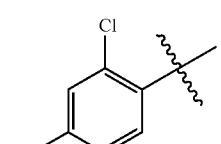 | LC3: 4.20 min. (M + H) 568 |
| 66 | 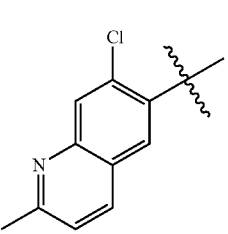 [SMILES: *c1cc2ccc(C)nc2cc1Cl] | LC3: 3.80 min. (M + H) 565 |

Example 67

N-(4-{(1R)-1-[(R)-[(6-chloro-8-methylquinolin-4-yl)oxy](4-chlorophenyl)methyl]butyl}benzoyl)-β-alanine

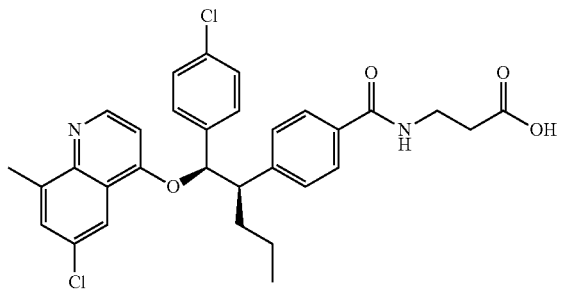 [SMILES: CCC[C@H](c1ccc(C(=O)NCCC(=O)O)cc1)[C@@H](Oc1ccnc2c(C)cc(Cl)cc12)c1ccc(Cl)cc1]

Step A. tert-Butyl 4-{(1R)-1-[(S)-bromo(4-chlorophenyl)methyl]butyl}benzoate

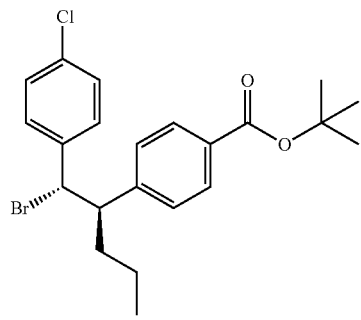 [SMILES: CCC[C@H](c1ccc(C(=O)OC(C)(C)C)cc1)[C@H](Br)c1ccc(Cl)cc1]

A solution of triphenylphosphine (2.80 g, 10.7 mmol) in DCM (10 mL) was added over 30 minutes to a solution of tert-butyl 4-{(1R)-1-[(R)-(4-chlorophenyl)(hydroxy)methyl]butyl}benzoate (INTERMEDIATE 1, Step 13, 2.00 g, 5.33 mmol) and carbon tetrabromide (2.48 g, 7.47 mmol) in DCM (15 mL) at 0° C. Once the addition was complete, the solution was stirred at 5-10° C. for an additional 30 minutes, then most of the solvent was removed by rotary evaporation. Hexanes (10 mL) was added to the resulting solution with vigorous stirring. The resulting white precipitate was removed by filtration, then the filtrate was concentrated. The resulting residue was purified by silica gel chromatography eluting with 0-20% EtOAc/hexanes to afford the title compound as a crystalline yellow solid. $^1$H NMR (500 MHz, CDCl$_3$): δ 7.76 (d, J=8 Hz, 2H); 7.11 (d, J=8.5 Hz, 2H); 7.08 (d, J=8.5 Hz, 2H); 6.99 (d, J=8.5 Hz, 2H); 5.06 (d, J=10 Hz, 1H); 3.35-3.29 (m, 1H); 2.37-2.29 (m, 1H); 1.76-1.66 (m, 1H); 1.55 (s, 9H); 1.14-1.04 (m, 2H); 0.86 (t, J=7.5 Hz, 3H); LC4 2.90 min. (M+H)$^+$ 381, 383.

Step B. tert-Butyl 4-{(1R)-1-[(R)-[(6-chloro-8-methylquinolin-4-yl)oxy](4-chlorophenyl)methyl]butyl}benzoate

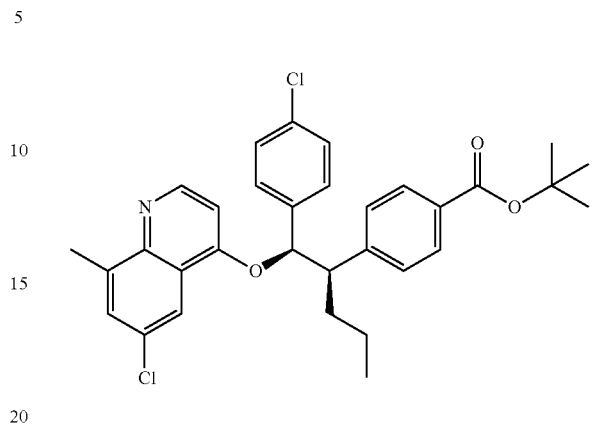

Sodium hydride (60 wt % in mineral oil, 15.5 mg, 0.387 mmol) was washed with hexanes (2 mL), then a solution of 6-chloro-8-methylquinolin-4-ol (50.0 mg, 0.258 mmol) in DMF (2 mL) was added. Once gas evolution had ceased, the product of Step A (170 mg, 0.387 mmol) was added in one portion, then the mixture was stirred at 120° C. overnight. After being allowed to cool to room temperature, the mixture was diluted with EtOAc (20 mL) and water (15 mL), then the organic layer was concentrated. The resulting residue was purified by silica gel chromatography eluting with 0-100% EtOAc/hexanes to afford the title compound. $^1$H NMR (500 MHz, CDCl$_3$): δ 8.51 (d, J=5 Hz, 1H); 7.93 (d, J=8.5 Hz, 2H); 7.89 (d, J=2.5 Hz, 1H); 7.47 (s, 1H); 7.26 (dd, J=6.5, 6.0 Hz, 4H); 7.12 (d, J=8.5 Hz, 2H); 6.43 (d, J=5 Hz, 1H); 5.44 (d, J=6.5 Hz, 1H); 3.29-3.23 (m, 1H); 2.69 (s, 3H); 1.90-1.80 (m, 1H); 1.74-1.64 (m, 1H); 1.58 (s, 9H); 1.30-1.10 (m, 2H); 0.83 (t, J=7.5 Hz, 3H); LC4 2.78 min. (M+H)$^+$ 550.

Step C. N-(4-{(1R)-1-[(R)-[(6-chloro-8-methylquinolin-4-yl)oxy](4-chlorophenyl)methyl]butyl}benzoyl)-β-alanine

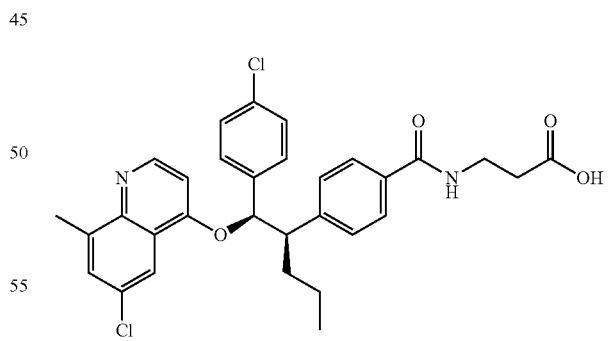

The product from Step B (11 mg, 0.020 mmol) was dissolved in DCM (0.5 mL) then TFA (0.5 mL, 6.49 mmol) was added. After being stirred at room temperature for one hour, the solution was concentrated to afford the carboxylic acid which was used directly in the next step. LC4 2.32 min. (M+H)$^+$ 494.

To a solution of the product from the previous step (10 mg, 0.020 mmol) and DIEA (0.021 mL, 0.12 mmol) in DCM (1 mL) were added PyBOP (12 mg, 0.024 mmol) and tert-butyl β-alaninate hydrochloride (4.4 mg, 0.024 mmol). After being stirred at room temperature for one hour, the mixture was diluted with DCM (5 mL) and 1 N HCl(aq) (5 mL). The organic layer was dried over anhydrous $Na_2SO_4$, filtered, then concentrated to afford the amide product which was used directly in the next step. LC4 2.49 min. (M+H)$^+$ 621.

The product from the previous step (12 mg, 0.020 mmol) was dissolved in DCM (0.5 mL) then TFA (0.5 mL, 6.49 mmol) was added. After being stirred at room temperature for one hour, the solution was concentrated. The resulting residue was purified by reverse phase HPLC eluting with acetonitrile/water+0.1% TFA. Following lyophilization, this afforded the title compound as a fluffy, white solid. $^1$H NMR (500 MHz, CDCl$_3$): δ 8.84 (d, J=6.5 Hz, 1H); 7.91 (d, J=2 Hz, 1H); 7.67 (d, J=8.0 Hz, 2H); 7.63 (s, 1H); 7.40 (s, 4H); 7.36 (d, J=8.5 Hz, 2H); 7.01 (t, J=6.0 Hz, 1H); 6.99 (d, J=7 Hz, 1H); 5.67 (d, J=9 Hz, 1H); 3.66-3.53 (m, 2H); 3.41-3.34 (m, 1H); 2.73 (s, 3H); 2.56 (t, J=6.0 Hz, 2H); 1.79-1.69 (m, 1H); 1.45-1.37 (m, 1H); 1.20-1.10 (m, 1H); 1.10-1.00 (m, 1H); 0.77 (t, J=7 Hz, 3H); LC4 2.11 min. (M+H)$^+$ 565.

Example 68

N-[4-((1R)-1-{(R)-(4-chlorophenyl)[(7-methylquinolin-4-yl)oxy]methyl}butyl)benzoyl]-β-alanine

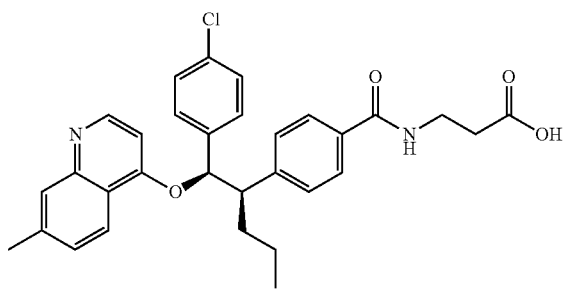 [SMILES: CCC[C@H](c1ccc(C(=O)NCCC(=O)O)cc1)[C@@H](Oc1ccnc2cc(C)ccc12)c1ccc(Cl)cc1]

Using the procedure from EXAMPLE 67, 7-methylquinolin-4-ol was converted to the title compound. $^1$H NMR (500 MHz, CDCl$_3$): δ 8.12 (d, J=8.5 Hz, 1H); 8.03 (d, J=8.5 Hz, 1H); 7.78 (t, J=8.0 Hz, 1H); 7.63 (d, J=8.0 Hz, 2H); 7.60 (t, J=7.5 Hz, 1H); 7.43 (s, 4H); 7.33 (d, J=7.5 Hz, 2H); 7.03 (br, 1H); 6.50 (s, 1H); 5.60 (d, J=9 Hz, 1H); 3.60-3.45 (m, 2H); 3.37-3.30 (m, 1H); 2.70 (s, 3H); 2.47 (br, 2H); 1.78-1.68 (m, 1H); 1.44-1.34 (m, 1H); 1.20-1.10 (m, 1H); 1.10-1.00 (m, 1H); 0.77 (t, J=7.5 Hz, 3H); LC4 1.81 min. (M+H)$^+$ 531.

Example 69

N-[4-((1R)-1-{(R)-(4-chlorophenyl)[(7-chloroquinolin-4-yl)oxy]methyl}butyl)benzoyl]-β-alanine

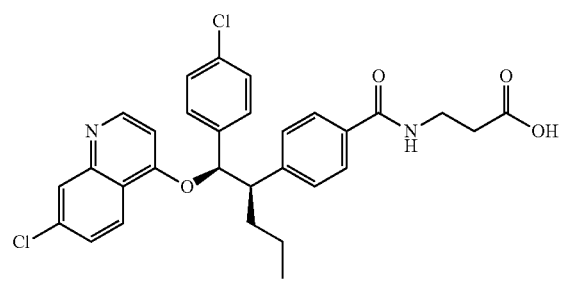 [SMILES: CCC[C@H](c1ccc(C(=O)NCCC(=O)O)cc1)[C@@H](Oc1ccnc2cc(Cl)ccc12)c1ccc(Cl)cc1]

Using the procedure from EXAMPLE 67, 7-chloroquinolin-4-ol was converted to the title compound. $^1$H NMR (500 MHz, CDCl$_3$): δ 8.74 (d, J=6.5 Hz, 1H); 8.17 (s, 1H); 8.04 (d, J=9.0 Hz, 1H); 7.67 (d, 0.1=8.0 Hz, 2H); 7.59 (dd, J=9, 1.5 Hz, 1H); 7.38 (dd, 8.0, 8.5 Hz, 4H); 7.34 (d, J=8 Hz, 2H); 6.98 (t, J=6 Hz, 1H); 6.80 (d, J=6.5 Hz, 1H); 5.64 (d, J=9 Hz, 1H); 3.70-3.51 (m, 2H); 3.39-3.32 (m, 1H); 2.58 (t, J=6 Hz, 2H); 1.79-1.69 (m, 1H); 1.48-1.39 (m, 1H); 1.20-1.10 (m, 1H); 1.10-1.00 (m, 1H); 0.77 (t, J=7.5 Hz, 3H); LC4 1.81 min. (M+H)$^+$ 551.

Example 70

N-(4-{(1R)-1-[(R)-[(2-trifluoromethylquinolin-4-yl)oxy](4-chlorophenyl)methyl]butyl}benzoyl)-β-alanine

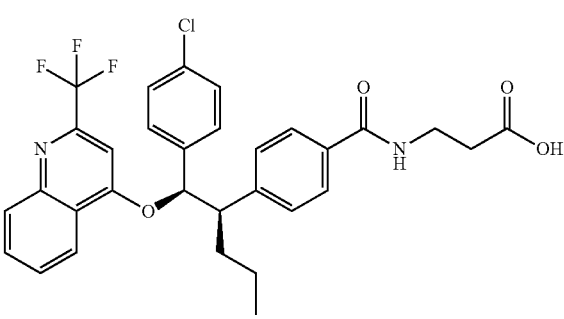 [SMILES: CCC[C@H](c1ccc(C(=O)NCCC(=O)O)cc1)[C@@H](Oc1cc(C(F)(F)F)nc2ccccc12)c1ccc(Cl)cc1]

Step A. tert-Butyl 4-{(1R)-1-[(R)-[(2-trifluoromethylquinolin-4-yl)oxy](4-chlorophenyl)methyl]butyl}benzoate

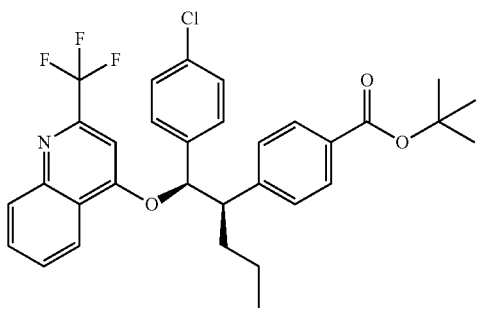 [SMILES: CCC[C@H](c1ccc(C(=O)OC(C)(C)C)cc1)[C@@H](Oc1cc(C(F)(F)F)nc2ccccc12)c1ccc(Cl)cc1]

Sodium hydride (60 wt % in mineral oil, 6.5 mg, 0.27 mmol) was added to a solution of tert-butyl 4-{(1R)-1-[(R)-(4-chlorophenyl)(hydroxy)methyl]butyl}benzoate (INTERMEDIATE 1, Step B, 100 mg, 0.267 mmol) in DMA (1.0 mL) in a microwave vial. Once gas evolution had ceased, 4-bromo-2-(trifluoromethyl)quinoline (147 mg, 0.533 mmol) was added. The vial was sealed, then the mixture was heated in a microwave reactor at 120° C. for ten minutes. After being allowed to cool to RT, the mixture was diluted with EtOAc (10 mL) and water (10 mL). The organic phase was concentrated, and the residue was purified by silica gel chromatography eluting with 0-100% EtOAc/hexanes to afford the title compound as an amorphous, white solid. $^1$H NMR (500 MHz, CDCl$_3$): δ 8.18 (d, J=8.5 Hz, 1H); 8.08 (d, 8.5, 1H); 7.92 (d, J=8.0 Hz, 2 FI); 7.77 (t, J=7.0 Hz, 1H); 7.62 (t, J=7.5 Hz, 1H); 7.28 (t, J=9 Hz, 4H); 7.15 (d, J=8.5 Hz, 2H); 6.75 (s, 1H); 5.55 (d, J=6.5 Hz, 1H); 3.32-326 (m, 1H); 1.92-1.82 (m, 1H); 1.74-1.64 (m, 1H); 1.58 (s, 9H); 1.25-1.10 (m, 2H); 0.83 (t, J=7.5 Hz, 3H); LC4 3.10 min. (M+H)$^+$ 570.

Step B. N-(4-{(1R)-1-[(R)-[(2-trifluoromethylquinolin-4-yl)oxy](4-chlorophenyl)methyl]butyl}benzoyl)-β-alanine

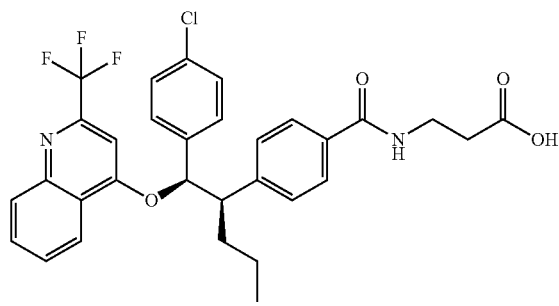 [SMILES: CCC[C@H](c1ccc(C(=O)NCCC(=O)O)cc1)[C@@H](Oc1cc(C(F)(F)F)nc2ccccc12)c1ccc(Cl)cc1]

Using the procedure from EXAMPLE 67, Step C, the product of Step A was converted to the title compound. $^1$H NMR (500 MHz, CDCl$_3$): δ 8.16 (d, J=8.5 Hz, 1H); 8.08 (d, J=9 Hz, 1H); 7.76 (t, J=6.0 Hz, 1H); 7.70 (d, J=8.5 Hz, 2H); 7.61 (t, J=7.5 Hz, 1H); 7.31 (d, J=8.5 Hz, 2H); 7.27 (d, J=8.5 Hz, 2H); 7.15 (d, J=8.5 Hz, 2H); 6.75 (s, 1H); 6.73 (t, J=6.0 Hz, 1H); 5.54 (d, J=6.5 Hz, 1H); 3.72 (q, J=6.0 Hz, 2H); 3.32-3.26 (m, 1H); 2.72 (q, J=6.0 Hz, 2H); 1.91-1.81 (m, 1H); 1.76-1.64 (m, 1H); 1.26-1.08 (m, 2H); 0.82 (t, J=7.5 Hz, 3H); LC4 2.47 min. (M+H)$^+$ 585.

Example 71

N-[4-((1R)-1-{(R)-(4-chlorophenyl)[(7-cyanoquinolin-4-yl)oxy]methyl}butyl)benzoyl]-β-alanine

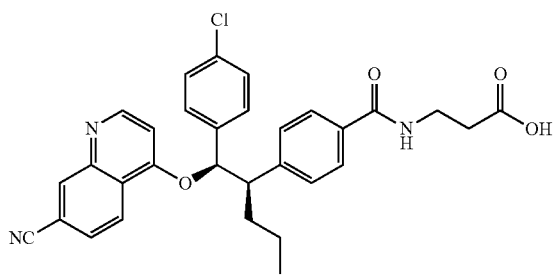 [SMILES: CCC[C@H](c1ccc(C(=O)NCCC(=O)O)cc1)[C@@H](Oc1ccnc2cc(C#N)ccc12)c1ccc(Cl)cc1]

Using the procedure from EXAMPLE 70, 4-bromo-7-cyanoquinoline was converted to the title compound. $^1$H NMR (500 MHz, CDCl$_3$): δ 8.82 (d, J=6.0 Hz, 1H); 8.55 (s, 1H); 8.18 (d, J=8.5 Hz, 1H); 7.78 (d, J=8.5 Hz, 1H); 7.68 (d, J=8.0 Hz, 2H); 7.39 (d, J=8.5 Hz, 2H); 7.35-7.29 (q, J=8.0 Hz, 4H); 6.84 (t, J=6.5 Hz, 1H); 6.79 (d, J=6.0 Hz, 1H); 5.57 (d, J=8.5 Hz, 1H); 3.72-3.62 (m, 2H); 3.40-3.32 (m, 1H); 2.66 (t, J=5.5 Hz, 2H); 1.82-1.72 (m, 1H); 1.56-1.46 (m, 1H); 1.24-1.04 (m, 2H); 0.80 (t, J=7.5 Hz, 3H); LC4 2.47 min. (M+H)$^+$ 540.

Example 72

N-{4-[(1R)-1-((R)-(4-chlorophenyl){[4-(trifluoromethoxy)benzyl]oxy}methyl)butyl]benzoyl}-β-alanine

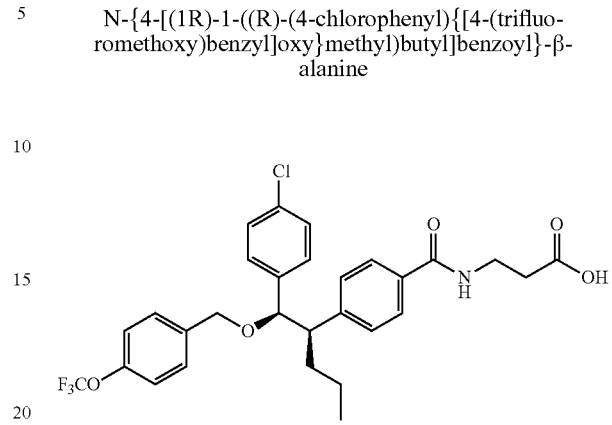

Step A. tert-butyl 4-[(1R)-1-((R)-(4-chlorophenyl){[4-(trifluoromethoxy)benzyl]oxy}methyl)butyl]benzoate Potassium hydroxide (84 mg, 0.75 mmol) was added to a solution of tert-butyl 4-{(1R)-1-[(R)-(4-chlorophenyl)(hydroxy)methyl]butyl}benzoate (INTERMEDIATE 1, Step B, 200 mg, 0.533 mmol) in THF (5.0 mL), then the mixture was stirred for five minutes. Then 1-(bromomethyl)-4-(trifluoromethoxy)benzene (163 mg, 0.640 mmol) was added, and the mixture was stirred at RT overnight. The mixture was diluted with EtOAc and water, then the organic layer was concentrated. The resulting residue was purified by silica gel chromatography eluting with 10-50% EtOAc/hexanes to afford the title compound. LC1 1.50 min. (M-tBu+H)$^+$ 492.

Step B. N-{4-[(1R)-1-((R)-(4-chlorophenyl){(4-(trifluoromethoxy)benzyl]oxy}methyl)butyl]benzoyl}-β-alanine

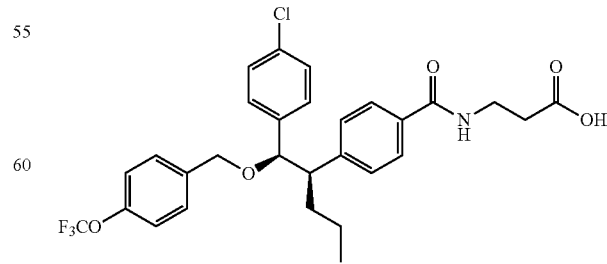

Using the procedure from EXAMPLE 67, Step C, the product of Step A was converted to the title compound. LC1 1.28 min. (M+H)$^+$ 564.

Example 73

N-(4-{(1R)-1-[(R)-(4-chlorophenyl)(2-naphthyl-methoxy)methyl]butyl}benzoyl)-β-alanine

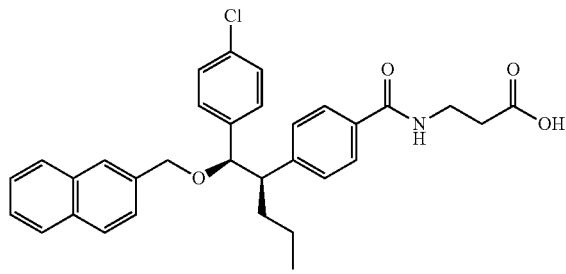 [SMILES: CCC[C@H](c1ccc(C(=O)NCCC(=O)O)cc1)[C@@H](OCc1ccc2ccccc2c1)c1ccc(Cl)cc1]

Using the procedure from EXAMPLE 72, 2-(bromomethyl)naphthalene was converted to the title compound. LC1 1.29 min. (M+H)$^+$ 530.

Example 74

N-(4-{(1R)-1-[(R)-(biphenyl-4-ylmethoxy)(4-chlorophenyl)methyl]butyl}benzoyl)-β-alanine

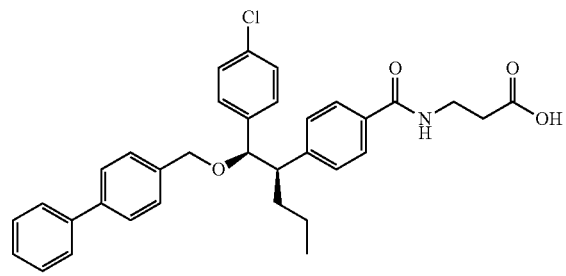 [SMILES: CCC[C@H](c1ccc(C(=O)NCCC(=O)O)cc1)[C@@H](OCc1ccc(-c2ccccc2)cc1)c1ccc(Cl)cc1]

Using the procedure from EXAMPLE 72, 4-(bromomethyl)biphenyl was converted to the title compound. LC1 1.32 min. (M+H)$^+$ 556.

Example 75

N-(4-{(1R)-1-[(R)-(3-chloro-5-cyanophenoxy)(4-chlorophenyl)methyl]-4,4,4-trifluorobutyl}benzoyl)-β-alanine

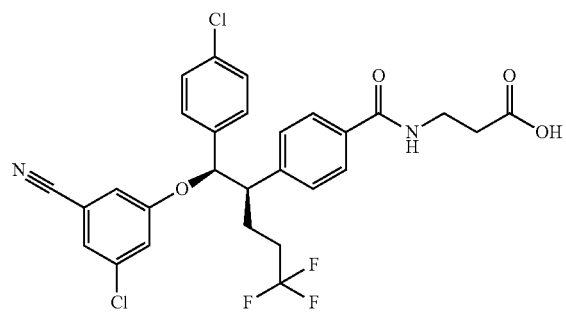 [SMILES: N#Cc1cc(Cl)cc(O[C@@H](c2ccc(Cl)cc2)[C@H](CCC(F)(F)F)c2ccc(C(=O)NCCC(=O)O)cc2)c1]

Step A. N-(4-{(1R)-1-[(R)-[3-(Aminocarbonyl)-5-chlorophenoxy](4-chlorophenyl)methyl]-4,4,4-trifluorobutyl}benzoyl)-β-alanine

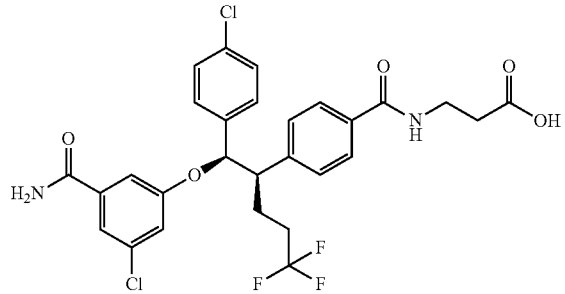 [SMILES: NC(=O)c1cc(Cl)cc(O[C@@H](c2ccc(Cl)cc2)[C@H](CCC(F)(F)F)c2ccc(C(=O)NCCC(=O)O)cc2)c1]

Sodium tert-butoxide (92 mg, 0.96 mmol) was added to a solution of 3-chloro-5-fluorobenzonitrile (67.9 mg, 0.359 mmol) and N-(4-{(1R)-1-[(R)-(4-chlorophenyl)(hydroxy)methyl]-4,4,4-trifluorobutyl}benzoyl)-β-alanine (prepared using the procedures from INTERMEDIATE 1 and the saponification step of EXAMPLE 1, 100 mg, 0.239 mmol) in DMF (3 mL), then the resulting brown mixture was stirred at 80° C. for 16 hours. The mixture was diluted with EtOAc, then washed with 2 N HCl(aq), then washed twice with water. The organic layer was then concentrated, and the resulting yellow residue was purified by reverse phase HPLC eluting with 30-100% MeCN/water+0.1% TFA. Following lyophilization, this afforded the title compound. LC3 3.35 min. (M+H)$^+$ 577.

Step B. N-(4-{(1R)-1-[(R)-3-Chloro-5-cyanophenoxy)(4-chlorophenyl)methyl]-4,4,4-trifluorobutyl}benzoyl)-β-alanine

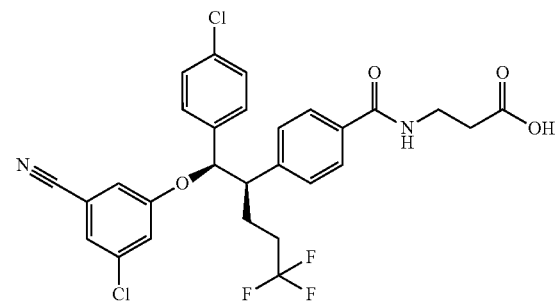 [SMILES: N#Cc1cc(Cl)cc(O[C@@H](c2ccc(Cl)cc2)[C@H](CCC(F)(F)F)c2ccc(C(=O)NCCC(=O)O)cc2)c1]

To a solution of the product from Step A (50 mg, 0.087 mmol) in water (0.5 mL) and acetonitrile (0.5 mL) at room temperature was added palladium (II) chloride (1.5 mg, 8.7 μmol). The resulting mixture was stirred at 50° C. for 12 hours. After cooling to room temperature, the mixture was extracted with EtOAc, then the organic layer was filtered through celite. The filtrate was concentrated, then the resulting residue was purified by PTLC eluting with 5% MeOH/DCM+0.1% HOAc to afford the title compound. NMR (500 MHz, CD$_3$OD): δ 7.74 (d, J=8.0 Hz, 2H); 7.36 (d, J=8.0 Hz, 2H); 7.31 (d, J=8.0 Hz, 2H); 7.24 (d, J=9.0 Hz, 2H); 7.22 (s, 1H); 7.12 (s, 1H); 7.09 (s, 1H); 5.64 (d, J=6.5 Hz, 1H); 3.63 (t, J=9.2 Hz, 2H); 3.26-3.23 (m, 1H); 2.62 (t, J=9.5 Hz, 2H); 2.10-2.05 (m, 2H); 2.00-1.95 (m, 2H); LC3 3.59 min. (M+H)$^+$ 579.

Example 76

N-[4-((1R)-1-{(R)-(4-chlorophenyl)[3-cyano-5-(trifluoromethyl)phenoxy]methyl}butyl)benzoyl]-β-alanine

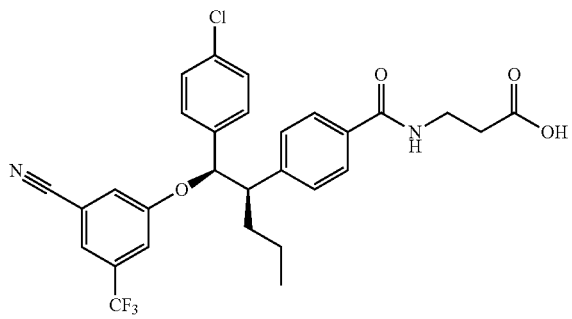 [SMILES: CCC[C@H](c1ccc(C(=O)NCCC(=O)O)cc1)[C@@H](Oc1cc(C#N)cc(C(F)(F)F)c1)c1ccc(Cl)cc1]

Using the procedure from EXAMPLE 75, 3-trifluoromethyl-5-fluorobenzonitrile and INTERMEDIATE 1 were converted to the title compound. LC3 3.96 min. (M+H)+ 559.

Example 77

N-[4-((1R)-1-{(R)-(4-trifluoromethoxyphenyl)[3-cyano-5-(trifluoromethyl)phenoxy]methyl}butyl)benzoyl]-β-alanine

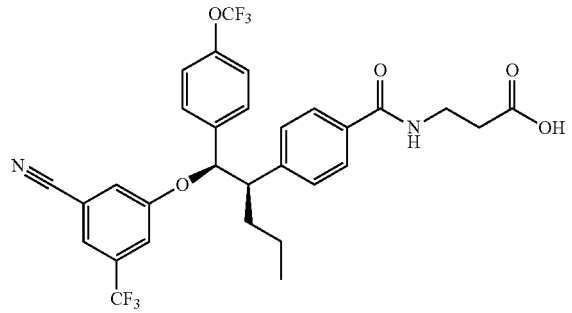 [SMILES: CCC[C@H](c1ccc(C(=O)NCCC(=O)O)cc1)[C@@H](Oc1cc(C#N)cc(C(F)(F)F)c1)c1ccc(OC(F)(F)F)cc1]

Using the procedure from EXAMPLE 75, 3-trifluoromethyl-5-fluorobenzonitrile and N-(4-{(1R)-1-[(R)-(4-trifluoromethoxyphenyl)(hydroxy)methyl]butyl}benzoyl)-β-alanine were converted to the title compound. LC3 4.01 min. (M+H)+ 609.

Example 78

N-(4-{(1R)-1-[(R)-[4-chloro-3-cyano-5-(trifluoromethyl)phenoxy](4-chlorophenyl)methyl]butyl}benzoyl)-β-alanine

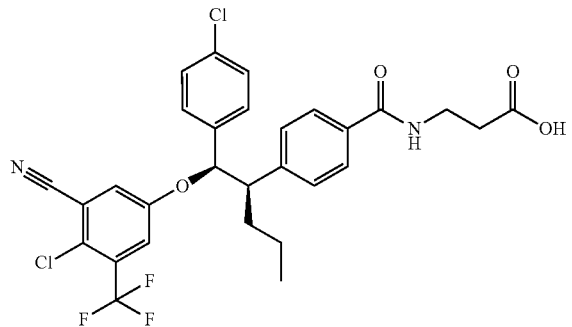 [SMILES: CCC[C@H](c1ccc(C(=O)NCCC(=O)O)cc1)[C@@H](Oc1cc(C#N)c(Cl)c(C(F)(F)F)c1)c1ccc(Cl)cc1]

Step A. 1-Bromo-2-chloro-5-fluoro-3-(trifluoromethyl)benzene

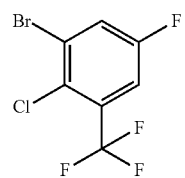

To a mixture of copper (II) chloride (389 mg, 2.90 mmol) and tert-butyl nitrite (368 mg, 3.56 mmol) in acetonitrile (125 mL) at 65° C. was added 2-bromo-4-fluoro-6-(trifluoromethyl)analine (500 mg, 2.23 mmol) in acetonitrile (5 mL). After being stirred at 65° C. for 16 hours, the mixture was filtered through celite, then the orange filtrate was concentrated. The resulting orange residue was purified by silica gel chromatography eluting with 100% hexanes to provide the title compound. $^{1}$H NMR (499 MHz, CD$_3$OD): δ 7.80 (dd, J=8.1, 3.0 Hz, 1H); 7.72 (dd, =7.7, 2.8 Hz, 1H).

Step B. N-(4-{(1R)-1-[(R)-[3-Bromo-4-chloro-5-(trifluoromethyl)phenoxy](4-chlorophenyl)methyl]butyl}benzoyl)-β-alanine

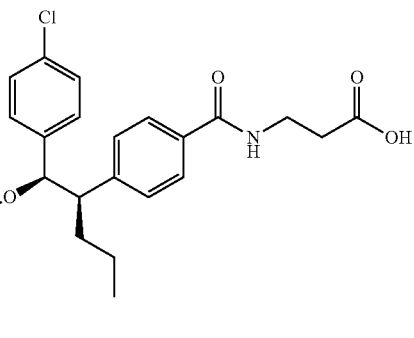

To a solution of the product from Step A (159 mg, 0.574 mmol) and INTERMEDIATE 1 (200 mg, 0.479 mmol) in DMF (2 mL) was added sodium tert-butoxide (137 mg, 1.44 mmol), then the resulting mixture was stirred at 120° C. for 12 hours. After being allowed to cool to RT, the mixture was diluted with EtOAc then washed once with 2N HCl (aq) then twice with water. The organic layer was concentrated, then the resulting residue was purified by reverse phase HPLC eluting with 45-100% acetonitrile/water+0.1% TFA. Following lyophilization, this afforded the title compound. LC2 2.90 min. (M+H)+ 645.

Step C. N-(4-{(1R)-1-[(R)-4-chloro-3-cyano-5-(trifluoromethyl)phenoxy](4-chlorophenyl)methyl]butyl}benzoyl)-β-alanine

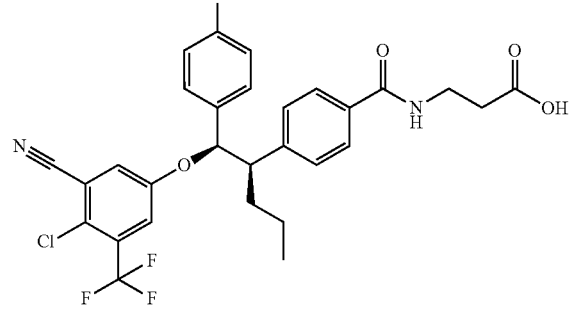

The product from Step B (200 mg, 0.309 mmol), (Ph₃P)₄Pd (107 mg, 0.093 mmol), and zinc cyanide (54.4 mg, 0.473 mmol) were stirred in DMF (3 mL) at 120° C. for 24 hours. After cooling to RT, the mixture was filtered through celite, then the filtrate was concentrated. The resulting residue was purified by reverse phase HPLC eluting with 60-100% acetonitrile/water+0.1% TFA. Following lyophilization, this afforded the title compound. ¹H NMR (500 MHz, (CD₃)₂CO): δ 7.78 (d, J=8.5 Hz, 2H); 7.62 (d, J=3.0 Hz, 1H); 7.56 (d, 2.5 Hz, 1H); 7.41 (d, J=3.0 Hz, 2H); 7.39 (d, J=2.5 Hz, 2H); 7.34 (d, J=8.5 Hz, 2H); 5.90 (d, J=7.0 Hz, 1H); 3.61 (m, 2H); 3.29 (m, 1H); 2.63 (m, 2H); 2.62-1.77 (m, 1H); 1.62-1.55 (m, 1H); 1.15-1.08 (m, 2H); 0.76 (t, J=7.2 Hz, 3H); LC3 4.09 min. (M+H)⁺ 593.

Using the chemistry in EXAMPLE 78, the compounds in TABLE 4 were prepared as enantiopure compounds.

TABLE 4

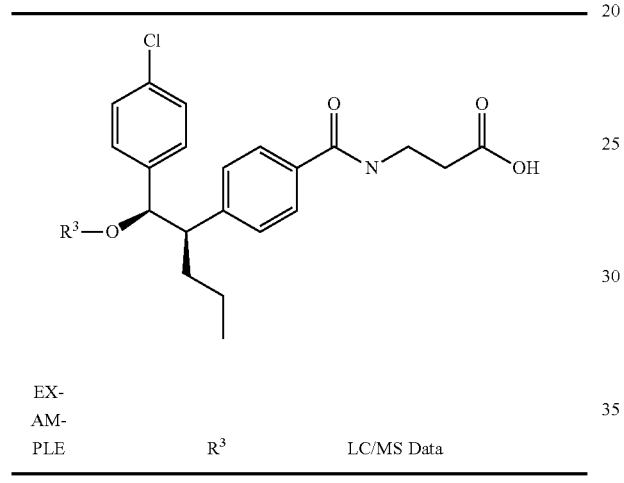

| EXAMPLE | R³ | LC/MS Data |
|---|---|---|
| 79 | 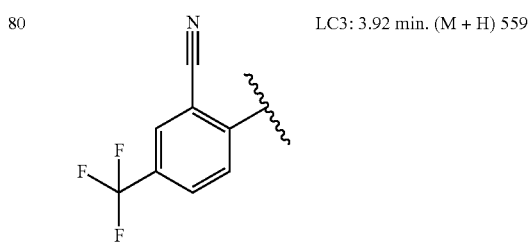 | LC3: 3.93 min. (M + H) 559 |

¹H NMR (500 MHz, CD₃OD): δ 7.75 (d, J = 7.5 Hz, 1 H); 7.70 (d, J = 8.0 Hz, 2 H); 7.41 (d, J = 8.0 Hz, 2 H); 7.28 (d, J = 8.5 Hz, 2 H); 7.25 (d, J = 8.0 Hz, 1 H); 7.20 (d, J = 8.0 Hz, 2 H); 7.13 (s, 1 H); 5.77 (d, J = 6.0 Hz, 1 H); 3.60 (t, J = 6.5 Hz, 2 H); 3.23 (m, 1 H); 2.61 (t, J = 6.5 Hz, 2 H); 1.98-1.69 (m, 2 H); 1.67-1.29 (m, 2 H); 1.14 (t, J = 7.2 Hz, 3 H).

| 80 | (2-CN, 4-CF₃ phenyl) | LC3: 3.92 min. (M + H) 559 |

TABLE 4-continued

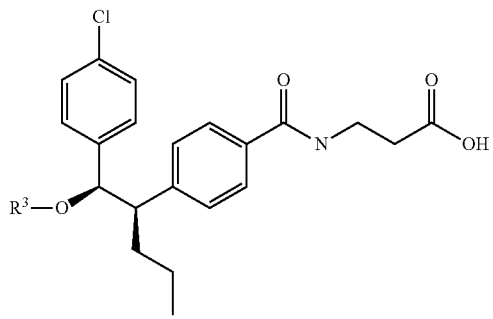

| EXAMPLE | R³ | LC/MS Data |
|---|---|---|
| 81 | (2-CN, 6-F, 4-CF₃ phenyl) | LC3: 3.71 min. (M + H) 577 |
| 82 | (2-CN, 3-Cl, 5-Cl phenyl) | LC3: 4.00 min. (M + H) 561 |
| 83 | (2-CN, 4-Me, 5-Cl phenyl) | LC3: 4.01 min. (M + H) 539 |
| 84 | (2-CN, 4-Cl phenyl) | LC3: 3.61 min. (M + H) 525 |
| 85 | (2-CN, 3-Cl, 4-Cl phenyl) | LC3: 3.75 min. (M + H) 561 |

¹H NMR (500 MHz, CD₃OD): δ 7.67 (d, J = 8.5 Hz, 2 H); 7.30 (d, J = 8.0 Hz, 2 H); 7.27 (d, J = 8.5 Hz, 2 H); 7.21 (d, J = 8.5 Hz, 2 H); 7.21 (d, J = 2.5 Hz, 1 H); 7.14 (d, J = 2.0 Hz, 1 H); 5.51 (d, J = 7.0 Hz, 1 H); 3.56 (m, 2 H); 3.13 (m, 1 H); 2.58 (m, 2 H); 1.76-1.71 (m, 1 H); 1.51-1.47 (m, 1 H); 1.10-1.01 (m, 2 H); 0.74 (t, J = 7.3 Hz, 3 H).

Example 86

N-[4-(1-{1-(4-chlorophenyl)-2-[(6-methoxy-2-naphthyl)oxy]ethyl}butyl)benzoyl]-β-alanine

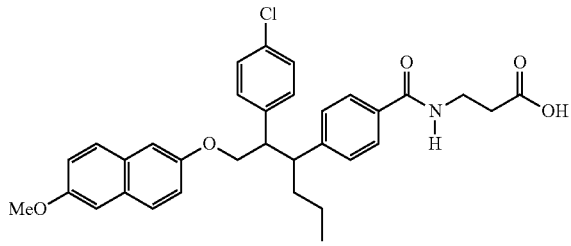 [SMILES: CCCC(c1ccc(C(=O)NCCC(=O)O)cc1)C(COc1ccc2cc(OC)ccc2c1)c1ccc(Cl)cc1]

Step A. 4-{1-[2-tert-Butoxy-1-(4-chlorophenyl)-2-oxoethyl]butyl}benzoic acid

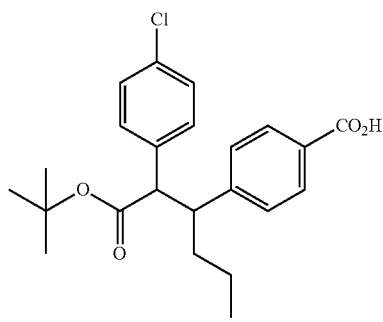 [SMILES: CCCC(c1ccc(C(=O)O)cc1)C(C(=O)OC(C)(C)C)c1ccc(Cl)cc1]

To a solution of methyl 4-{1-[2-tert-butoxy-1-(4-chlorophenyl)-2-oxoethyl]butyl}benzoate (prepared as described in PCT Patent Publication WO 2008/042223 A1 published on 10 Apr. 2008, 20 g, 48 mmol) in MeOH was slowly added NaOH (5.0 N in $H_2O$, 19 mL, 95 mmol) at ambient temperature. Once all the ester starting material was consumed by LC-MS analysis, the mixture was concentrated. The residue was partitioned between EtOAc and 1N HCl (aq). The organic layer was then washed with water then saturated NaCl (aq). The organic layer was then dried over $Na_2SO_4$, filtered, then concentrated. The resulting acid was used directly for the following step. $^1$H NMR (400 MHz, DMSO-$d_6$) δ 12.80 (s, 1H); 7.88 (d, J=8 Hz, 2H); 7.48-7.65 (m, 2H); 7.45-7.74 (m, 3H); 7.15 (s, 1H); 3.87 (d, J=11.6 Hz, 1H); 3.15-3.11 (m, 1H); 1.61-1.70 (m, 1H); 1.06-1.14 (m, 1H); 0.97 (s, 9H); 0.76-0.86 (m, 2H); 0.56 (t, 0.1=7.6 Hz, 3H). LC3 2.54 min. (M-tBu+H)$^+$ 347.

Step B. tert-Butyl 2-(4-chlorophenyl)-3-(4-{[(3-methoxy-3-oxopropyl)amino]carbonyl}phenyl)hexanoate

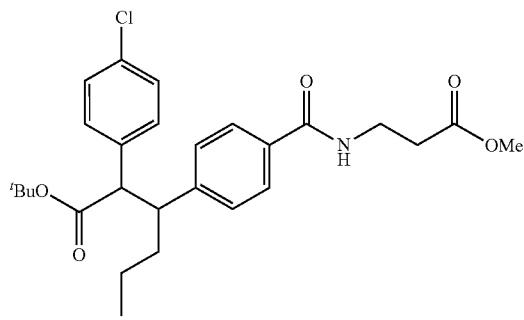 [SMILES: CCCC(c1ccc(C(=O)NCCC(=O)OC)cc1)C(C(=O)OC(C)(C)C)c1ccc(Cl)cc1]

A mixture of the product from Step A (6.2 g, 15.3 mmol), EDC (4.4 g, 23.0 mmol), and HOBt (3.1 g, 23.0 mmol) in anhydrous DCM (200 mL) was stirred for 30 min at RT, then β-alanine methyl ester (2.1 g, 15.3 mmol) and DIEA (8.0 mL, 45.9 mmol) were added. After being stirred for 12 hours at RT, the mixture was diluted with DCM then washed with 100 mL of 0.5 M HCl (aq) then 100 mL of saturated NaCl (aq). The organic layer was dried over $Na_2SO_4$, filtered, then concentrated. The major diastereomer of the title compound was obtained by trituration with hexane.

Major Diastereomer $^1$H NMR (300 MHz, CDCl$_3$) δ 7.50 (d, J=8 Hz, 2H); 6.97-7.03 (m, 6H); 6.73 (t, J=6.0 Hz, 1H); 3.67 (s, 3H); 3.57-3.65 (m, 3H); 3.23-3.32 (m, 1H); 2.59 (t, 0.1=6.0 Hz, 2H); 1.74-1.64 (m, 2H); 1.41 (s, 9H); 1.05-1.10 (m, 2H); 0.82 (s, J=7.6 Hz, 3H). MS (M+H)$^+$ 488.

Step C. Methyl N-(4-{1-[1-(4-chlorophenyl)-2-hydroxyethyl]butyl}benzoyl)-β-alaninate

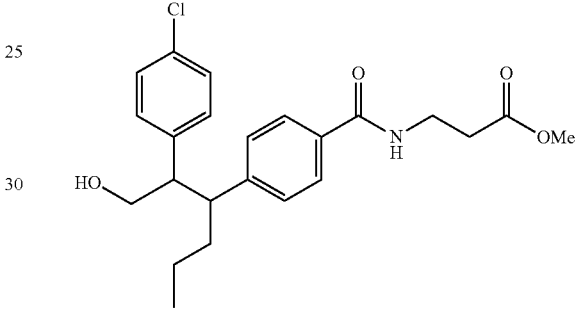

The major diastereomer of the product from Step B (3.00 g, 6.15 mmol) was dissolved in DCM (15 mL) then TFA (15 mL) was added. After being stirred for four hours at RT, the mixture was concentrated, then the residue was diluted with EtOAc and water. The organic layer was washed with saturated NaCl (aq), dried over $Na_2SO_4$, filtered, then concentrated to afford the carboxylic acid which was used directly in the next step.

A solution of the acid from the previous step (1.2 g, 2.8 mmol) in anhydrous THF (20 mL) was cooled to 0° C., then borane dimethyl sulfide complex (1.2 mL, 12 mmol) was added slowly. The mixture was stirred at room temperature for five hours, then excess reagent was quenched with MeOH (10 mL). The mixture was concentrated, then the resulting residue was diluted with EtOAc (50 mL) and $K_2CO_3$ (aq). The organic layer was washed with water, dried over anhydrous $Na_2SO_4$, filtered, then concentrated. The resulting residue was purified by silica gel chromatography eluting with 10% MeOH/DCM to afford the title compound. $^1$H NMR (300 MHz, CDCl$_3$) δ 7.72 (d, J=8 Hz, 2H); 7.20-7.38 (m, 6H); 6.87 (d, J=6.0 Hz, 1H); 3.66-3.75 (m, 5H); 3.41-3.50 (m, 2H); 2.82-2.96 (m, 2H); 2.66 (t, J=6.0 Hz, 2H); 1.25-1.32 (m, 2H); 0.81-0.94 (m, 2H); 0.66 (t, J=7.2 Hz, 3H). MS (M+H)$^+$ 418.

The minor diastereomer of the title compound was obtained by applying the same procedure to the minor diastereomer of the product from Step B.

Step D. Methyl N-[4-(1-{1-(4-chlorophenyl)-2-[(6-methoxy-2-naphthyl)oxy]ethyl}butyl)benzoyl]-β-alaninate

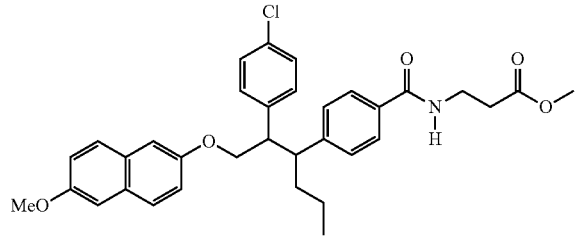 [SMILES: CCCC(c1ccc(C(=O)NCCC(=O)OC)cc1)C(COc1ccc2cc(OC)ccc2c1)c1ccc(Cl)cc1]

To a solution of the major diastereomer of the product from Step C (100 mg, 0.24 mmol), 6-methoxy-2-naphthol (50 mg, 0.29 mmol) and PPh$_3$ (189 mg, 0.72 mmol) in anhydrous THF (5 mL) at 0° C. was added DIAD (145 mg, 0.72 mmol). The mixture was stirred at room temperature overnight, then diluted with EtOAc (30 mL) and washed with water then saturated NaCl (aq). The organic layer was concentrated, then the resulting residue was purified by preparative reverse phase HPLC eluting with acetonitrile/water+0.1% TFA. Following lyophilization, this afforded the title compound. NMR (400 MHz, CDCl$_3$) δ 7.71 (d, J=8 Hz, 2H); 7.55 (d, J=8.8 Hz, 1H); 7.46 (d, J=8.8 Hz, 1H); 7.29-7.44 (m, 6H); 7.04-7.08 (m, 2H); 6.92-7.00 (m, 2H); 6.76 (s, 1H); 3.86-3.92 (m, 5H); 3.70-3.74 (m, 5H); 3.16-3.20 (m, 2H); 2.66 (t, J=6.0 Hz, 2H); 1.40-1.49 (m, 2H); 0.92-1.02 (m, 2H); 0.73 (t, J=7.2 Hz, 3H). MS (M+H)$^+$ 574.

The minor diastereomer of the title compound was obtained by applying the same procedure to the minor diastereomer of the product from Step C. $^1$H NMR (400 MHz, CDCl$_3$) δ 7.55-7.66 (m, 4H); 7.07-7.15 (m, 6H); 6.96 (d, J=8 Hz, 2H); 6.86 (d, 0.1=8 Hz, 2H); 6.74 (t, J=6.0 Hz, 1 Fl); 4.22 (d, J=5.2 Hz, 2H); 3.90 (s, 3H); 3.55-3.72 (m, 5H); 3.36-3.39 (m, 2H); 2.64 (t, J=6.0 Hz, 2H); 1.82-1.87 (m, 1H); 1.59-1.61 (m, 1H); 1.11-1.19 (m, 2H); 0.84 (t, 0.1=7.2 Hz, 3H). MS (M+H)$^+$ 574.

Step E. N-[4-(1-{1-(4-chlorophenyl)-2-[(6-methoxy-2-naphthyl)oxy]ethyl}butyl)benzoyl]-β-alanine

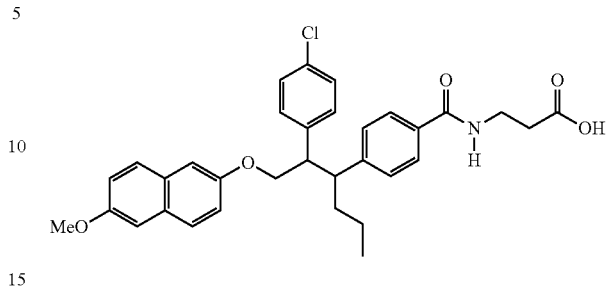

Sodium hydroxide (1.0 M in H$_2$O, 0.5 mL, 0.5 mmol) was added to a solution of the major diastereomer of the product from step D (14 mg, 0.024 mmol) in MeOH (2 mL). After stirring at room temperature for four hours, the pH was adjusted to 3-4 with HCl (aq), then the mixture was extracted with EtOAc. The organic layer was dried over anhydrous Na$_2$SO$_4$, filtered, then concentrated. The resulting residue was purified by PTLC to afford the racemic title compound. This diastereomer is the more potent glucagon receptor antagonist. $^1$H NMR (300 MHz, CDCl$_3$) δ 7.70 (d, J=8 Hz, 2H); 7.47-7.55 (m, 2H); 7.30-7.34 (m, 6H); 7.01-7.08 (m, 2H); 6.91-6.95 (m, 1H); 6.71-6.79 (m, 2H); 3.82-3.95 (m, 5H); 3.67-3.74 (m, 2H); 3.12-3.20 (m, 2H); 2.69 (t, J=8.0 Hz, 2H); 1.39-1.47 (m, 2H); 0.87-1.02 (m, 2H); 0.70 (t, J=7.2 Hz, 3H). MS (M+H)$^+$ 560.

The racemic minor diastereomer of the title compound was obtained by applying the same procedure to the minor diastereomer of the product from Step C. $^1$H NMR (300 MHz, CDCl$_3$) δ 7.52-7.67 (m, 4H); 7.05-7.15 (m, 6H); 6.97 (d, J=8 Hz, 2H); 6.87 (d, J=8 Hz, 2H); 6.70 (t, J=6.0 Hz, 1H); 4.21 (d, J=5.4 Hz, 2H); 3.89 9 (s, 3H); 3.64-3.72 (m, 2H); 3.37-3.41 (m, 2H); 2.70 (t, J=5.7 Hz, 2H); 1.81-1.90 (m, 1H); 1.65-1.71 (m, 1H); 1.15-1.21 (m, 2H); 0.82 (t, J=7.2 Hz, 3H). MS (M+H)$^+$ 560.

Example 87

N-[4-(1-{1-(4-chlorophenyl)-2-[(4'-methoxybiphenyl-4-yl)oxy]ethyl}butyl)benzoyl]-β-alanine

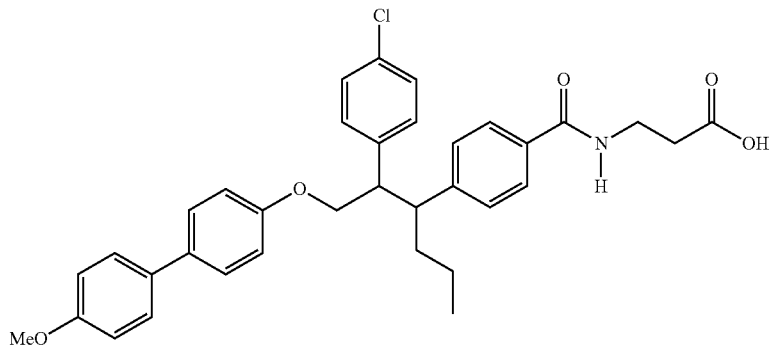 [SMILES: CCCC(c1ccc(C(=O)NCCC(=O)O)cc1)C(COc1ccc(-c2ccc(OC)cc2)cc1)c1ccc(Cl)cc1]

Using the procedure from EXAMPLE 86, Steps D and E, 4'-methoxybiphenyl-4-ol and the major diastereomer of the product from EXAMPLE 86, Step C were converted to the racemic title compound. This diastereomer is the more potent glucagon receptor antagonist. $^1$H NMR (400 MHz, CDCl$_3$) δ 7.71 (d, J=8 Hz, 2H); 7.41 (d, J=8 Hz, 2H); 7.29-737 (m, 8H); 6.92 (d, J=8 Hz, 2H); 6.84 (t, J=5.6 Hz, 1H); 6.68 (d, J=8 Hz, 2H); 3.79-3.87 (m, 5H); 3.69-3.74 (m, 2H); 3.13-3.14 (m, 2H); 2.70 (t, J=6.0 Hz, 2H); 1.39-1.47 (m, 2H); 0.92-0.99 (m, 2H); J=7.2 Hz, 3H). MS (M+H)$^+$ 586.

Using the procedure from EXAMPLE 86, Steps D and E, 4'-methoxybiphenyl-4-ol and the minor diastereomer of the product from EXAMPLE 86, Step C were converted to the minor diastereomer of the racemic title compound. $^1$H NMR (400 MHz, CDCl$_3$) δ 7.56 (d, J=8 Hz, 2H); 7.43-7.49 (m, 4H); 7.10-7.14 (m, 2H); 6.92-6.97 (m, 6H); 6.84-6.88 (m, 2H); 6.72 (t, J=6.0 Hz, 1H); 4.16 (d, J=4.0 Hz, 2H); 3.84 (s, 3H); 3.68-3.74 (m, 2H); 3.32-3.39 (m, 2H); 2.71 (t, J=6.0 Hz, 2H); 1.81-1.89 (m, 1H); 1.63-1.72 (m, 1H); 1.11-1.19 (m, 2H); 0.88 (t, J=7.2 Hz, 3H). MS (M+H)$^+$ 586.

Example 88

N-[4-(1-{1-(4-chlorophenyl)-2-[4-(trifluoromethoxy)phenoxy]ethyl}butyl)benzoyl]-β-alanine

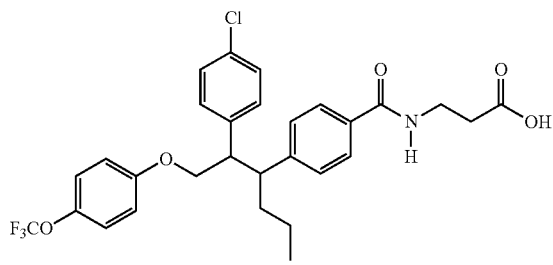 [SMILES: CCCC(c1ccc(C(=O)NCCC(=O)O)cc1)C(COc1ccc(OC(F)(F)F)cc1)c1ccc(Cl)cc1]

Using the procedure from EXAMPLE 86, Steps D and E, 4-trifluoromethoxyphenol and the major diastereomer of the product from EXAMPLE 86, Step C were converted to the racemic title compound. $^1$H NMR (400 MHz, CDCl$_3$) δ 7.71 (d, J=8 Hz, 2H); 7.24-7.43 (m, 6H); 7.01 (d, J=8 Hz, 2H); 6.82 (t, J=6.0 Hz, 1H); 6.59-6.63 (m, 2H); 3.72-3.79 (m, 4H); 3.06-3.14 (m, 2H); 2.72 (t, J=5.6 Hz, 2H); 1.39-1.46 (m, 2H); 0.88-0.97 (m, 2H); 0.69 (t, J=7.2 Hz, 3H). MS (M+H)$^+$ 564.

Using the procedure from EXAMPLE 86, Steps D and E, 4-trifluoromethoxyphenol and the minor diastereomer of the product from EXAMPLE 86, Step C were converted to the minor diastereomer of the racemic title compound. This diastereomer is the more potent glucagon receptor antagonist. $^1$H NMR (300 MHz, CDCl$_3$) δ 7.56 (d, J=8 Hz, 2H); 7.11-7.18 (m, 4H); 6.94 (d, J=8 Hz, 2H); 6.82-6.91 (m, 4H); 6.71 (t, J=6.0 Hz, 1H); 4.11 (d, J=4.8 Hz, 2H); 3.67-3.74 (m, 2H); 3.29-3.33 (m, 2H); 2.71 (t, J=5.7 Hz, 2H); 1.78-1.89 (m, 1H); 1.64-1.71 (m, 1H); 1.10-1.19 (m, 2H); 0.87 (t, J=7.2 Hz, 3H). MS (M+H)$^+$ 564.

Example 89

N-{4-[1-(1-(4-chlorophenyl)-2-{[4-(trifluoromethoxy)benzyl]oxy}ethyl)butyl]benzoyl}-β-alanine

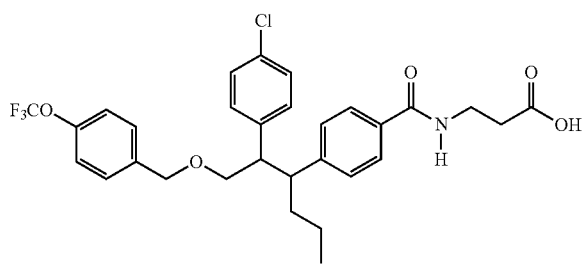 [SMILES: CCCC(c1ccc(C(=O)NCCC(=O)O)cc1)C(COCc1ccc(OC(F)(F)F)cc1)c1ccc(Cl)cc1]

Step A. Methyl N-{4-[1-(1-(4-chlorophenyl)-2-{[4-(trifluoromethoxy)benzyl]oxy}ethyl)butyl]benzoyl}-β-alaninate

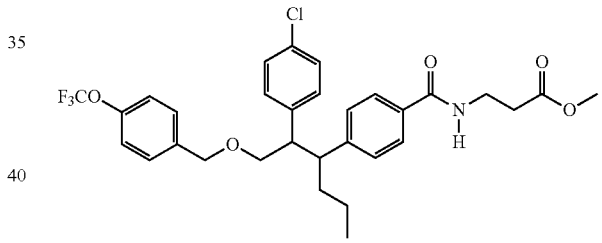

The major diastereomer of methyl N-(4-{1-[1-(4-chlorophenyl)-2-hydroxyethyl]butyl}benzoyl)-β-alaninate (EXAMPLE 86, Step C, 80 mg, 0.19 mmol), 1-(bromomethyl)-4-(trifluoromethoxy)benzene (97 mg, 0.38 mmol) and Ag$_2$O (87 mg, 0.38 mmol) in DCM (20 mL) was refluxed overnight. After cooling to room temperature, the mixture was filtered, then the filtrate was concentrated. The resulting residue was purified by PTLC to afford the title compound. $^1$H NMR (300 MHz, CDCl$_3$) δ 7.71 (d, J=8 Hz, 2H); 7.22-7.31 (m, 6H); 7.05-7.12 (m, 4H); 6.90 (t, J=5.4 Hz, 1H); 4.10-4.24 (m, 2H); 332-3.77 (m, 5H); 3.22-3.29 (m, 2H); 2.94-2.98 (m, 2H); 2.67 (t, J=53 Hz, 2H); 1.32-1.44 (m, 2H); 0.88-0.94 (m, 2H); 0.65 (1, J=7.2 Hz, 3H). MS (M+H)$^+$ 592.

The minor diastereomer of the title compound was obtained by applying the same procedure to the minor diastereomer of the product from EXAMPLE 86, Step C. $^1$H NMR (400 MHz, CDCl$_3$) δ 7.54 (d, J=8 Hz, 2H); 728 (d, J=8 Hz, 2H); 7.18 (d, J=8 Hz, 2H); 7.10 (d, J=8 Hz, 2H); 6.90 (d, J=8 Hz, 2H); 6.74-6.79 (m, 2H); 4.43-4.52 (m, 2H); 3.64-3.71

(m, 7H); 3.12-3.18 (m, 2H); 2.64 (t, J=5.6 Hz, 2H); 1.66-1.75 (m, 1H); 1.53-1.64 (m, 1H); 1.02-1.13 (m, 2H); 0.82 (t, J=7.2 Hz, 3H). MS (M+H)+ 592.

Step B. N-{4-[1-(1-(4-chlorophenyl)-2-{[4-(trifluoromethoxy)benzyl]oxy}ethyl)butyl]benzoyl}-β-alanine

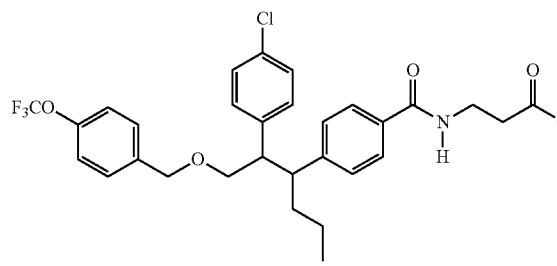

Using the procedure from EXAMPLE 86, Step E, the major diastereomer of the product from Step A was converted to the racemic title compound. ¹H NMR (300 MHz, CDCl₃,) δ 7.72 (d, J=8 Hz, 2H); 7.30 (d, J=8 Hz, 2H); 7.18-7.27 (m, 4H); 7.01-7.11 (m, 4H); 6.95 (t, J=5.7 Hz, 1H): 4.10-4.24 (m, 2H); 3.72-3.78 (m, 2H); 3.26-3.32 (m, 2H); 2.92-3.01 (m, 2H); 2.73 (t, J=5.7 Hz, 2H); 1.29-1.41 (m, 2H); 0.81-0.94 (m, 2H); 0.65 (t, J=7.2 Hz, 3H). MS (M+H)+ 578.

Using the procedure from EXAMPLE 86, Step E, the minor diastereomer of the product from Step A was converted to the minor diastereomer of the racemic title compound. This diastereomer is the more potent glucagon receptor antagonist. ¹H NMR (400 MHz, CDCl₃) δ 7.54 (d, J=8 Hz, 2H); 7.26 (d, J=8 Hz, 2H); 7.17 (d, J=8 Hz, 2H); 7.09 (d, J=8 Hz, 2H); 6.90 (d, J=8 Hz, 2H); 6.75-6.82 (m, 2H); 4.43-4.52 (m, 2H); 3.63-3.72 (m, 4H); 3.09-3.18 (m, 2H); 2.68 (t, J=5.6 Hz, 2H); 1.73-1.82 (m, 1H); 1.52-1.64 (m, 1H); 1.02-1.11 (m, 2H); 0.82 (t, J=7.2 Hz, 3H). MS (M+H)+ 578.

Example 90

N-(4-{1-[2-(biphenyl-4-ylmethoxy)-1-(4-chlorophenyl)ethyl]butyl}benzoyl)-β-alanine

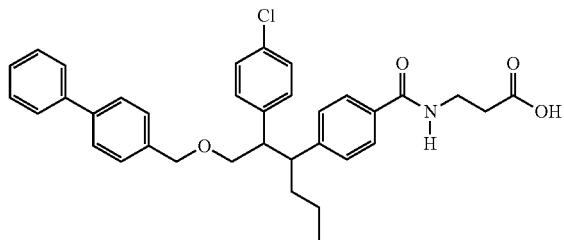 [SMILES: CCCC(c1ccc(C(=O)NCCC(=O)O)cc1)C(COCc1ccc(-c2ccccc2)cc1)c1ccc(Cl)cc1]

Using the procedure from EXAMPLE 89, 4-(bromomethyl)biphenyl and the major diastereomer of the product from EXAMPLE 86, Step C were converted to the racemic title compound. ¹H NMR (300 MHz, CDCl₃) δ 7.71 (d, J=8 Hz, 2H); 7.59 (d, J=8 Hz, 2H); 7.40-7.52 (m, 4H); 7.20-7.38 (m, 7H); 7.12 (d, J=8 Hz, 2H); 6.85 (t, J=5.7 Hz, 1H); 4.16-4.31 (m, 2H); 3.62-3.74 (m, 2H); 3.29-3.32 (m, 2H); 2.95-3.03 (m, 2H); 2.69 (t, J=5.7 Hz, 2H); 1.36-1.47 (m, 2H); 0.82-0.99 (m, 2H); 0.65 (t, J=7.2 Hz, 3H). MS (M+H)+ 570.

Using the procedure from EXAMPLE 89, 4-(bromomethyl)biphenyl and the minor diastereomer of the product from EXAMPLE 86, Step C were converted to the minor diastereomer of the racemic title compound. This diastereomer is the more potent glucagon receptor antagonist. ¹H NMR (400 MHz, CDCl₃) δ 7.50-7.62 (m, 6H); 7.42-7.49 (m, 2H); 7.32-7.40 (m, 3H); 7.10 (d, 0.1=8 Hz, 2H); 6.90 (d, J=8 Hz, 2H); 6.79 (d, J=8 Hz, 2H); 6.72 (t, J=5.6 Hz, 1H); 4.49-4.57 (m, 2H); 3.65-3.72 (m, 2H); 3.11-3.22 (m, 2H); 2.83-2.96 (m, 2H); 2.67 (t, J=6.0 Hz, 2H); 1.72-1.84 (m, 1H); 1.52-1.66 (m, 1H); 1.04-1.15 (m, 2H); 0.86 (t, J=7.2 Hz, 3H). MS (M+H)+ 570.

Example 91

N-(4-{1-[2-(1,3-benzothiazol-2-ylmethoxy)-1-(4-chlorophenyl)ethyl]butyl}benzoyl)-β-alanine

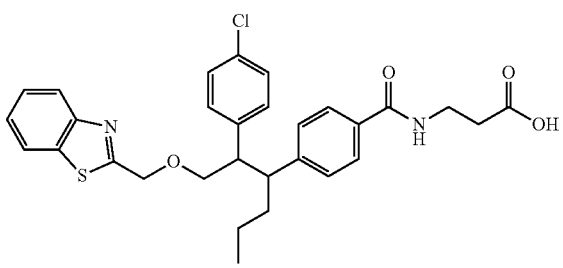 [SMILES: CCCC(c1ccc(C(=O)NCCC(=O)O)cc1)C(COCc1nc2ccccc2s1)c1ccc(Cl)cc1]

Step A. Methyl 4-{1-[1-(4-chlorophenyl)-2-hydroxyethyl]butyl}benzoate

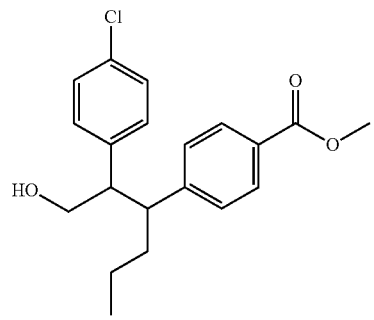 [SMILES: CCCC(c1ccc(C(=O)OC)cc1)C(CO)c1ccc(Cl)cc1]

A solution of 2-(4-chlorophenyl)-3-[4-(methoxycarbonyl)phenyl]hexanoic acid (prepared as described in PCT Patent Publication WO 2008/042223 A1 published on 10 Apr. 2008, 360 mg, 1.0 mmol) in anhydrous THF (10 mL) was cooled to 0° C., then borane dimethyl sulfide complex (0.3 mL, 3 mmol) was added slowly. The mixture was stirred at room temperature for five hours, then excess reagent was quenched with MeOH (2 mL). The mixture was concentrated, then the resulting residue was diluted with EtOAc (20 mL) and K₂CO₃ (aq). The organic layer was washed with water, dried over anhydrous Na₂SO₄, filtered, then concentrated. The resulting residue was purified by silica gel chromatography eluting with 10% MeOH/DCM to afford the title compound. MS (M±H)+ 347.

Step B. tert-Butyl N-(4-{1-[1-(4-chlorophenyl)-2-hydroxyethyl]butyl}benzoyl)-β-alaninate

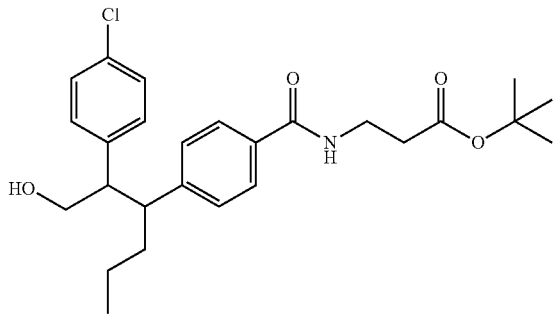 [SMILES: CCCC(c1ccc(C(=O)NCCC(=O)OC(C)(C)C)cc1)C(CO)c1ccc(Cl)cc1]

To a solution of the product from Step A (300 mg, 0.89 mmol) in MeOH (5 mL) was added NaOH (1.0 M in $H_2O$, 1.0 mL, 1.0 mmol) at room temperature. After being stirred at room temperature overnight, the pH was adjusted to 3-4 with HCl (aq), then the mixture was extracted with EtOAc. The organic layer was dried over anhydrous $Na_2SO_4$, filtered, then concentrated to provide the corresponding carboxylic acid which was used directly for the next step.

A mixture of the carboxylic acid from the previous step (240 mg, 0.72 mmol), EDC (280 mg, 1.44 mmol), and HOBt (200 mg, 1.44 mmol) in anhydrous DCM (10 mL) was stirred for 30 min at RT, then β-alanine tert-butyl ester (207 mg, 1.44 mmol) and DIEA (1.0 mL, 5.7 mmol) were added. After being stirred for 12 hours at RT, the mixture was diluted with DCM then washed with 10 mL of 0.5 M (aq) then 10 mL of saturated NaCl (aq). The organic layer was dried over $Na_2SO_4$, filtered, then concentrated. The resulting residue was purified by PTLC to afford the title compound. MS (M+H)+ 460.

Step C. N-(4-{1-[2-(1,3-benzothiazol-2-ylmethoxy)-1-(4-chlorophenyl)ethyl]butyl}benzoyl)-β-alanine

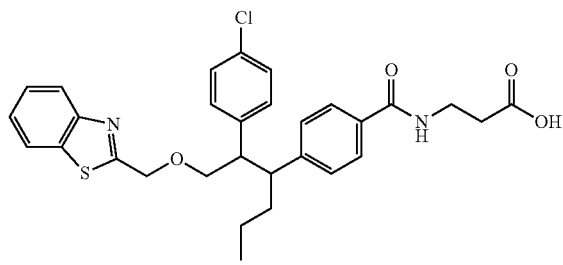 [SMILES: CCCC(c1ccc(C(=O)NCCC(=O)O)cc1)C(COCc1nc2ccccc2s1)c1ccc(Cl)cc1]

NaH (60 wt % in mineral oil, 20 mg, 0.47 mmol) was added to a solution of the product from Step B (200 mg, 0.43 mmol) in anhydrous DMF (5 mL) at −5° C. The mixture was stirred at room temperature for 30 minutes, then a solution of 2-(bromomethyl)-1,3-benzothiazole (117 mg, 0.52 mmol) in DMF (1 mL) was added dropwise. After being stirred for four hours, the mixture was poured into EtOAc (50 mL) then washed with water then saturated NaCl (aq). The organic layer was dried over anhydrous $Na_2SO_4$, filtered, then concentrated. The resulting residue was purified, and the two diastereomers were separated, by PTLC.

Each diastereomer was independently dissolved in DCM (1.0 mL) then treated with TFA (1.0 mL). After stirring at room temperature for three hours, the solutions were concentrated. Residual TFA was removed by azeotroping with benzene. The resulting residues were purified by PTLC eluting with 10% MeOH/DCM to afford the two diastereomers of the title compound. The minor diastereomer was the more potent glucagon antagonist.

Major Diastereomer $^1$H NMR (400 MHz, $CDCl_3$) δ 7.96 (d, J=8.4 Hz, 1H); 7.88 (d, 0.1=8.0 Hz, 1H); 7.69 (d, J=8 Hz, 2H); 7.42-7.49 (m, 1H); 7.39-7.41 (m, 1H); 7.34-7.37 (m, 2H); 7.27-7.32 (m, 4H); 6.93 (t, J=5.6 Hz, 1H); 4.52-4.62 (m, 2H); 3.69-3.78 (m, 2H); 3.39-3.42 (m, 2H); 2.94-3.05 (m, 2H); 2.72 (t, J=6.0 Hz, 2H); 1.32-1.46 (m, 2H); 0.87-0.95 (m, 2H); 0.66 (t, J=7.2 Hz, 3H). MS (M+H)+ 551.

Minor Diastereomer $^1$H NMR (400 MHz, $CDCl_3$) δ 8.00 (d, J=8.0 Hz, 1H); 7.90 (d, J=8.0 Hz, 1H); 7.49-7.58 (m, 3H); 7.38-7.42 (m, 1H); 7.10 (d, J=8 Hz, 2H); 6.93 (d, J=8 Hz, 2H); 6.78-6.85 (m, 3H); 4.87-4.92 (m, 2H); 3.76-3.84 (m, 2H); 3.69-3.74 (m, 2H); 3.15-3.22 (m, 2H); 2.71 (t, J=6.0 Hz, 2H); 1.76-1.85 (m, 1H); 1.57-1.72 (m, 1H); 1.02-1.13 (m, 2H); 0.82 (t, J=7.2 Hz, 3H). MS (M+H)+ 551.

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chiechi, et. al. *J Biol Chem* 272, 7765-9 (1997); Cascieri, et. al. *J Biol Chem* 274, 8694-7 (1999)). To determine antagonistic binding affinity of compounds, 0.001-0.003 mg of cell membranes from these cells were pre-incubated with 0.100 mg WGA-coated PVT SPA beads (Amersham) for 20 minutes at room temperature in 25 μL of a buffer containing 50 mM Tris-HCl (pH 7.5), 5 mM $MgCl_2$, 2 mM EDTA, 0.1% BSA and 3% glycerol in Costar 384 well plates with clear bottoms (#3706). Next, 25 μL of $^{125}$I-Glucagon (New England Nuclear, Mass.) ($1 \times 10^{-14}$ mol per well) and either 1 μL solutions of test compounds or 0.001 mM unlabeled glucagon or DMSO were added and mixed. After 4-12 hours incubation at room temperature, the radioactivity bound to the cell membranes was determined in a radioactive emission detection counter (Wallac-Microbeta). Data were analyzed using the Data Analyzer software program of Merck & Co., Inc. The $IC_{50}$ values were calculated using non-linear regression analysis assuming single-site competition. $IC_{50}$ values for the compounds of the invention are generally in the range of as low as about 1 nM to as high as about 500 nM, and thus have utility as glucagon antagonists. When a synthetic example includes the preparation of both diastereomers of a compound, the $IC_{50}$ value shown below in TABLE 5 is for the more active diastereomer of the indicated compound.

TABLE 5

| Example | $IC_{50}$ (nM) |
|---|---|
| 1 | 16 |
| 5 | 11 |
| 9 | 6.2 |
| 15 | 5.9 |

TABLE 5-continued

| Example | IC$_{50}$ (nM) |
|---|---|
| 16 | 16 |
| 18 | 25 |
| 26 | 5.4 |
| 36 | 6.3 |
| 37 | 1.2 |
| 43 | 1.5 |
| 47 | 9.2 |
| 59 | 0.3 |
| 62 | 7.9 |
| 65 | 12 |
| 67 | 6.6 |
| 68 | 7.2 |
| 69 | 4.5 |
| 70 | 2.1 |
| 71 | 5.5 |
| 72 | 32 |
| 73 | 38 |
| 74 | 20 |
| 75 | 18 |
| 76 | 4.8 |
| 77 | 2.5 |
| 78 | 1.4 |
| 79 | 7.6 |
| 80 | 3.6 |
| 85 | 1.1 |
| 86 | 16 |

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was conducted as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in the presence of compounds or DMSO controls for 30 minutes, then stimulated with glucagon (250 μM) for an additional 30 minutes. The cell stimulation was stopped by addition of equal amounts of a detection buffer containing lysis buffer as well as $^{125}$I-labeled cAMP tracer (NEN). After 3 hours of incubation at room temperature the bound radioactivity was determined in a liquid scintillation counter (Top-Count-Packard Instruments). Basal activity (100% inhibition) was determined using the DMSO control while 0% inhibition was defined at the amount of pmol cAMP produced by 250 μM glucagon. The resulting amount of cAMP generated per compound dose was back-calculated from a cAMP standard curve based on the percent inhibition achieved at each dose. The calculated cAMP levels were plotted versus compound dose to obtain IC$_{50}$ values using non-linear four-parameter curve fitting with Assay Data Analyzer software (Merck & Co., Inc.).

Certain embodiments of the invention have been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

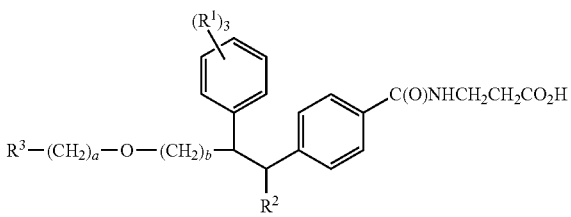

or a pharmaceutically acceptable salt thereof wherein:
each $R^1$ represents H or is selected from the group consisting of halo, CN, OH, NO$_2$, CO$_2$R$^a$, NR$^a$R$^b$, S(O)$_p$R$^a$, C$_{1-10}$alkyl, C$_{2-10}$alkenyl or C$_{1-10}$alkoxy, the alkyl and alkenyl portions of, C$_{1-10}$alkyl, C$_{2-10}$alkenyl and C$_{1-10}$alkoxy being optionally substituted with 1-5 halo atoms up to perhalo; and further optionally substituted with 1 group selected from OH, oxo and C$_{1-6}$alkoxy;
p represents 0, 1 or 2;
each R$^a$ and R$^b$ independently represents H or C$_{1-4}$-alkyl optionally substituted with 1-5 halo atoms up to perhalo; and further optionally substituted with 1 group selected from OH, oxo and C$_{1-6}$alkoxy;
$R^2$ represents C$_{1-6}$alkyl or C$_{2-6}$alkenyl, each optionally substituted with 1-5 halo atoms up to perhalo, and further optionally substituted with 1 group selected from OH, oxo and C$_{1-6}$alkoxy;
a and b represents integers selected from 0 and 1, such that the sum of a and b is 0, 1 or 2;
$R^3$ represents Aryl(R$^d$)$_3$ or Heteroaryl(R$^d$)$_3$ wherein the Heteroaryl group is a 5-10 membered group containing one or two rings, said Heteroaryl group containing one to three heteroatoms, 0-3 of which are nitrogen, and 0-1 of which is oxygen or sulfur;
each R$^d$ represents H or is selected from the group consisting of:
halo, CN, OH, NO$_2$, CO$_2$R$^a$, C(O)NH$_2$, NR$^a$R$^b$, S(O)$_p$R$^a$, C$_{1-10}$alkyl, C$_{2-10}$alkenyl, C$_{1-10}$alkoxy, haloC$_{1-10}$alkoxy, phenyl(R$^e$)$_3$ and HAR(R$^e$)$_3$;
each R$^e$ represents H or is selected from the group consisting of: halo, CN, haloC$_{1-6}$alkyl, C$_{1-6}$alkoxy and haloC$_{1-6}$alkoxy.

2. A compound in accordance with claim 1 or a pharmaceutically acceptable salt thereof wherein:
each $R^1$ represents H or is selected from the group consisting of halo, CN, NR$^a$R$^b$, S(O)$_p$R$^a$, C$_{1-10}$alkyl, C$_{2-10}$alkenyl or C$_{1-10}$alkoxy, the alkyl and alkenyl portions of, C$_{1-10}$alkyl, C$_{2-10}$alkenyl and C$_{1-10}$alkoxy being optionally substituted with 1-5 halo atoms up to perhalo; and further optionally substituted with 1 group selected from oxo and C$_{1-6}$alkoxy;
p represents 0 or 2;
each R$^a$ and R$^b$ independently represents H or CH$_3$.

3. A compound in accordance with claim 2 or a pharmaceutically acceptable salt thereof wherein:
each $R^1$ represents H or is selected from the group consisting of halo selected from chloro and fluoro, CN, NH$_2$, SO$_2$CH$_3$, C$_{1-3}$alkyl, C$_{2-3}$alkenyl or C$_{1-3}$alkoxy, the alkyl and alkenyl portions of, C$_{1-3}$alkyl, C$_{2-3}$alkenyl and C$_{1-3}$alkoxy being optionally substituted with 1-3 halo atoms selected from chloro and fluoro.

4. A compound in accordance with claim 3 or a pharmaceutically acceptable salt thereof wherein:
each $R^1$ represents H or is selected from the group consisting of chloro, fluoro, CN, $CH_3$, $OCH_3$, $CF_3$, $OCF_3$.

5. A compound in accordance with claim 1 or a pharmaceutically acceptable salt thereof wherein:
$R^2$ represents $C_{1-4}$alkyl or $C_{2-4}$alkenyl, each optionally substituted with 1-3 halo atoms.

6. A compound in accordance with claim 5 or a pharmaceutically acceptable salt thereof wherein:
$R^2$ represents $C_{3-4}$alkyl optionally substituted with 1-3 halo atoms selected from fluoro and chloro.

7. A compound in accordance with claim 6 or a pharmaceutically acceptable salt thereof wherein:
$R^2$ represents $—CH_2CH_2CH_3$ or $—CH_2CH_2CF_3$.

8. A compound in accordance with claim 1 or a pharmaceutically acceptable salt thereof wherein: a and b both equal zero; or a equals one and b equals zero; or a equals zero and b equals one, or a and b both equal one.

9. A compound in accordance with claim 1 or a pharmaceutically acceptable salt thereof wherein:
$R^3$ represents Aryl($R^d$)$_3$ or Heteroaryl($R^d$)$_3$ wherein the Aryl portion of Aryl($R^d$)$_3$ is phenyl or naphthyl, and the Heteroaryl portion of Heteroaryl($R^d$)$_3$ is selected from the group consisting of pyridyl, pyrrolyl, pyrazolyl, pyrimidinyl, pyrazinyl, thiazolyl, thiophene, quinolinyl, isoquinolinyl and benzothiazolyl.

10. A compound in accordance with claim 9 or a pharmaceutically acceptable salt thereof wherein:
$R^3$ represents Aryl($R^d$)$_3$ or Heteroaryl($R^d$)$_3$ wherein the Aryl portion of Aryl($R^d$)$_3$ is phenyl or naphthyl, and the Heteroaryl portion of Heteroaryl($R^d$)$_3$ is selected from the group consisting of pyridyl, pyrrolyl, thiophene, quinolinyl and benzothiazolyl.

11. A compound in accordance with claim 1 or a pharmaceutically acceptable salt thereof wherein:
each $R^d$ represents H or is selected from the group consisting of:
halo, CN, $C_{1-10}$alkyl, halo$C_{1-10}$alkyl, $C_{1-10}$alkoxy, halo$C_{1-10}$alkoxy, phenyl($R^e$)$_3$ and HAR($R^e$)$_3$;
wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl, and
each $R^e$ represents H or is selected from the group consisting of: halo, CN, $C_{1-6}$alkyl, halo $C_{1-6}$alkyl, $C_{1-6}$alkoxy and halo $C_{1-6}$alkoxy.

12. A compound in accordance with claim 11 or a pharmaceutically acceptable salt thereof wherein:
each $R^d$ represents H or is selected from the group consisting of:
halo, CN, $C_{1-4}$-alkyl, halo$C_{1-4}$alkyl, $C_{1-4}$-alkoxy, halo$C_{1-4}$alkoxy, phenyl($R^e$)$_3$ and HAR($R^e$)$_3$;
wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl,
and each $R^e$ represents H or is selected from the group consisting of: halo selected from Cl, Br and F, CN, $C_{1-4}$-alkyl, halo$C_{1-4}$-alkyl, $C_{1-4}$-alkoxy and halo$C_{1-4}$-alkoxy, the halo portions of which are selected from Cl and F.

13. A compound in accordance with claim 12 or a pharmaceutically acceptable salt thereof wherein:
each $R^d$ represents H or is selected from the group consisting of:
Cl, Br, F, CN, $CH_3$, t-butyl, $CF_3$, $OCH_3$, $OCHF_2$, $OCF_3$, phenyl($R^e$)$_3$ and HAR($R^e$)$_3$;
wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl,
and each $R^e$ represents H or is selected from the group consisting of: Cl, F, CN, $CH_3$, $CF_3$, $OCH_3$, $OCH(CH_3)_2$ and $OCF_3$.

14. A compound in accordance with claim 1 or a pharmaceutically acceptable salt thereof wherein:
each $R^1$ represents H or is selected from the group consisting of halo, CN, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from oxo and $C_{1-6}$alkoxy;
p represents 0 or 2;
each $R^a$ and $R^b$ independently represents H or $CH_3$,
$R^2$ represents $C_{1-4}$-alkyl or $C_{2-4}$alkenyl, each optionally substituted with 1-3 halo atoms.
a and b both equal zero; or a equals one and b equals zero; or a equals zero and b equals one, or a and b both equal one;
$R^3$ represents Aryl($R^d$)$_3$ or Heteroaryl($R^d$)$_3$ wherein the Aryl portion of Aryl($R^d$)$_3$ is phenyl or naphthyl, and the Heteroaryl portion of Heteroaryl($R^d$)$_3$ is selected from the group consisting of pyridyl, pyrrolyl, pyrazolyl, pyrimidinyl, pyrazinyl, thiazolyl, thiophene, quinolinyl, isoquinolinyl and benzothiazolyl;
each $R^d$ represents H or is selected from the group consisting of:
halo, CN, $C_{1-10}$alkyl, halo$C_{1-10}$alkyl, $C_{1-10}$alkoxy, halo$C_{1-10}$alkoxy, phenyl($R^e$)$_3$ and HAR($R^e$)$_3$;
wherein HAR is selected from the group consisting of pyridyl, pyrrolyl, pyrazolyl, pyrimidinyl, pyrazinyl, thiazolyl, thiophene, quinolinyl, isoquinolinyl and benzothiazolyl, and
and each $R^e$ represents H or is selected from the group consisting of: halo, CN, $C_{1-6}$alkyl, halo$C_{1-6}$alkyl, $C_{1-6}$alkoxy and halo$C_{1-6}$alkoxy.

15. A compound in accordance with claim 1 or a pharmaceutically acceptable salt thereof selected from one of the following tables:

EXAMPLE 1

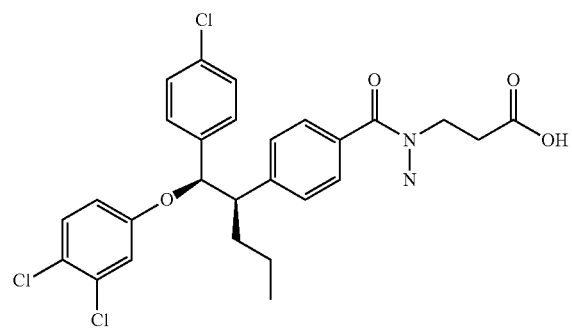

EXAMPLE 2
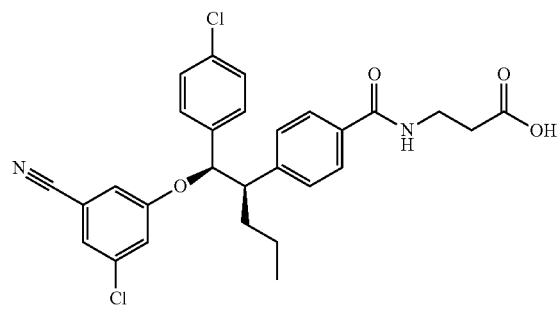
EXAMPLE 69
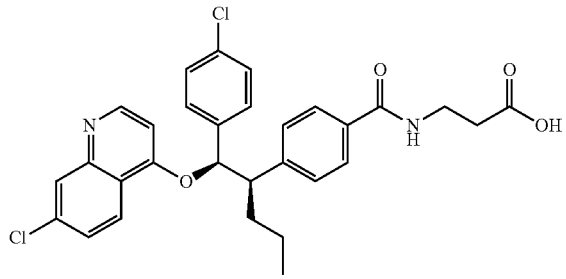
EXAMPLE 3
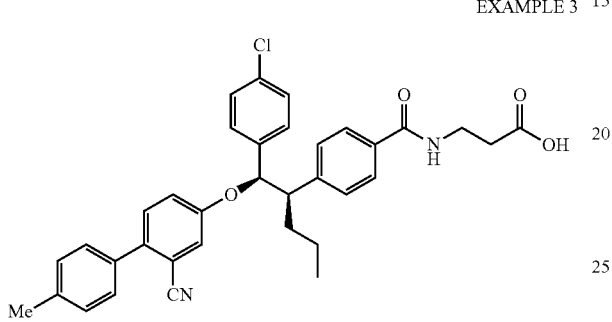
EXAMPLE 70
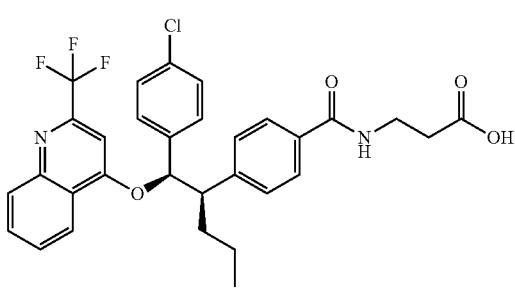
EXAMPLE 4
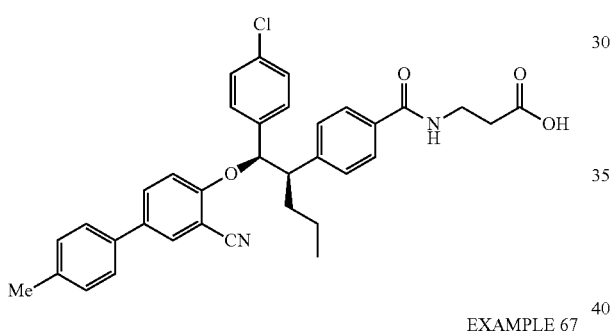
EXAMPLE 71
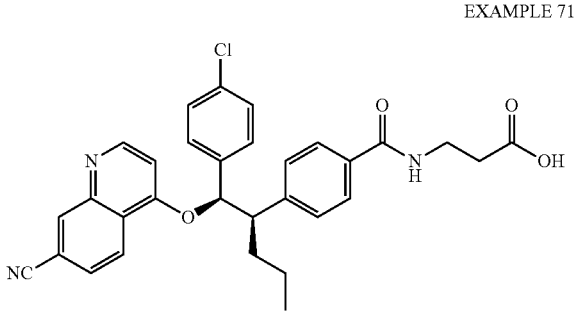
EXAMPLE 67
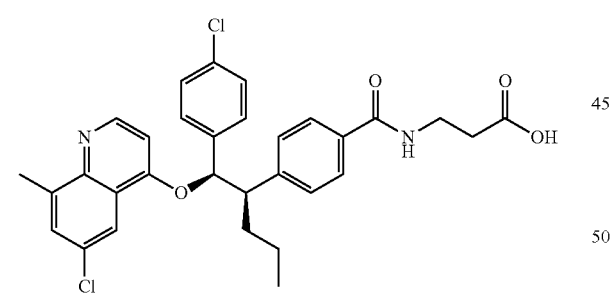
EXAMPLE 72
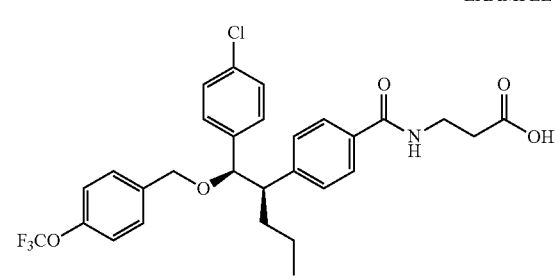
EXAMPLE 68
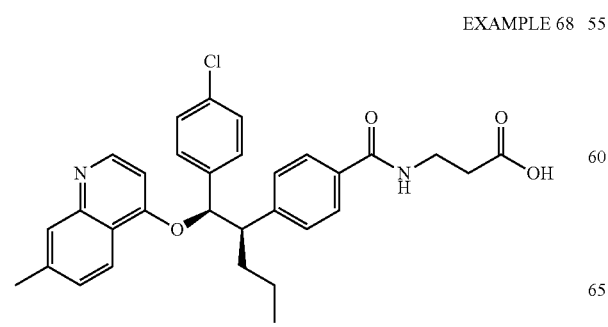
EXAMPLE 73
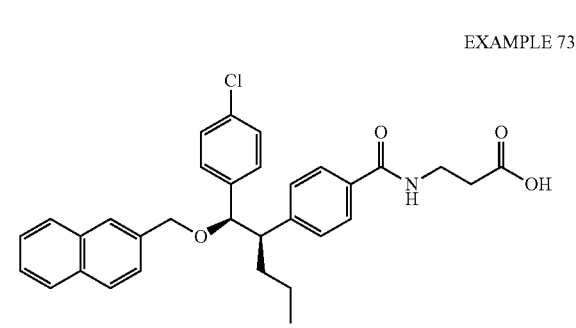

EXAMPLE 74
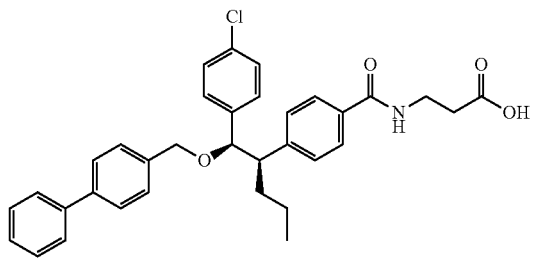
EXAMPLE 75
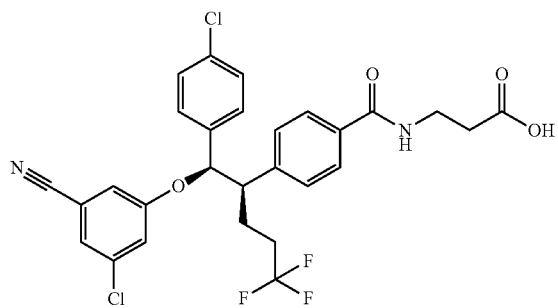
EXAMPLE 76
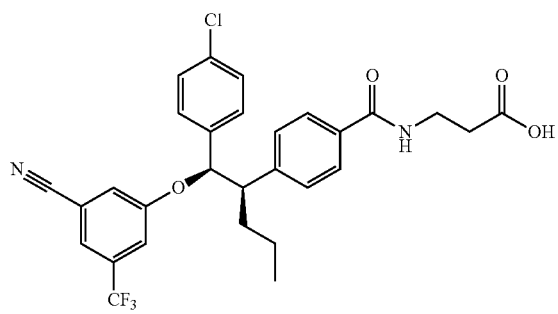
EXAMPLE 77
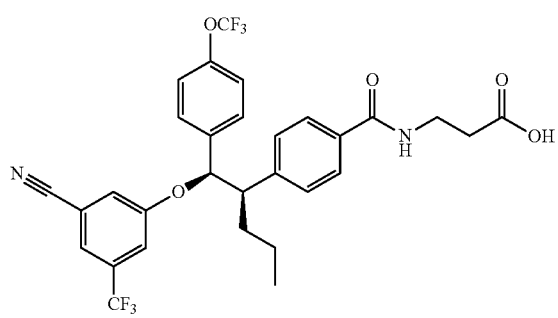
EXAMPLE 78
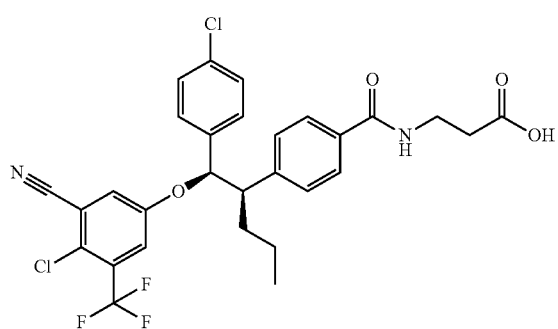
EXAMPLE 86
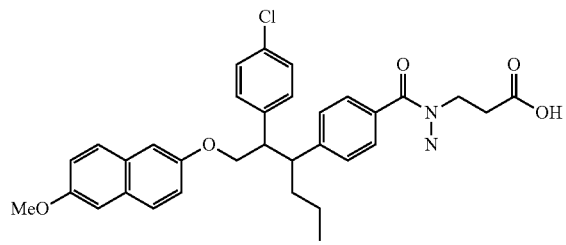
EXAMPLE 87
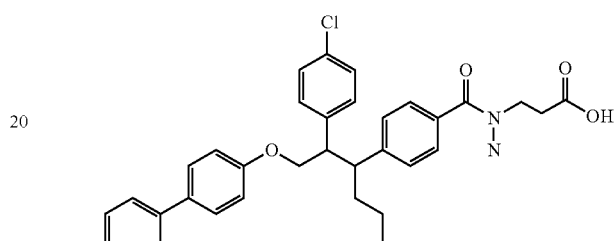
EXAMPLE 88
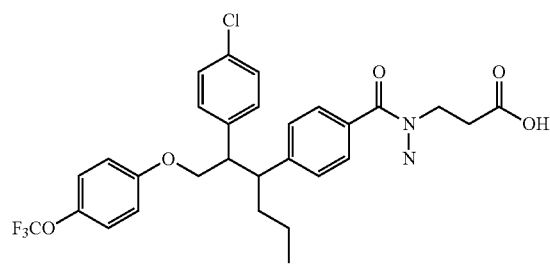
EXAMPLE 89
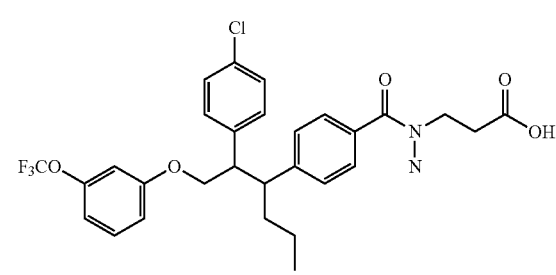
EXAMPLE 90
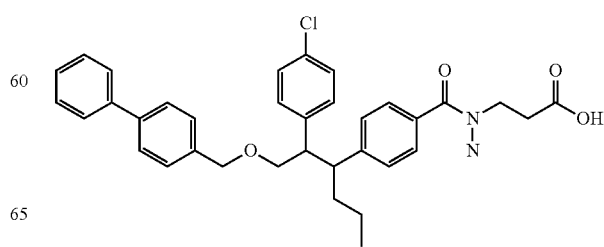

EXAMPLE 91
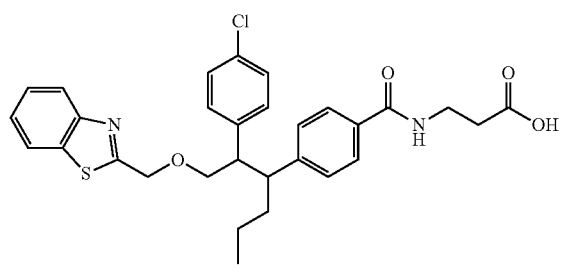
TABLE 1
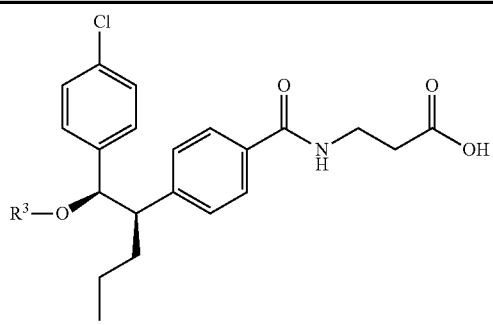
| EXAMPLE | R³ |
|---|---|
| 5 | <br>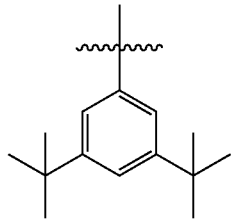 [SMILES: *c1cc(C(C)(C)C)cc(C(C)(C)C)c1] |
| 6 | <br>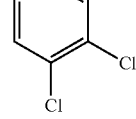 |
| 7 | 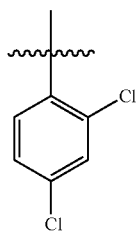 [SMILES: *c1ccc(Cl)cc1Cl] |
| 8 | 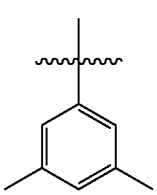 |
TABLE 1-continued
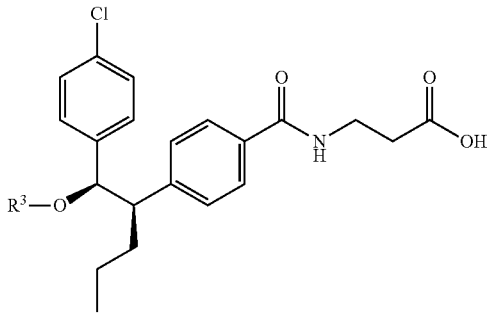
| EXAMPLE | R³ |
|---|---|
| 9 | 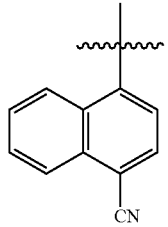 [SMILES: *c1ccc(C#N)c2ccccc12] |
| 10 | 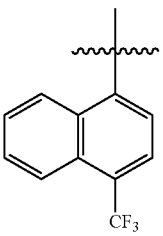 [SMILES: *c1ccc(C(F)(F)F)c2ccccc12] |
| 11 | 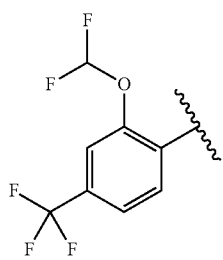 [SMILES: *c1ccc(C(F)(F)F)cc1OC(F)F] |
| 12 | 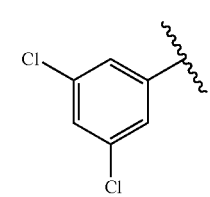 [SMILES: *c1cc(Cl)cc(Cl)c1] |
| 13 | 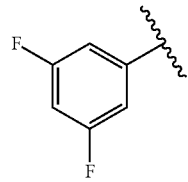 [SMILES: *c1cc(F)cc(F)c1] |

TABLE 1-continued
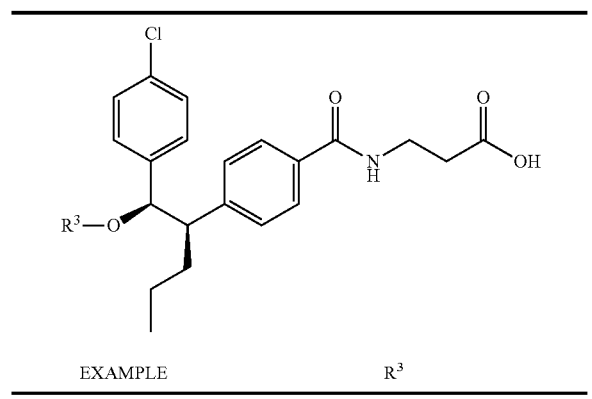
| EXAMPLE | R³ |
|---|---|
| 14 | 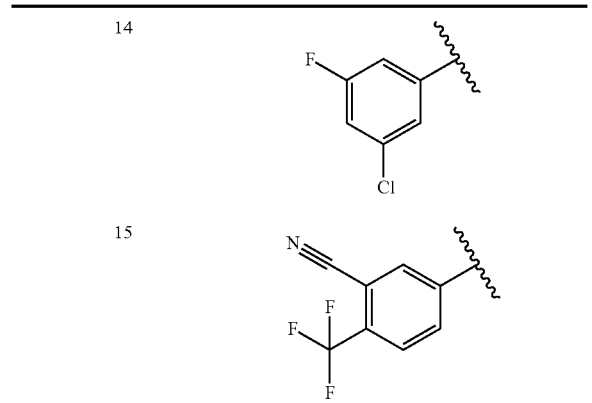 |
| 15 | |
| 16 | |
| 17 | |
| 18 | |
| 19 | |
| 20 | |
TABLE 1-continued
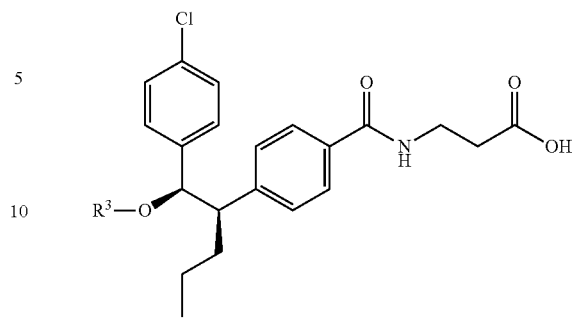
| EXAMPLE | R³ |
|---|---|
| 21 | 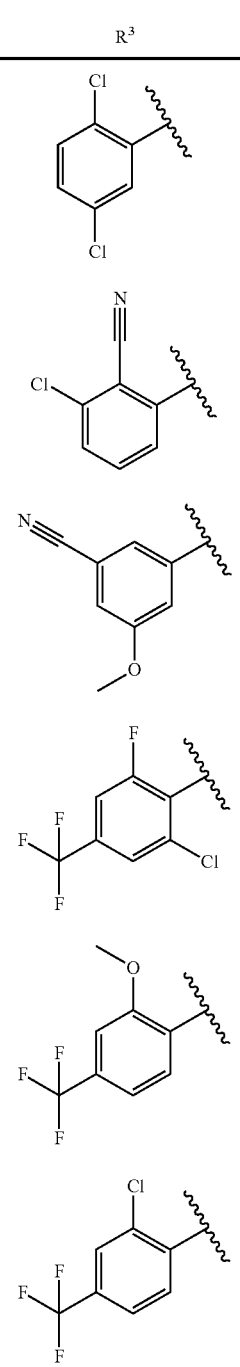 |
| 22 | |
| 23 | |
| 24 | |
| 25 | |
| 26 | |

TABLE 1-continued
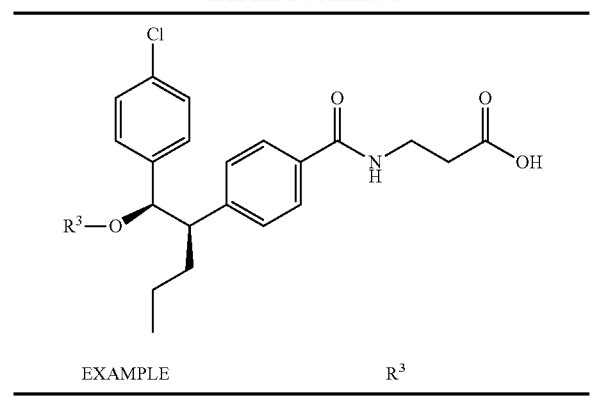
| EXAMPLE | R³ |
|---|---|
| 27 | 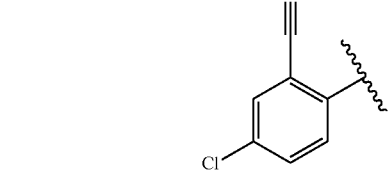 |
| 28 | 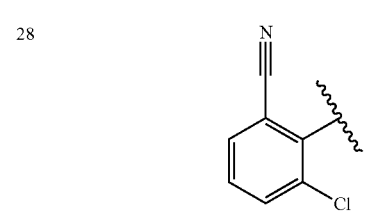 |
| 29 | 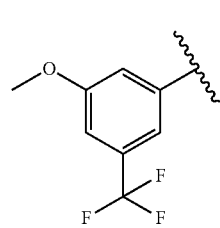 [SMILES: *c1cc(OC)cc(C(F)(F)F)c1] |
| 30 | 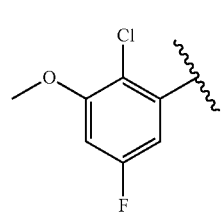 |
| 31 | 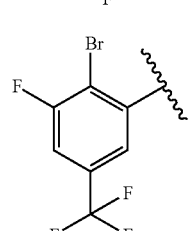 |
| 32 | 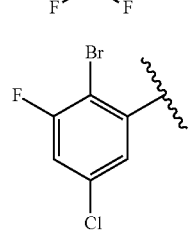 |
TABLE 1-continued
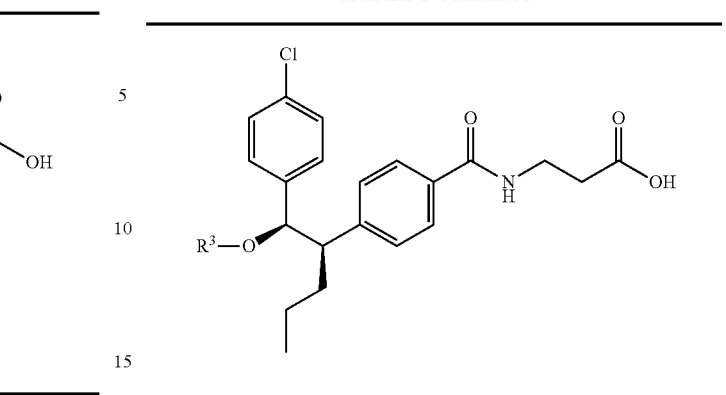
| EXAMPLE | R³ |
|---|---|
| 33 | 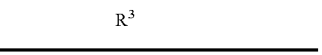 |
| 34 | 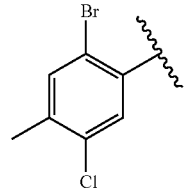 [SMILES: *c1cc(Cl)c(C)cc1Br] |
| 35 | 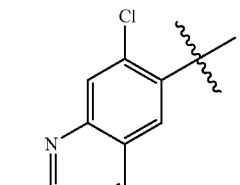 |
| 36 | 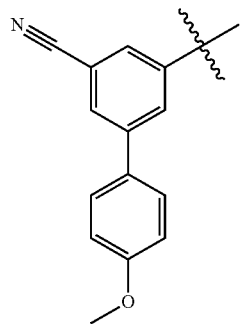 [SMILES: *c1cc(C#N)cc(-c2ccc(OC)cc2)c1] |

TABLE 2
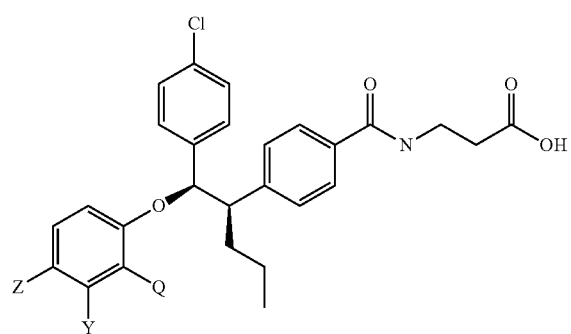
| EXAMPLE | Q | Y | Z |
|---|---|---|---|
| 37 | H | —CN | 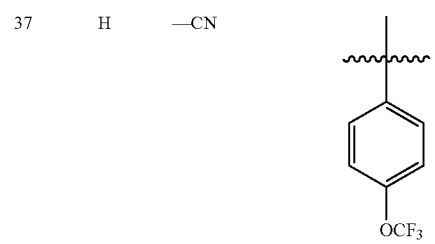 |
| 38 | H | —CN | 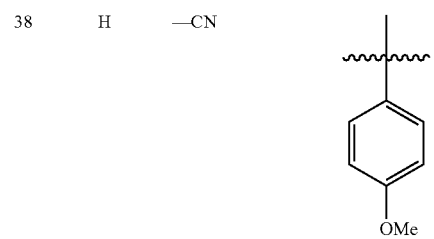 |
| 39 | H | —CN | 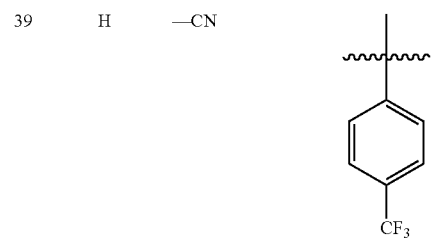 |
| 40 | H | —CN | 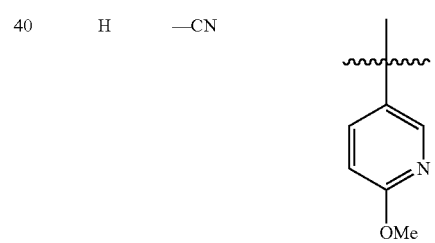 |
| 41 | H | —CN | 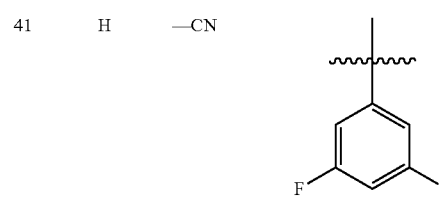 |
TABLE 2-continued
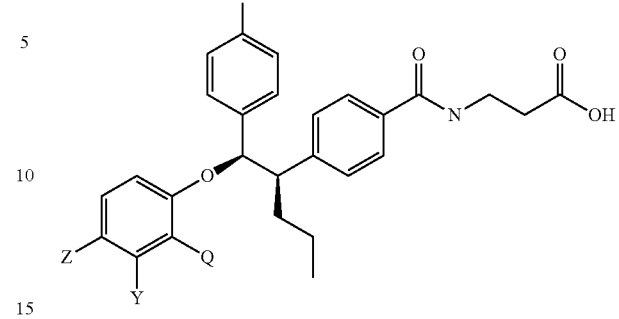
| EXAMPLE | Q | Y | Z |
|---|---|---|---|
| 42 | H | H | 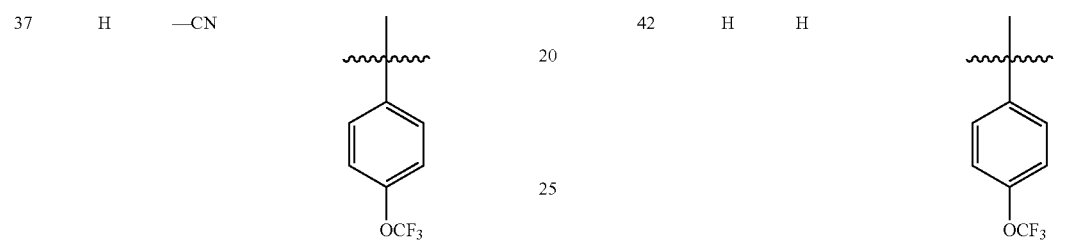 |
| 43 | H | H | 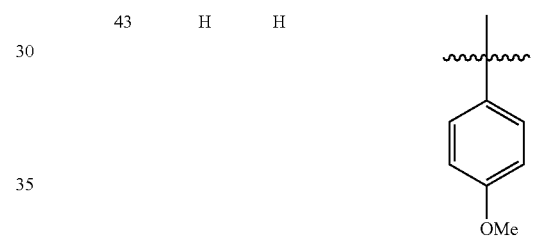 |
| 44 | H | H | 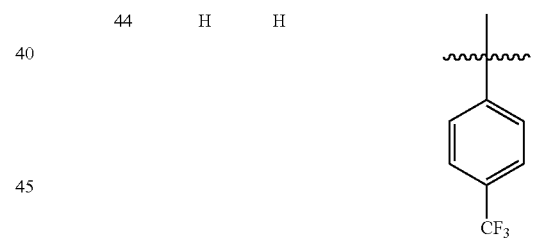 |
| 45 | H | H | 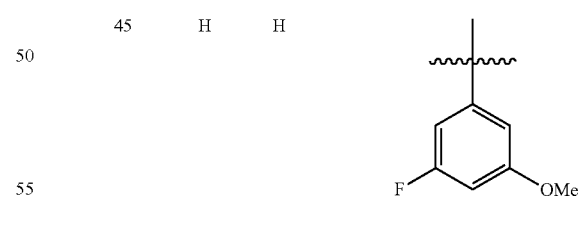 |
| 46 | H | H |  |

TABLE 2-continued
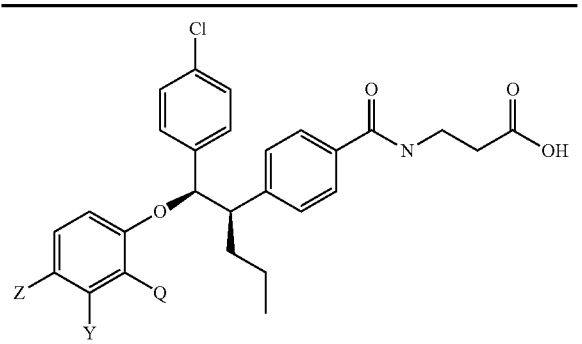
| EXAMPLE | Q | Y | Z |
|---|---|---|---|
| 47 | H | H | 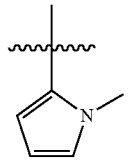 [SMILES: *c1cccn1C] |
| 48 | H | —CN | 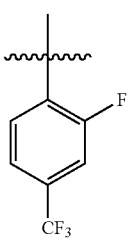 |
| 49 | H | —CN | 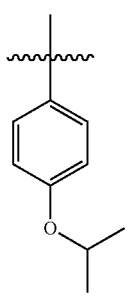 |
| 50 | H | —CN | 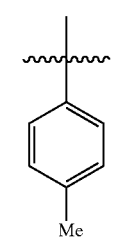 |
| 51 | H | —CN | 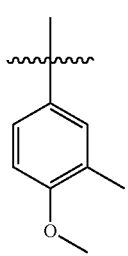 |
TABLE 2-continued
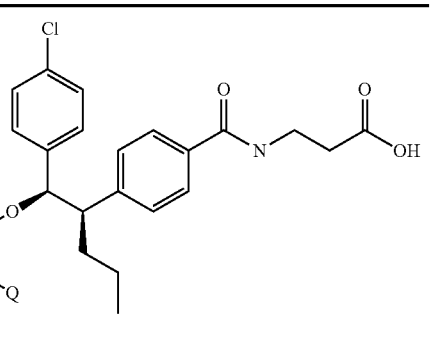
| EXAMPLE | Q | Y | Z |
|---|---|---|---|
| 52 | —CN | H | 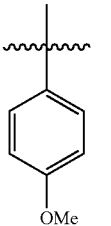 |
| 53 | —CN | H | 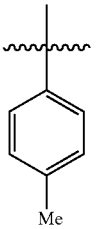 |
| 54 | —CN | H | 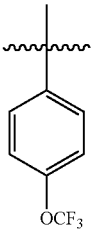 |
| 55 | —CN | H | 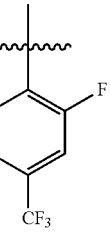 |
| 56 | —CN | H | 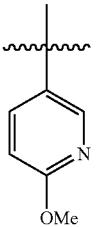 |

TABLE 2-continued
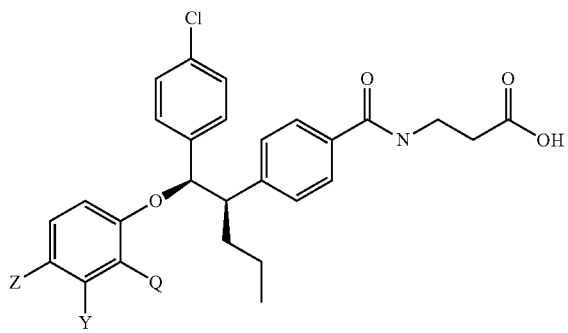
| EXAMPLE | Q | Y | Z |
|---|---|---|---|
| 57 | —CN | H | 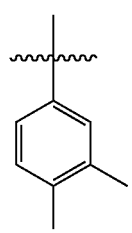 |
| 58 | —CN | H | 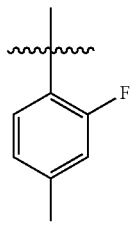 |
| 59 | —CN | H | 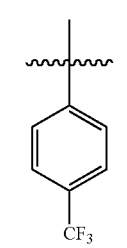 |
| 60 | H | —CN | 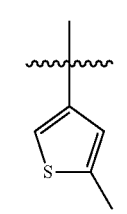 [SMILES: *c1csc(C)c1] |
| 61 | H | —CN | 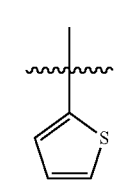 |
TABLE 3
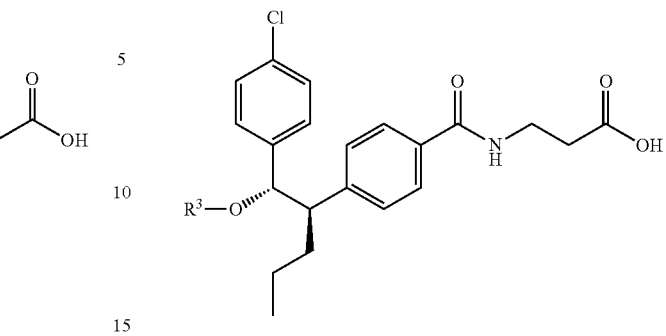
| EXAMPLE | R³ |
|---|---|
| 62 | 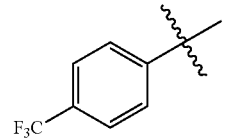 |
| 63 | 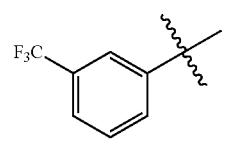 [SMILES: *c1cccc(C(F)(F)F)c1] |
| 64 | 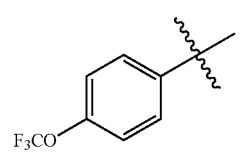 |
| 65 | 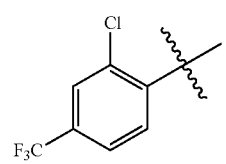 [SMILES: *c1ccc(C(F)(F)F)cc1Cl] |
| 66 | 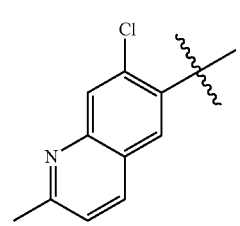 |

TABLE 4

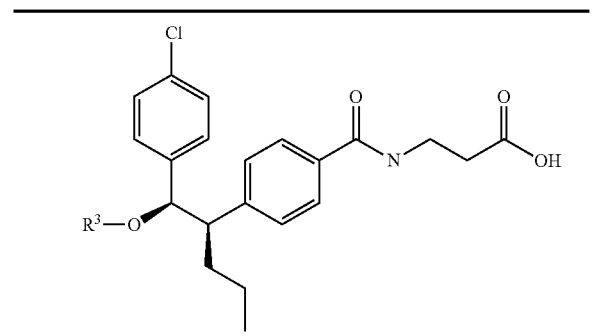

| EXAMPLE | R |
|---------|---|
| 79 | |
| 80 | |
| 81 | |
| 82 | |
| 83 | |

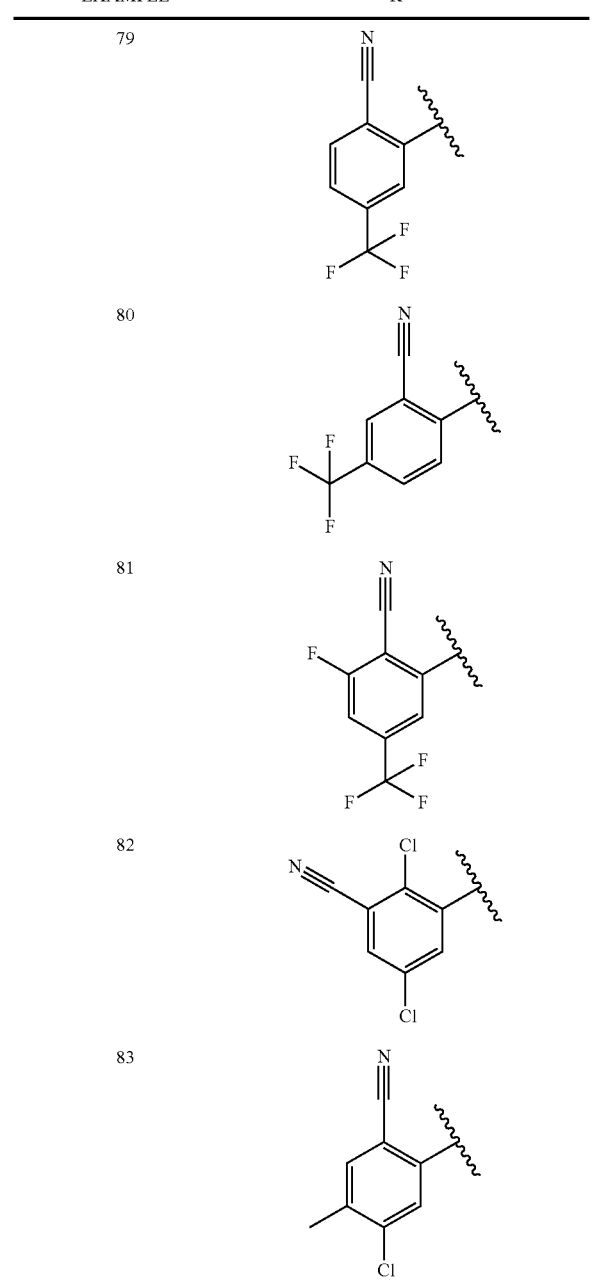

TABLE 4-continued

| 84 | 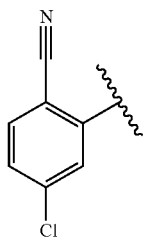 [SMILES: *c1cc(Cl)ccc1C#N] |
|----|---|
| 85 | 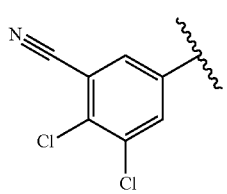 | or a pharmaceutically acceptable salt thereof.

16. A pharmaceutical composition comprising a compound in accordance with claim 1 or a pharmaceutically acceptable salt thereof in combination with a pharmaceutically acceptable carrier.

17. A pharmaceutical composition in accordance with claim 16 further comprised of a member selected from the group consisting of: simvastatin, mevastatin, ezetimibe, atorvastatin, metformin, sibutramine, orlistat, Qnexa, topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide, rimonabant and taranabant.

18. A method of treating type 2 diabetes mellitus in a mammalian patient in need of such treatment comprising administering to said patient a compound in accordance with claim 1 or a pharmaceutically acceptable salt thereof in an amount that is effective to treat said type 2 diabetes mellitus.

19. A method of delaying the onset of type 2 diabetes mellitus in a mammalian patient in need thereof, comprising administering to the patient a compound in accordance with claim 1 or a pharmaceutically acceptable salt thereof in an amount that is effective to delay the onset of said type 2 diabetes mellitus.

20. A method of treating hyperglycemia, diabetes or insulin resistance in a mammalian patient in need of such treatment which comprises administering to said patient an effective amount of a compound in accordance with claim 1 or a pharmaceutically acceptable salt thereof.

* * * * *